US006465213B1

(12) United States Patent
Ekstrand

(10) Patent No.: US 6,465,213 B1
(45) Date of Patent: Oct. 15, 2002

(54) NUCLEOTIDE SEQUENCES

(75) Inventor: Jonas Ekstrand, Umeå (SE)

(73) Assignee: Astra Aktiebolag (SE)

(*) Notice: Subject to any disclaimer, the term of this patent is extended or adjusted under 35 U.S.C. 154(b) by 0 days.

(21) Appl. No.: 09/422,936

(22) Filed: Oct. 22, 1999

Related U.S. Application Data

(63) Continuation-in-part of application No. 09/242,608, filed as application No. PCT/SE98/01947 on Oct. 27, 1998, now abandoned.

(30) Foreign Application Priority Data

Oct. 27, 1997 (SE) ........................................ 9703914
Mar. 16, 1998 (SE) ........................................ 9800864
Jul. 17, 1998 (SE) ........................................ 9802575

(51) Int. Cl.[7] ........................ C12P 12/06; C12Q 1/68; C07K 17/00; C07K 14/72

(52) U.S. Cl. .................... 435/69.1; 435/71.1; 435/71.2; 435/320.1; 435/325; 435/252.3; 435/254.11; 530/350; 536/23.1; 536/23.5; 536/24.3; 536/24.31

(58) Field of Search .............................. 536/23.1, 23.5, 536/24.3, 24.31; 530/350; 435/69.1, 71.1, 71.2, 325, 320.1, 471, 252.3, 254.11

(56) References Cited

FOREIGN PATENT DOCUMENTS

WO WO 97/46675 12/1997

OTHER PUBLICATIONS

Doerks et al., TIG, Jun. 1998, vol. 14, No. 6, pp. 248–250.*

Kerr; D.I.B. and Ong.; "$GABA_B$ Receptor", J. Pharmac. & Ther., vol. 67; pp. 187–246; 1995.

Kaupmann et al. "Expression cloning of $GABA_B$ Receptors Uncovers Similar to Metabotropic Glutamate Receptors" Nature, vol. 386; pp. 239–246; 1997.

Holloway et al.; "Pathophysiology of Gastroesophageal Reflux"; Gastroenterol. Clin. N. Amer., vol. 19: pp. 517–535; 1990.

Karlin et al.; "Methods of Assessing the Statistical Significance of Molecular Sequence Features by Using General Scoring Schemes"; Proc. Nat'l. Acad. Sci. USA, vol. 87; pp. 2264–2268; 1990.

Karlin et al.; "Applications and Statistics For Multiple High–Scoring Segments In Molecular Sequence"; Proc. Nat'l Acad. Sci. USA, vol. 90; pp. 5873–5877; 1993.

Altschul et al.; "Basic Local Alignment Search Tool"; J. Mol. Biiol., vol. 215; pp. 403–410; 1990.

Altschul et al.; "Gapped BLAST and PSI–BLAST: A New Generation of Protein Database Search Programs"; Nucleic Acids Res., vol. 25, pp. 3389–3402; 1997.

Ausubel et al.; "Contents, vol. 1,2,3, and 4"; Current Protocols in Molecular Biiology; John Wiley and Sons, Inc.; 1994 (manual).

Sambrook, Fritsch and Maniatis; "Contents"; Molecular Cloning: A laboratory manual 2nd Ed., Cold Spring Harbor Laboratory Press, Cold Spring Harbor, NY 1989.

Kaupmann et al.; EMBL accession Nos. Y10369; 1997.

Clontech, Lambda Library User Manual, PT 1010–1 (PR 92374) Feb. 1999.

* cited by examiner

*Primary Examiner*—Gary L. Kunz
*Assistant Examiner*—Sarada C Prasad
(74) *Attorney, Agent, or Firm*—Fish & Richardson P.C.

(57) ABSTRACT

The present invention relates to a nucleic acid molecule encoding a human or canine $GABA_B$ receptor, or a conservative variant thereof.

35 Claims, 2 Drawing Sheets

SEQUENCE LISTING

```
<160> NUMBER OF SEQ ID NOS:  85

<210> SEQ ID NO 1
<211> LENGTH: 27
<212> TYPE: DNA
<213> ORGANISM: Rattus norvegicus

<400> SEQUENCE: 1

gtttcttctc ggatccagct gtgcctg                                    27


<210> SEQ ID NO 2
<211> LENGTH: 28
<212> TYPE: DNA
<213> ORGANISM: Rattus norvegicus

<400> SEQUENCE: 2

caggcacagc tggatccgag aagaaact                                   28


<210> SEQ ID NO 3
<211> LENGTH: 38
<212> TYPE: DNA
<213> ORGANISM: Rattus norvegicus

<400> SEQUENCE: 3

cggtcgactc acttgtaaag caaatgtact cgactccc                        38


<210> SEQ ID NO 4
<211> LENGTH: 41
<212> TYPE: DNA
<213> ORGANISM: Rattus norvegicus

<400> SEQUENCE: 4

atgcgcgccg gcagccaaca tgctgctgct gctgctggtg c                    41


<210> SEQ ID NO 5
<211> LENGTH: 46
<212> TYPE: DNA
<213> ORGANISM: Rattus norvegicus

<400> SEQUENCE: 5

cggtcgactc acttgtaaag caaatgtact cgactcccat cacagc               46


<210> SEQ ID NO 6
<211> LENGTH: 50
<212> TYPE: DNA
<213> ORGANISM: Rattus norvegicus

<400> SEQUENCE: 6

atgcgcgccg gcagccaaca tgctgctgct gctgctggtg cctctcttcc           50


<210> SEQ ID NO 7
<211> LENGTH: 40
<212> TYPE: DNA
<213> ORGANISM: Rattus norvegicus

<400> SEQUENCE: 7

caggcacagc tggatccgag aagaaactct gtcggaaagt                      40


<210> SEQ ID NO 8
<211> LENGTH: 25
<212> TYPE: DNA
<213> ORGANISM: Rattus norvegicus
```

-continued

<400> SEQUENCE: 8
ggtcatccag cgttgaggtg aagac 25

<210> SEQ ID NO 9
<211> LENGTH: 25
<212> TYPE: DNA
<213> ORGANISM: Rattus norvegicus

<400> SEQUENCE: 9
gaaggttgcc agattataca tccgc 25

<210> SEQ ID NO 10
<211> LENGTH: 25
<212> TYPE: DNA
<213> ORGANISM: Rattus norvegicus

<400> SEQUENCE: 10
ccacgatgat tcgagcatct tgacg 25

<210> SEQ ID NO 11
<211> LENGTH: 22
<212> TYPE: DNA
<213> ORGANISM: Rattus norvegicus

<400> SEQUENCE: 11
gcctctcact cccctcatct cc 22

<210> SEQ ID NO 12
<211> LENGTH: 21
<212> TYPE: DNA
<213> ORGANISM: Homo sapiens

<400> SEQUENCE: 12
gagtgaagga ggctggaatt g 21

<210> SEQ ID NO 13
<211> LENGTH: 20
<212> TYPE: DNA
<213> ORGANISM: Homo sapiens

<400> SEQUENCE: 13
gacgcttatc gagcagcttc 20

<210> SEQ ID NO 14
<211> LENGTH: 24
<212> TYPE: DNA
<213> ORGANISM: Homo sapiens

<400> SEQUENCE: 14
agcccagaac tcacaggggg acat 24

<210> SEQ ID NO 15
<211> LENGTH: 23
<212> TYPE: DNA
<213> ORGANISM: Homo sapiens

<400> SEQUENCE: 15
gcttcaagcc aggtacgaac taa 23

<210> SEQ ID NO 16
<211> LENGTH: 27
<212> TYPE: DNA

-continued

```
<213> ORGANISM: Homo sapiens

<400> SEQUENCE: 16

tggccctcca ccgcctcagt catctca                                     27


<210> SEQ ID NO 17
<211> LENGTH: 27
<212> TYPE: DNA
<213> ORGANISM: Artificial Sequence
<220> FEATURE:
<223> OTHER INFORMATION: primer for PCR

<400> SEQUENCE: 17

ccatcctaat acgactcact atagggc                                     27


<210> SEQ ID NO 18
<211> LENGTH: 21
<212> TYPE: DNA
<213> ORGANISM: Homo sapiens

<400> SEQUENCE: 18

ctcaatctca tagtccactg g                                           21


<210> SEQ ID NO 19
<211> LENGTH: 19
<212> TYPE: DNA
<213> ORGANISM: Rattus norvegicus

<400> SEQUENCE: 19

ccttgaggcc cggggagag                                              19


<210> SEQ ID NO 20
<211> LENGTH: 28
<212> TYPE: DNA
<213> ORGANISM: Rattus norvegicus

<400> SEQUENCE: 20

caggcacagc tggatccgag aagaaact                                    28


<210> SEQ ID NO 21
<211> LENGTH: 46
<212> TYPE: DNA
<213> ORGANISM: Rattus norvegicus

<400> SEQUENCE: 21

cggtcgactc acttgtaaag caaatgtact cgactcccat cacagc                46


<210> SEQ ID NO 22
<211> LENGTH: 50
<212> TYPE: DNA
<213> ORGANISM: Rattus norvegicus

<400> SEQUENCE: 22

atgcgcgccg gcagccaaca tgctgctgct gctgctggtg cctctcttcc            50


<210> SEQ ID NO 23
<211> LENGTH: 22
<212> TYPE: DNA
<213> ORGANISM: Rattus norvegicus

<400> SEQUENCE: 23

cgtcaagatg ctcgaatcat cg                                          22
```

<210> SEQ ID NO 24
<211> LENGTH: 20
<212> TYPE: DNA
<213> ORGANISM: Rattus norvegicus

<400> SEQUENCE: 24 caggggctc agagggtccc 20

<210> SEQ ID NO 25
<211> LENGTH: 40
<212> TYPE: DNA
<213> ORGANISM: Rattus norvegicus

<400> SEQUENCE: 25
caggcacagc tggatccgag aagaaactct gtcggaaagt 40

<210> SEQ ID NO 26
<211> LENGTH: 50
<212> TYPE: DNA
<213> ORGANISM: Rattus norvegicus

<400> SEQUENCE: 26
cggtcgactc acttgtaaag caaatgtact cgactcccat cacagctaag 50

<210> SEQ ID NO 27
<211> LENGTH: 40
<212> TYPE: DNA
<213> ORGANISM: Rattus norvegicus

<400> SEQUENCE: 27
actttccgac agagtttctt ctcggatcca gctgtgcctg 40

<210> SEQ ID NO 28
<211> LENGTH: 25
<212> TYPE: DNA
<213> ORGANISM: Rattus norvegicus

<400> SEQUENCE: 28
ccacgatgat tcgagcatct tgacg 25

<210> SEQ ID NO 29
<211> LENGTH: 24
<212> TYPE: DNA
<213> ORGANISM: Canis familiaris

<400> SEQUENCE: 29
ctaccgcgca atgaactcct cgtc 24

<210> SEQ ID NO 30
<211> LENGTH: 24
<212> TYPE: DNA
<213> ORGANISM: Canis familiaris

<400> SEQUENCE: 30
cgaggtggcg ttgggggtct gtgc 24

<210> SEQ ID NO 31
<211> LENGTH: 27
<212> TYPE: DNA
<213> ORGANISM: Artificial Sequence
<220> FEATURE:
<223> OTHER INFORMATION: primer for PCR

<400> SEQUENCE: 31

-continued

```
ccatcctaat acgactcact atagggc                                            27


<210> SEQ ID NO 32
<211> LENGTH: 23
<212> TYPE: DNA
<213> ORGANISM: Artificial Sequence
<220> FEATURE:
<223> OTHER INFORMATION: primer for PCR

<400> SEQUENCE: 32

actcactata gggctcgagc ggc                                                23


<210> SEQ ID NO 33
<211> LENGTH: 20
<212> TYPE: DNA
<213> ORGANISM: Homo sapiens

<400> SEQUENCE: 33

gacgcttatc gagcagcttc                                                    20


<210> SEQ ID NO 34
<211> LENGTH: 24
<212> TYPE: DNA
<213> ORGANISM: Homo sapiens

<400> SEQUENCE: 34

agcccagaac tcacaggggg acat                                               24


<210> SEQ ID NO 35
<211> LENGTH: 23
<212> TYPE: DNA
<213> ORGANISM: Homo sapiens

<400> SEQUENCE: 35

gcttcaagcc aggtacgaac taa                                                23


<210> SEQ ID NO 36
<211> LENGTH: 22
<212> TYPE: DNA
<213> ORGANISM: Rattus norvegicus

<400> SEQUENCE: 36

ggagcacccc caagccccac tg                                                 22


<210> SEQ ID NO 37
<211> LENGTH: 18
<212> TYPE: DNA
<213> ORGANISM: Homo sapiens

<400> SEQUENCE: 37

ctggttcctc ccaatgtg                                                      18


<210> SEQ ID NO 38
<211> LENGTH: 20
<212> TYPE: DNA
<213> ORGANISM: Rattus norvegicus

<400> SEQUENCE: 38

cctctcactc ccctcatctc                                                    20


<210> SEQ ID NO 39
<211> LENGTH: 22
<212> TYPE: DNA
<213> ORGANISM: Homo sapiens
```

<400> SEQUENCE: 39
aagccaacct tccctgcttc tc 22

<210> SEQ ID NO 40
<211> LENGTH: 18
<212> TYPE: DNA
<213> ORGANISM: Homo sapiens

<400> SEQUENCE: 40
ctggttcctc ccaatgtg 18

<210> SEQ ID NO 41
<211> LENGTH: 20
<212> TYPE: DNA
<213> ORGANISM: Homo sapiens

<400> SEQUENCE: 41
gacgcttatc gagcagcttc 20

<210> SEQ ID NO 42
<211> LENGTH: 24
<212> TYPE: DNA
<213> ORGANISM: Canis familiaris

<400> SEQUENCE: 42
ctaccgcgca atgaactcct cgtc 24

<210> SEQ ID NO 43
<211> LENGTH: 24
<212> TYPE: DNA
<213> ORGANISM: Canis familiaris

<400> SEQUENCE: 43
ccttcttctc ctccttctta gtga 24

<210> SEQ ID NO 44
<211> LENGTH: 2883
<212> TYPE: DNA
<213> ORGANISM: Rattus norvegicus
<220> FEATURE:
<221> NAME/KEY: CDS
<222> LOCATION: (1)...(2880)

<400> SEQUENCE: 44

```
atg ctg ctg ctg ctg ctg gtg cct ctc ttc ctc cgc ccc ctg ggc gct       48
Met Leu Leu Leu Leu Leu Val Pro Leu Phe Leu Arg Pro Leu Gly Ala
 1               5                  10                  15

ggc ggg gcg cag acc ccc aac gcc acc tcg gaa ggt tgc cag att ata       96
Gly Gly Ala Gln Thr Pro Asn Ala Thr Ser Glu Gly Cys Gln Ile Ile
            20                  25                  30

cat ccg ccc tgg gaa ggt ggc atc agg tac cgt ggc ttg act cgc gac      144
His Pro Pro Trp Glu Gly Gly Ile Arg Tyr Arg Gly Leu Thr Arg Asp
        35                  40                  45

cag gtg aag gcc atc aac ttc ctg cct gtg gac tat gag atc gaa tat      192
Gln Val Lys Ala Ile Asn Phe Leu Pro Val Asp Tyr Glu Ile Glu Tyr
    50                  55                  60

gtg tgc cga ggg gag cgc gag gtg gtg ggg ccc aag gtg cgc aaa tgc      240
Val Cys Arg Gly Glu Arg Glu Val Val Gly Pro Lys Val Arg Lys Cys
 65                  70                  75                  80

ctg gcc aac ggc tcc tgg acg gat atg gac aca ccc agc cgc tgt gtc      288
Leu Ala Asn Gly Ser Trp Thr Asp Met Asp Thr Pro Ser Arg Cys Val
                85                  90                  95
```

-continued

```
cga atc tgc tcc aag tct tat ttg acc ctg gaa aat ggg aag gtt ttc      336
Arg Ile Cys Ser Lys Ser Tyr Leu Thr Leu Glu Asn Gly Lys Val Phe
            100                 105                 110

ctg acg ggt ggg gac ctc cca gct ctg gat gga gcc cgg gtg gag ttc      384
Leu Thr Gly Gly Asp Leu Pro Ala Leu Asp Gly Ala Arg Val Glu Phe
        115                 120                 125

cga tgt gac ccc gac ttc cat ctg gtg ggc agc tcc cgg agc gtc tgt      432
Arg Cys Asp Pro Asp Phe His Leu Val Gly Ser Ser Arg Ser Val Cys
    130                 135                 140

agt cag ggc cag tgg agc acc ccc aag ccc cac tgc cag gtg aat cga      480
Ser Gln Gly Gln Trp Ser Thr Pro Lys Pro His Cys Gln Val Asn Arg
145                 150                 155                 160

acg cca cac tca gaa cgg cgt gca gta tac atc ggg gcg ctg ttt ccc      528
Thr Pro His Ser Glu Arg Arg Ala Val Tyr Ile Gly Ala Leu Phe Pro
                165                 170                 175

atg agc ggg ggc tgg ccg ggg ggc cag gcc tgc cag ccc gcg gtg gag      576
Met Ser Gly Gly Trp Pro Gly Gly Gln Ala Cys Gln Pro Ala Val Glu
            180                 185                 190

atg gcg ctg gag gac gtt aac agc cgc aga gac atc ctg ccg gac tac      624
Met Ala Leu Glu Asp Val Asn Ser Arg Arg Asp Ile Leu Pro Asp Tyr
        195                 200                 205

gag ctc aag ctt atc cac cac gac agc aag tgt gac cca ggg caa gcc      672
Glu Leu Lys Leu Ile His His Asp Ser Lys Cys Asp Pro Gly Gln Ala
    210                 215                 220

acc aag tac ttg tac gaa cta ctc tac aat gac ccc atc aag atc att      720
Thr Lys Tyr Leu Tyr Glu Leu Leu Tyr Asn Asp Pro Ile Lys Ile Ile
225                 230                 235                 240

ctc atg cct ggc tgt agt tct gtc tcc aca ctt gta gct gag gct gcc      768
Leu Met Pro Gly Cys Ser Ser Val Ser Thr Leu Val Ala Glu Ala Ala
                245                 250                 255

cgg atg tgg aac ctt att gtg ctc tca tat ggc tcc agt tca cca gcc      816
Arg Met Trp Asn Leu Ile Val Leu Ser Tyr Gly Ser Ser Ser Pro Ala
            260                 265                 270

ttg tca aac cga cag cgg ttt ccc acg ttc ttc cgg acg cat cca tcc      864
Leu Ser Asn Arg Gln Arg Phe Pro Thr Phe Phe Arg Thr His Pro Ser
        275                 280                 285

gcc aca ctc cac aat ccc acc cgg gtg aaa ctc ttc gaa aag tgg ggc      912
Ala Thr Leu His Asn Pro Thr Arg Val Lys Leu Phe Glu Lys Trp Gly
    290                 295                 300

tgg aag aag atc gct acc atc caa cag acc acc gag gtc ttc acc tca      960
Trp Lys Lys Ile Ala Thr Ile Gln Gln Thr Thr Glu Val Phe Thr Ser
305                 310                 315                 320

acg ctg gat gac ctg gag gag cga gtg aaa gag gct ggg atc gag atc     1008
Thr Leu Asp Asp Leu Glu Glu Arg Val Lys Glu Ala Gly Ile Glu Ile
                325                 330                 335

act ttc cga cag agt ttc ttc tcg gat cca gct gtg cct gtt aaa aac     1056
Thr Phe Arg Gln Ser Phe Phe Ser Asp Pro Ala Val Pro Val Lys Asn
            340                 345                 350

ctg aag cgt caa gat gct cga atc atc gtg gga ctt ttc tat gag acg     1104
Leu Lys Arg Gln Asp Ala Arg Ile Ile Val Gly Leu Phe Tyr Glu Thr
        355                 360                 365

gaa gcc cgg aaa gtt ttt tgt gag gtc tat aag gaa agg ctc ttt ggg     1152
Glu Ala Arg Lys Val Phe Cys Glu Val Tyr Lys Glu Arg Leu Phe Gly
    370                 375                 380

aag aag tac gtc tgg ttc ctc atc ggg tgg tat gct gac aac tgg ttc     1200
Lys Lys Tyr Val Trp Phe Leu Ile Gly Trp Tyr Ala Asp Asn Trp Phe
385                 390                 395                 400

aag acc tat gac ccg tca atc aat tgt aca gtg gaa gaa atg acc gag     1248
Lys Thr Tyr Asp Pro Ser Ile Asn Cys Thr Val Glu Glu Met Thr Glu
```

-continued

```
                405                 410                 415

gcg gtg gag ggc cac atc acc acg gag att gtc atg ctg aac cct gcc     1296
Ala Val Glu Gly His Ile Thr Thr Glu Ile Val Met Leu Asn Pro Ala
            420                 425                 430

aac acc cga agc att tcc aac atg acg tca cag gaa ttt gtg gag aaa     1344
Asn Thr Arg Ser Ile Ser Asn Met Thr Ser Gln Glu Phe Val Glu Lys
        435                 440                 445

cta acc aag cgg ctg aaa aga cac ccc gag gag act gga ggc ttc cag     1392
Leu Thr Lys Arg Leu Lys Arg His Pro Glu Glu Thr Gly Gly Phe Gln
    450                 455                 460

gag gca cca ctg gcc tat gat gct atc tgg gcc ttg gct ttg gcc ttg     1440
Glu Ala Pro Leu Ala Tyr Asp Ala Ile Trp Ala Leu Ala Leu Ala Leu
465                 470                 475                 480

aac aag acg tct gga gga ggt ggt cgt tcc ggc gtg cgc ctg gag gac     1488
Asn Lys Thr Ser Gly Gly Gly Gly Arg Ser Gly Val Arg Leu Glu Asp
                485                 490                 495

ttt aac tac aac aac cag acc att aca gac cag atc tac cgg gcc atg     1536
Phe Asn Tyr Asn Asn Gln Thr Ile Thr Asp Gln Ile Tyr Arg Ala Met
            500                 505                 510

aac tcc tcc tcc ttt gag ggc gtt tct ggc cat gtg gtc ttt gat gcc     1584
Asn Ser Ser Ser Phe Glu Gly Val Ser Gly His Val Val Phe Asp Ala
        515                 520                 525

agc ggc tcc cgg atg gca tgg aca ctt atc gag cag cta cag ggc ggc     1632
Ser Gly Ser Arg Met Ala Trp Thr Leu Ile Glu Gln Leu Gln Gly Gly
    530                 535                 540

agc tac aag aag atc ggc tac tac gac agc acc aag gat gat ctt tcc     1680
Ser Tyr Lys Lys Ile Gly Tyr Tyr Asp Ser Thr Lys Asp Asp Leu Ser
545                 550                 555                 560

tgg tcc aaa acg gac aag tgg att gga ggg tct ccc cca gct gac cag     1728
Trp Ser Lys Thr Asp Lys Trp Ile Gly Gly Ser Pro Pro Ala Asp Gln
                565                 570                 575

acc ttg gtc atc aag aca ttc cgt ttc ctg tct cag aaa ctc ttt atc     1776
Thr Leu Val Ile Lys Thr Phe Arg Phe Leu Ser Gln Lys Leu Phe Ile
            580                 585                 590

tcc gtc tca gtt ctc tcc agc ctg ggc att gtt ctt gct gtt gtc tgt     1824
Ser Val Ser Val Leu Ser Ser Leu Gly Ile Val Leu Ala Val Val Cys
        595                 600                 605

ctg tcc ttt aac atc tac aac tcc cac gtt cgt tat atc cag aac tcc     1872
Leu Ser Phe Asn Ile Tyr Asn Ser His Val Arg Tyr Ile Gln Asn Ser
    610                 615                 620

cag ccc aac ctg aac aat ctg act gct gtg ggc tgc tca ctg gca ctg     1920
Gln Pro Asn Leu Asn Asn Leu Thr Ala Val Gly Cys Ser Leu Ala Leu
625                 630                 635                 640

gct gct gtc ttc cct ctc ggg ctg gat ggt tac cac ata ggg aga agc     1968
Ala Ala Val Phe Pro Leu Gly Leu Asp Gly Tyr His Ile Gly Arg Ser
                645                 650                 655

cag ttc ccg ttt gtc tgc cag gcc cgc ctt tgg ctc ttg ggc ttg ggc     2016
Gln Phe Pro Phe Val Cys Gln Ala Arg Leu Trp Leu Leu Gly Leu Gly
            660                 665                 670

ttt agt ctg ggc tat ggc tct atg ttc acc aag atc tgg tgg gtc cac     2064
Phe Ser Leu Gly Tyr Gly Ser Met Phe Thr Lys Ile Trp Trp Val His
        675                 680                 685

aca gtc ttc acg aag aag gag gag aag aag gag tgg agg aag acc cta     2112
Thr Val Phe Thr Lys Lys Glu Glu Lys Lys Glu Trp Arg Lys Thr Leu
    690                 695                 700

gag ccc tgg aaa ctc tat gcc act gtg ggc ctg ctg gtg ggc atg gat     2160
Glu Pro Trp Lys Leu Tyr Ala Thr Val Gly Leu Leu Val Gly Met Asp
705                 710                 715                 720

gtc ctg act ctt gcc atc tgg cag att gtg gac ccc ttg cac cga acc     2208
```

-continued

Val Leu Thr Leu Ala Ile Trp Gln Ile Val Asp Pro Leu His Arg Thr
                725                 730                 735 att gag act ttt gcc aag gag gaa cca aag gaa gac atc gat gtc tcc      2256
Ile Glu Thr Phe Ala Lys Glu Glu Pro Lys Glu Asp Ile Asp Val Ser
            740                 745                 750 att ctg ccc cag ttg gag cac tgc agc tcc aag aag atg aat acg tgg      2304
Ile Leu Pro Gln Leu Glu His Cys Ser Ser Lys Lys Met Asn Thr Trp
        755                 760                 765 ctt ggc att ttc tat ggt tac aag ggg ctg ctg ctg ctg ctg gga atc      2352
Leu Gly Ile Phe Tyr Gly Tyr Lys Gly Leu Leu Leu Leu Leu Gly Ile
    770                 775                 780 ttt ctt gct tac gaa acc aag agc gtg tcc act gaa aag atc aat gac      2400
Phe Leu Ala Tyr Glu Thr Lys Ser Val Ser Thr Glu Lys Ile Asn Asp
785                 790                 795                 800 cac agg gcc gtg ggc atg gct atc tac aat gtc gcg gtc ctg tgt ctc      2448
His Arg Ala Val Gly Met Ala Ile Tyr Asn Val Ala Val Leu Cys Leu
                805                 810                 815 atc act gct cct gtg acc atg atc ctt tcc agt cag cag gac gca gcc      2496
Ile Thr Ala Pro Val Thr Met Ile Leu Ser Ser Gln Gln Asp Ala Ala
            820                 825                 830 ttt gcc ttt gcc tct ctg gcc atc gtg ttc tct tcc tac atc act ctg      2544
Phe Ala Phe Ala Ser Leu Ala Ile Val Phe Ser Ser Tyr Ile Thr Leu
        835                 840                 845 gtt gtg ctc ttt gtg ccc aag atg cgc agg ctg atc acc cga ggg gaa      2592
Val Val Leu Phe Val Pro Lys Met Arg Arg Leu Ile Thr Arg Gly Glu
    850                 855                 860 tgg cag tct gaa acg cag gac acc atg aaa aca gga tca tcc acc aac      2640
Trp Gln Ser Glu Thr Gln Asp Thr Met Lys Thr Gly Ser Ser Thr Asn
865                 870                 875                 880 aac aac gag gaa gag aag tcc cga ctg ttg gag aag gaa aac cga gaa      2688
Asn Asn Glu Glu Glu Lys Ser Arg Leu Leu Glu Lys Glu Asn Arg Glu
                885                 890                 895 ctg gaa aag atc atc gct gag aaa gag gag cgc gtc tct gaa ctg cgc      2736
Leu Glu Lys Ile Ile Ala Glu Lys Glu Glu Arg Val Ser Glu Leu Arg
            900                 905                 910 cat cag ctc cag tct cgg cag caa ctc cgc tca cgg cgc cac ccc cca      2784
His Gln Leu Gln Ser Arg Gln Gln Leu Arg Ser Arg Arg His Pro Pro
        915                 920                 925 aca ccc cca gat ccc tct ggg ggc ctt ccc agg gga ccc tct gag ccc      2832
Thr Pro Pro Asp Pro Ser Gly Gly Leu Pro Arg Gly Pro Ser Glu Pro
    930                 935                 940 cct gac cgg ctt agc tgt gat ggg agt cga gta cat ttg ctt tac aag      2880
Pro Asp Arg Leu Ser Cys Asp Gly Ser Arg Val His Leu Leu Tyr Lys
945                 950                 955                 960
tga                                                                  2883

<210> SEQ ID NO 45
<211> LENGTH: 960
<212> TYPE: PRT
<213> ORGANISM: Rattus norvegicus

<400> SEQUENCE: 45

Met Leu Leu Leu Leu Leu Val Pro Leu Phe Leu Arg Pro Leu Gly Ala
 1               5                  10                  15

Gly Gly Ala Gln Thr Pro Asn Ala Thr Ser Glu Gly Cys Gln Ile Ile
            20                  25                  30

His Pro Pro Trp Glu Gly Gly Ile Arg Tyr Arg Gly Leu Thr Arg Asp
        35                  40                  45

Gln Val Lys Ala Ile Asn Phe Leu Pro Val Asp Tyr Glu Ile Glu Tyr
    50                  55                  60

-continued

```
Val Cys Arg Gly Glu Arg Glu Val Val Gly Pro Lys Val Arg Lys Cys
65                  70                  75                  80

Leu Ala Asn Gly Ser Trp Thr Asp Met Asp Thr Pro Ser Arg Cys Val
                85                  90                  95

Arg Ile Cys Ser Lys Ser Tyr Leu Thr Leu Glu Asn Gly Lys Val Phe
            100                 105                 110

Leu Thr Gly Gly Asp Leu Pro Ala Leu Asp Gly Ala Arg Val Glu Phe
        115                 120                 125

Arg Cys Asp Pro Asp Phe His Leu Val Gly Ser Ser Arg Ser Val Cys
    130                 135                 140

Ser Gln Gly Gln Trp Ser Thr Pro Lys Pro His Cys Gln Val Asn Arg
145                 150                 155                 160

Thr Pro His Ser Glu Arg Arg Ala Val Tyr Ile Gly Ala Leu Phe Pro
                165                 170                 175

Met Ser Gly Gly Trp Pro Gly Gly Gln Ala Cys Gln Pro Ala Val Glu
            180                 185                 190

Met Ala Leu Glu Asp Val Asn Ser Arg Arg Asp Ile Leu Pro Asp Tyr
        195                 200                 205

Glu Leu Lys Leu Ile His His Asp Ser Lys Cys Asp Pro Gly Gln Ala
    210                 215                 220

Thr Lys Tyr Leu Tyr Glu Leu Leu Tyr Asn Asp Pro Ile Lys Ile Ile
225                 230                 235                 240

Leu Met Pro Gly Cys Ser Ser Val Ser Thr Leu Val Ala Glu Ala Ala
                245                 250                 255

Arg Met Trp Asn Leu Ile Val Leu Ser Tyr Gly Ser Ser Ser Pro Ala
            260                 265                 270

Leu Ser Asn Arg Gln Arg Phe Pro Thr Phe Phe Arg Thr His Pro Ser
        275                 280                 285

Ala Thr Leu His Asn Pro Thr Arg Val Lys Leu Phe Glu Lys Trp Gly
    290                 295                 300

Trp Lys Lys Ile Ala Thr Ile Gln Gln Thr Thr Glu Val Phe Thr Ser
305                 310                 315                 320

Thr Leu Asp Asp Leu Glu Glu Arg Val Lys Glu Ala Gly Ile Glu Ile
                325                 330                 335

Thr Phe Arg Gln Ser Phe Phe Ser Asp Pro Ala Val Pro Val Lys Asn
            340                 345                 350

Leu Lys Arg Gln Asp Ala Arg Ile Ile Val Gly Leu Phe Tyr Glu Thr
        355                 360                 365

Glu Ala Arg Lys Val Phe Cys Glu Val Tyr Lys Glu Arg Leu Phe Gly
    370                 375                 380

Lys Lys Tyr Val Trp Phe Leu Ile Gly Trp Tyr Ala Asp Asn Trp Phe
385                 390                 395                 400

Lys Thr Tyr Asp Pro Ser Ile Asn Cys Thr Val Glu Glu Met Thr Glu
                405                 410                 415

Ala Val Glu Gly His Ile Thr Thr Glu Ile Val Met Leu Asn Pro Ala
            420                 425                 430

Asn Thr Arg Ser Ile Ser Asn Met Thr Ser Gln Glu Phe Val Glu Lys
        435                 440                 445

Leu Thr Lys Arg Leu Lys Arg His Pro Glu Glu Thr Gly Gly Phe Gln
    450                 455                 460

Glu Ala Pro Leu Ala Tyr Asp Ala Ile Trp Ala Leu Ala Leu Ala Leu
465                 470                 475                 480
```

-continued

```
Asn Lys Thr Ser Gly Gly Gly Gly Arg Ser Gly Val Arg Leu Glu Asp
                485                 490                 495

Phe Asn Tyr Asn Asn Gln Thr Ile Thr Asp Gln Ile Tyr Arg Ala Met
            500                 505                 510

Asn Ser Ser Ser Phe Glu Gly Val Ser Gly His Val Val Phe Asp Ala
        515                 520                 525

Ser Gly Ser Arg Met Ala Trp Thr Leu Ile Glu Gln Leu Gln Gly Gly
    530                 535                 540

Ser Tyr Lys Lys Ile Gly Tyr Tyr Asp Ser Thr Lys Asp Asp Leu Ser
545                 550                 555                 560

Trp Ser Lys Thr Asp Lys Trp Ile Gly Gly Ser Pro Pro Ala Asp Gln
                565                 570                 575

Thr Leu Val Ile Lys Thr Phe Arg Phe Leu Ser Gln Lys Leu Phe Ile
            580                 585                 590

Ser Val Ser Val Leu Ser Ser Leu Gly Ile Val Leu Ala Val Val Cys
        595                 600                 605

Leu Ser Phe Asn Ile Tyr Asn Ser His Val Arg Tyr Ile Gln Asn Ser
    610                 615                 620

Gln Pro Asn Leu Asn Asn Leu Thr Ala Val Gly Cys Ser Leu Ala Leu
625                 630                 635                 640

Ala Ala Val Phe Pro Leu Gly Leu Asp Gly Tyr His Ile Gly Arg Ser
                645                 650                 655

Gln Phe Pro Phe Val Cys Gln Ala Arg Leu Trp Leu Leu Gly Leu Gly
            660                 665                 670

Phe Ser Leu Gly Tyr Gly Ser Met Phe Thr Lys Ile Trp Trp Val His
        675                 680                 685

Thr Val Phe Thr Lys Lys Glu Glu Lys Lys Glu Trp Arg Lys Thr Leu
    690                 695                 700

Glu Pro Trp Lys Leu Tyr Ala Thr Val Gly Leu Leu Val Gly Met Asp
705                 710                 715                 720

Val Leu Thr Leu Ala Ile Trp Gln Ile Val Asp Pro Leu His Arg Thr
                725                 730                 735

Ile Glu Thr Phe Ala Lys Glu Glu Pro Lys Glu Asp Ile Asp Val Ser
            740                 745                 750

Ile Leu Pro Gln Leu Glu His Cys Ser Ser Lys Lys Met Asn Thr Trp
        755                 760                 765

Leu Gly Ile Phe Tyr Gly Tyr Lys Gly Leu Leu Leu Leu Leu Gly Ile
    770                 775                 780

Phe Leu Ala Tyr Glu Thr Lys Ser Val Ser Thr Glu Lys Ile Asn Asp
785                 790                 795                 800

His Arg Ala Val Gly Met Ala Ile Tyr Asn Val Ala Val Leu Cys Leu
                805                 810                 815

Ile Thr Ala Pro Val Thr Met Ile Leu Ser Ser Gln Gln Asp Ala Ala
            820                 825                 830

Phe Ala Phe Ala Ser Leu Ala Ile Val Phe Ser Ser Tyr Ile Thr Leu
        835                 840                 845

Val Val Leu Phe Val Pro Lys Met Arg Arg Leu Ile Thr Arg Gly Glu
    850                 855                 860

Trp Gln Ser Glu Thr Gln Asp Thr Met Lys Thr Gly Ser Ser Thr Asn
865                 870                 875                 880

Asn Asn Glu Glu Glu Lys Ser Arg Leu Leu Glu Lys Glu Asn Arg Glu
                885                 890                 895

Leu Glu Lys Ile Ile Ala Glu Lys Glu Glu Arg Val Ser Glu Leu Arg
```

-continued

```
            900                 905                 910

His Gln Leu Gln Ser Arg Gln Gln Leu Arg Ser Arg Arg His Pro Pro
        915                 920                 925

Thr Pro Pro Asp Pro Ser Gly Gly Leu Pro Arg Gly Pro Ser Glu Pro
    930                 935                 940

Pro Asp Arg Leu Ser Cys Asp Gly Ser Arg Val His Leu Leu Tyr Lys
945                 950                 955                 960


<210> SEQ ID NO 46
<211> LENGTH: 2535
<212> TYPE: DNA
<213> ORGANISM: Rattus norvegicus
<220> FEATURE:
<221> NAME/KEY: CDS
<222> LOCATION: (1)...(2532)

<400> SEQUENCE: 46

atg ggc ccg ggg gga ccc tgt acc cca gtg ggg tgg ccg ctg cct ctt       48
Met Gly Pro Gly Gly Pro Cys Thr Pro Val Gly Trp Pro Leu Pro Leu
 1               5                  10                  15

ctg ctg gtg atg gcg gct ggg gtg gct ccg gtg tgg gcc tct cac tcc       96
Leu Leu Val Met Ala Ala Gly Val Ala Pro Val Trp Ala Ser His Ser
            20                  25                  30

cct cat ctc ccg cgg cct cac ccg agg gtc ccc ccg cac ccc tcc tca      144
Pro His Leu Pro Arg Pro His Pro Arg Val Pro Pro His Pro Ser Ser
        35                  40                  45

gaa cgg cgt gca gta tac atc ggg gcg ctg ttt ccc atg agc ggg ggc      192
Glu Arg Arg Ala Val Tyr Ile Gly Ala Leu Phe Pro Met Ser Gly Gly
     50                  55                  60

tgg ccg ggg ggc cag gcc tgc cag ccc gcg gtg gag atg gcg ctg gag      240
Trp Pro Gly Gly Gln Ala Cys Gln Pro Ala Val Glu Met Ala Leu Glu
 65                  70                  75                  80

gac gtt aac agc cgc aga gac atc ctg ccg gac tac gag ctc aag ctt      288
Asp Val Asn Ser Arg Arg Asp Ile Leu Pro Asp Tyr Glu Leu Lys Leu
                 85                  90                  95

atc cac cac gac agc aag tgt gac cca ggg caa gcc acc aag tac ttg      336
Ile His His Asp Ser Lys Cys Asp Pro Gly Gln Ala Thr Lys Tyr Leu
            100                 105                 110

tac gaa cta ctc tac aat gac ccc atc aag atc att ctc atg cct ggc      384
Tyr Glu Leu Leu Tyr Asn Asp Pro Ile Lys Ile Ile Leu Met Pro Gly
        115                 120                 125

tgt agt tct gtc tcc aca ctt gta gct gag gct gcc cgg atg tgg aac      432
Cys Ser Ser Val Ser Thr Leu Val Ala Glu Ala Ala Arg Met Trp Asn
    130                 135                 140

ctt att gtg ctc tca tat ggc tcc agt tca cca gcc ttg tca aac cga      480
Leu Ile Val Leu Ser Tyr Gly Ser Ser Ser Pro Ala Leu Ser Asn Arg
145                 150                 155                 160

cag cgg ttt ccc acg ttc ttc cgg acg cat cca tcc gcc aca ctc cac      528
Gln Arg Phe Pro Thr Phe Phe Arg Thr His Pro Ser Ala Thr Leu His
                165                 170                 175

aat ccc acc cgg gtg aaa ctc ttc gaa aag tgg ggc tgg aag aag atc      576
Asn Pro Thr Arg Val Lys Leu Phe Glu Lys Trp Gly Trp Lys Lys Ile
            180                 185                 190

gct acc atc caa cag acc acc gag gtc ttc acc tca acg ctg gat gac      624
Ala Thr Ile Gln Gln Thr Thr Glu Val Phe Thr Ser Thr Leu Asp Asp
        195                 200                 205

ctg gag gag cga gtg aaa gag gct ggg atc gag atc act ttc cga cag      672
Leu Glu Glu Arg Val Lys Glu Ala Gly Ile Glu Ile Thr Phe Arg Gln
    210                 215                 220

agt ttc ttc tcg gat cca gct gtg cct gtt aaa aac ctg aag cgt caa      720
```

-continued

```
Ser Phe Phe Ser Asp Pro Ala Val Pro Val Lys Asn Leu Lys Arg Gln
225                 230                 235                 240

gat gct cga atc atc gtg gga ctt ttc tat gag acg gaa gcc cgg aaa      768
Asp Ala Arg Ile Ile Val Gly Leu Phe Tyr Glu Thr Glu Ala Arg Lys
                245                 250                 255

gtt ttt tgt gag gtc tat aag gaa agg ctc ttt ggg aag aag tac gtc      816
Val Phe Cys Glu Val Tyr Lys Glu Arg Leu Phe Gly Lys Lys Tyr Val
            260                 265                 270

tgg ttc ctc atc ggg tgg tat gct gac aac tgg ttc aag acc tat gac      864
Trp Phe Leu Ile Gly Trp Tyr Ala Asp Asn Trp Phe Lys Thr Tyr Asp
        275                 280                 285

ccg tca atc aat tgt aca gtg gaa gaa atg acc gag gcg gtg gag ggc      912
Pro Ser Ile Asn Cys Thr Val Glu Glu Met Thr Glu Ala Val Glu Gly
    290                 295                 300

cac atc acc acg gag att gtc atg ctg aac cct gcc aac acc cga agc      960
His Ile Thr Thr Glu Ile Val Met Leu Asn Pro Ala Asn Thr Arg Ser
305                 310                 315                 320

att tcc aac atg acg tca cag gaa ttt gtg gag aaa cta acc aag cgg     1008
Ile Ser Asn Met Thr Ser Gln Glu Phe Val Glu Lys Leu Thr Lys Arg
                325                 330                 335

ctg aaa aga cac ccc gag gag act gga ggc ttc cag gag gca cca ctg     1056
Leu Lys Arg His Pro Glu Glu Thr Gly Gly Phe Gln Glu Ala Pro Leu
            340                 345                 350

gcc tat gat gct atc tgg gcc ttg gct ttg gcc ttg aac aag acg tct     1104
Ala Tyr Asp Ala Ile Trp Ala Leu Ala Leu Ala Leu Asn Lys Thr Ser
        355                 360                 365

gga gga ggt ggt cgt tcc ggc gtg cgc ctg gag gac ttt aac tac aac     1152
Gly Gly Gly Gly Arg Ser Gly Val Arg Leu Glu Asp Phe Asn Tyr Asn
    370                 375                 380

aac cag acc att aca gac cag atc tac cgg gcc atg aac tcc tcc tcc     1200
Asn Gln Thr Ile Thr Asp Gln Ile Tyr Arg Ala Met Asn Ser Ser Ser
385                 390                 395                 400

ttt gag ggc gtt tct ggc cat gtg gtc ttt gat gcc agc ggc tcc cgg     1248
Phe Glu Gly Val Ser Gly His Val Val Phe Asp Ala Ser Gly Ser Arg
                405                 410                 415

atg gca tgg aca ctt atc gag cag cta cag ggc ggc agc tac aag aag     1296
Met Ala Trp Thr Leu Ile Glu Gln Leu Gln Gly Gly Ser Tyr Lys Lys
            420                 425                 430

atc ggc tac tac gac agc acc aag gat gat ctt tcc tgg tcc aaa acg     1344
Ile Gly Tyr Tyr Asp Ser Thr Lys Asp Asp Leu Ser Trp Ser Lys Thr
        435                 440                 445

gac aag tgg att gga ggg tct ccc cca gct gac cag acc ttg gtc atc     1392
Asp Lys Trp Ile Gly Gly Ser Pro Pro Ala Asp Gln Thr Leu Val Ile
    450                 455                 460

aag aca ttc cgt ttc ctg tct cag aaa ctc ttt atc tcc gtc tca gtt     1440
Lys Thr Phe Arg Phe Leu Ser Gln Lys Leu Phe Ile Ser Val Ser Val
465                 470                 475                 480

ctc tcc agc ctg ggc att gtt ctt gct gtt gtc tgt ctg tcc ttt aac     1488
Leu Ser Ser Leu Gly Ile Val Leu Ala Val Val Cys Leu Ser Phe Asn
                485                 490                 495

atc tac aac tcc cac gtt cgt tat atc cag aac tcc cag ccc aac ctg     1536
Ile Tyr Asn Ser His Val Arg Tyr Ile Gln Asn Ser Gln Pro Asn Leu
            500                 505                 510

aac aat ctg act gct gtg ggc tgc tca ctg gca ctg gct gct gtc ttc     1584
Asn Asn Leu Thr Ala Val Gly Cys Ser Leu Ala Leu Ala Ala Val Phe
        515                 520                 525

cct ctc ggg ctg gat ggt tac cac ata ggg aga agc cag ttc ccg ttt     1632
Pro Leu Gly Leu Asp Gly Tyr His Ile Gly Arg Ser Gln Phe Pro Phe
    530                 535                 540
```

-continued

```
gtc tgc cag gcc cgc ctt tgg ctc ttg ggc ttg ggc ttt agt ctg ggc     1680
Val Cys Gln Ala Arg Leu Trp Leu Leu Gly Leu Gly Phe Ser Leu Gly
545                 550                 555                 560

tat ggc tct atg ttc acc aag atc tgg tgg gtc cac aca gtc ttc acg     1728
Tyr Gly Ser Met Phe Thr Lys Ile Trp Trp Val His Thr Val Phe Thr
                565                 570                 575

aag aag gag gag aag aag gag tgg agg aag acc cta gag ccc tgg aaa     1776
Lys Lys Glu Glu Lys Lys Glu Trp Arg Lys Thr Leu Glu Pro Trp Lys
            580                 585                 590

ctc tat gcc act gtg ggc ctg ctg gtg ggc atg gat gtc ctg act ctt     1824
Leu Tyr Ala Thr Val Gly Leu Leu Val Gly Met Asp Val Leu Thr Leu
        595                 600                 605

gcc atc tgg cag att gtg gac ccc ttg cac cga acc att gag act ttt     1872
Ala Ile Trp Gln Ile Val Asp Pro Leu His Arg Thr Ile Glu Thr Phe
    610                 615                 620

gcc aag gag gaa cca aag gaa gac atc gat gtc tcc att ctg ccc cag     1920
Ala Lys Glu Glu Pro Lys Glu Asp Ile Asp Val Ser Ile Leu Pro Gln
625                 630                 635                 640

ttg gag cac tgc agc tcc aag aag atg aat acg tgg ctt ggc att ttc     1968
Leu Glu His Cys Ser Ser Lys Lys Met Asn Thr Trp Leu Gly Ile Phe
                645                 650                 655

tat ggt tac aag ggg ctg ctg ctg ctg ctg gga atc ttt ctt gct tac     2016
Tyr Gly Tyr Lys Gly Leu Leu Leu Leu Leu Gly Ile Phe Leu Ala Tyr
            660                 665                 670

gaa acc aag agc gtg tcc act gaa aag atc aat gac cac agg gcc gtg     2064
Glu Thr Lys Ser Val Ser Thr Glu Lys Ile Asn Asp His Arg Ala Val
        675                 680                 685

ggc atg gct atc tac aat gtc gcg gtc ctg tgt ctc atc act gct cct     2112
Gly Met Ala Ile Tyr Asn Val Ala Val Leu Cys Leu Ile Thr Ala Pro
    690                 695                 700

gtg acc atg atc ctt tcc agt cag cag gac gca gcc ttt gcc ttt gcc     2160
Val Thr Met Ile Leu Ser Ser Gln Gln Asp Ala Ala Phe Ala Phe Ala
705                 710                 715                 720

tct ctg gcc atc gtg ttc tct tcc tac atc act ctg gtt gtg ctc ttt     2208
Ser Leu Ala Ile Val Phe Ser Ser Tyr Ile Thr Leu Val Val Leu Phe
                725                 730                 735

gtg ccc aag atg cgc agg ctg atc acc cga ggg gaa tgg cag tct gaa     2256
Val Pro Lys Met Arg Arg Leu Ile Thr Arg Gly Glu Trp Gln Ser Glu
            740                 745                 750

acg cag gac acc atg aaa aca gga tca tcc acc aac aac aac gag gaa     2304
Thr Gln Asp Thr Met Lys Thr Gly Ser Ser Thr Asn Asn Asn Glu Glu
        755                 760                 765

gag aag tcc cga ctg ttg gag aag gaa aac cga gaa ctg gaa aag atc     2352
Glu Lys Ser Arg Leu Leu Glu Lys Glu Asn Arg Glu Leu Glu Lys Ile
    770                 775                 780

atc gct gag aaa gag gag cgc gtc tct gaa ctg cgc cat cag ctc cag     2400
Ile Ala Glu Lys Glu Glu Arg Val Ser Glu Leu Arg His Gln Leu Gln
785                 790                 795                 800

tct cgg cag caa ctc cgc tca cgg cgc cac ccc cca aca ccc cca gat     2448
Ser Arg Gln Gln Leu Arg Ser Arg Arg His Pro Pro Thr Pro Pro Asp
                805                 810                 815

ccc tct ggg ggc ctt ccc agg gga ccc tct gag ccc cct gac cgg ctt     2496
Pro Ser Gly Gly Leu Pro Arg Gly Pro Ser Glu Pro Pro Asp Arg Leu
            820                 825                 830

agc tgt gat ggg agt cga gta cat ttg ctt tac aag tga                 2535
Ser Cys Asp Gly Ser Arg Val His Leu Leu Tyr Lys
        835                 840
```

<210> SEQ ID NO 47
<211> LENGTH: 844

-continued

<212> TYPE: PRT
<213> ORGANISM: Rattus norvegicus

<400> SEQUENCE: 47

```
Met Gly Pro Gly Gly Pro Cys Thr Pro Val Gly Trp Pro Leu Pro Leu
 1               5                  10                  15

Leu Leu Val Met Ala Ala Gly Val Ala Pro Val Trp Ala Ser His Ser
            20                  25                  30

Pro His Leu Pro Arg Pro His Pro Arg Val Pro Pro His Pro Ser Ser
        35                  40                  45

Glu Arg Arg Ala Val Tyr Ile Gly Ala Leu Phe Pro Met Ser Gly Gly
    50                  55                  60

Trp Pro Gly Gly Gln Ala Cys Gln Pro Ala Val Glu Met Ala Leu Glu
65                  70                  75                  80

Asp Val Asn Ser Arg Arg Asp Ile Leu Pro Asp Tyr Glu Leu Lys Leu
                85                  90                  95

Ile His His Asp Ser Lys Cys Asp Pro Gly Gln Ala Thr Lys Tyr Leu
            100                 105                 110

Tyr Glu Leu Leu Tyr Asn Asp Pro Ile Lys Ile Ile Leu Met Pro Gly
        115                 120                 125

Cys Ser Ser Val Ser Thr Leu Val Ala Glu Ala Ala Arg Met Trp Asn
    130                 135                 140

Leu Ile Val Leu Ser Tyr Gly Ser Ser Ser Pro Ala Leu Ser Asn Arg
145                 150                 155                 160

Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
            180                 185                 190

Ala Thr Ile Gln Gln Thr Thr Glu Val Phe Thr Ser Thr Leu Asp Asp
        195                 200                 205

Leu Glu Glu Arg Val Lys Glu Ala Gly Ile Glu Ile Thr Phe Arg Gln
    210                 215                 220

Ser Phe Phe Ser Asp Pro Ala Val Pro Val Lys Asn Leu Lys Arg Gln
225                 230                 235                 240

Asp Ala Arg Ile Ile Val Gly Leu Phe Tyr Glu Thr Glu Ala Arg Lys
                245                 250                 255

Val Phe Cys Glu Val Tyr Lys Glu Arg Leu Phe Gly Lys Lys Tyr Val
            260                 265                 270

Trp Phe Leu Ile Gly Trp Tyr Ala Asp Asn Trp Phe Lys Thr Tyr Asp
        275                 280                 285

Pro Ser Ile Asn Cys Thr Val Glu Glu Met Thr Glu Ala Val Glu Gly
    290                 295                 300

His Ile Thr Thr Glu Ile Val Met Leu Asn Pro Ala Asn Thr Arg Ser
305                 310                 315                 320

Ile Ser Asn Met Thr Ser Gln Glu Phe Val Glu Lys Leu Thr Lys Arg
                325                 330                 335

Leu Lys Arg His Pro Glu Glu Thr Gly Gly Phe Gln Glu Ala Pro Leu
            340                 345                 350

Ala Tyr Asp Ala Ile Trp Ala Leu Ala Leu Ala Leu Asn Lys Thr Ser
        355                 360                 365

Gly Gly Gly Gly Arg Ser Gly Val Arg Leu Glu Asp Phe Asn Tyr Asn
    370                 375                 380

Asn Gln Thr Ile Thr Asp Gln Ile Tyr Arg Ala Met Asn Ser Ser Ser
385                 390                 395                 400
```

```
Phe Glu Gly Val Ser Gly His Val Val Phe Asp Ala Ser Gly Ser Arg
                405                 410                 415

Met Ala Trp Thr Leu Ile Glu Gln Leu Gln Gly Gly Ser Tyr Lys Lys
            420                 425                 430

Ile Gly Tyr Tyr Asp Ser Thr Lys Asp Asp Leu Ser Trp Ser Lys Thr
        435                 440                 445

Asp Lys Trp Ile Gly Gly Ser Pro Pro Ala Asp Gln Thr Leu Val Ile
    450                 455                 460

Lys Thr Phe Arg Phe Leu Ser Gln Lys Leu Phe Ile Ser Val Ser Val
465                 470                 475                 480

Leu Ser Ser Leu Gly Ile Val Leu Ala Val Val Cys Leu Ser Phe Asn
                485                 490                 495

Ile Tyr Asn Ser His Val Arg Tyr Ile Gln Asn Ser Gln Pro Asn Leu
            500                 505                 510

Asn Asn Leu Thr Ala Val Gly Cys Ser Leu Ala Leu Ala Ala Val Phe
        515                 520                 525

Pro Leu Gly Leu Asp Gly Tyr His Ile Gly Arg Ser Gln Phe Pro Phe
    530                 535                 540

Val Cys Gln Ala Arg Leu Trp Leu Leu Gly Leu Gly Phe Ser Leu Gly
545                 550                 555                 560

Tyr Gly Ser Met Phe Thr Lys Ile Trp Trp Val His Thr Val Phe Thr
                565                 570                 575

Lys Lys Glu Glu Lys Lys Glu Trp Arg Lys Thr Leu Glu Pro Trp Lys
            580                 585                 590

Leu Tyr Ala Thr Val Gly Leu Leu Val Gly Met Asp Val Leu Thr Leu
        595                 600                 605

Ala Ile Trp Gln Ile Val Asp Pro Leu His Arg Thr Ile Glu Thr Phe
    610                 615                 620

Ala Lys Glu Glu Pro Lys Glu Asp Ile Asp Val Ser Ile Leu Pro Gln
625                 630                 635                 640

Leu Glu His Cys Ser Ser Lys Lys Met Asn Thr Trp Leu Gly Ile Phe
                645                 650                 655

Tyr Gly Tyr Lys Gly Leu Leu Leu Leu Leu Gly Ile Phe Leu Ala Tyr
            660                 665                 670

Glu Thr Lys Ser Val Ser Thr Glu Lys Ile Asn Asp His Arg Ala Val
        675                 680                 685

Gly Met Ala Ile Tyr Asn Val Ala Val Leu Cys Leu Ile Thr Ala Pro
    690                 695                 700

Val Thr Met Ile Leu Ser Ser Gln Gln Asp Ala Ala Phe Ala Phe Ala
705                 710                 715                 720

Ser Leu Ala Ile Val Phe Ser Ser Tyr Ile Thr Leu Val Val Leu Phe
                725                 730                 735

Val Pro Lys Met Arg Arg Leu Ile Thr Arg Gly Glu Trp Gln Ser Glu
            740                 745                 750

Thr Gln Asp Thr Met Lys Thr Gly Ser Ser Thr Asn Asn Asn Glu Glu
        755                 760                 765

Glu Lys Ser Arg Leu Leu Glu Lys Glu Asn Arg Glu Leu Glu Lys Ile
    770                 775                 780

Ile Ala Glu Lys Glu Glu Arg Val Ser Glu Leu Arg His Gln Leu Gln
785                 790                 795                 800

Ser Arg Gln Gln Leu Arg Ser Arg Arg His Pro Pro Thr Pro Pro Asp
                805                 810                 815
```

-continued

```
Pro Ser Gly Gly Leu Pro Arg Gly Pro Ser Glu Pro Pro Asp Arg Leu
            820                 825                 830

Ser Cys Asp Gly Ser Arg Val His Leu Leu Tyr Lys
        835                 840


<210> SEQ ID NO 48
<211> LENGTH: 2886
<212> TYPE: DNA
<213> ORGANISM: Homo sapiens
<220> FEATURE:
<221> NAME/KEY: CDS
<222> LOCATION: (1)...(2883)

<400> SEQUENCE: 48

atg ttg ctg ctg ctg cta ctg gcg cca ctc ttc ctc cgc ccc ccg ggc      48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc      96
Ala Gly Gly Ala Gln Thr Pro Asn Ala Thr Ser Glu Gly Cys Gln Ile
            20                  25                  30

ata cac ccg ccc tgg gaa ggg ggc atc agg tac cgg ggc ctg act cgg     144
Ile His Pro Pro Trp Glu Gly Gly Ile Arg Tyr Arg Gly Leu Thr Arg
        35                  40                  45

gac cag gtg aag gct atc aac ttc ctg cca gtg gac tat gag att gag     192
Asp Gln Val Lys Ala Ile Asn Phe Leu Pro Val Asp Tyr Glu Ile Glu
    50                  55                  60

tat gtg tgc cgg ggg gag cgc gag gtg gtg ggg ccc aag gtc cgc aag     240
Tyr Val Cys Arg Gly Glu Arg Glu Val Val Gly Pro Lys Val Arg Lys
 65                 70                  75                  80

tgc ctg gcc aac ggc tcc tgg aca gat atg gac aca ccc agc cgc tgt     288
Cys Leu Ala Asn Gly Ser Trp Thr Asp Met Asp Thr Pro Ser Arg Cys
                85                  90                  95

gtc cga atc tgc tcc aag tct tat ttg acc ctg gaa aat ggg aag gtt     336
Val Arg Ile Cys Ser Lys Ser Tyr Leu Thr Leu Glu Asn Gly Lys Val
            100                 105                 110

ttc ctg acg ggt ggg gac ctc cca gct ctg gac gga gcc cgg gtg gat     384
Phe Leu Thr Gly Gly Asp Leu Pro Ala Leu Asp Gly Ala Arg Val Asp
        115                 120                 125

ttc cgg tgt gac ccc gac ttc cat ctg gtg ggc agc tcc cgg agc atc     432
Phe Arg Cys Asp Pro Asp Phe His Leu Val Gly Ser Ser Arg Ser Ile
    130                 135                 140

tgt agt cag ggc cag tgg agc acc ccc aag ccc cac tgc cag gtg aat     480
Cys Ser Gln Gly Gln Trp Ser Thr Pro Lys Pro His Cys Gln Val Asn
145                 150                 155                 160

cga acg cca cac tca gaa cgg cgc gca gtg tac atc ggg gca ctg ttt     528
Arg Thr Pro His Ser Glu Arg Arg Ala Val Tyr Ile Gly Ala Leu Phe
                165                 170                 175

ccc atg agc ggg ggc tgg cca ggg ggc cag gcc tgc cag ccc gcg gtg     576
Pro Met Ser Gly Gly Trp Pro Gly Gly Gln Ala Cys Gln Pro Ala Val
            180                 185                 190

gag atg gcg ctg gag gac gtg aat agc cgc agg gac atc ctg ccg gac     624
Glu Met Ala Leu Glu Asp Val Asn Ser Arg Arg Asp Ile Leu Pro Asp
        195                 200                 205

tat gag ctc aag ctc atc cac cac gac agc aag tgt gat cca ggc caa     672
Tyr Glu Leu Lys Leu Ile His His Asp Ser Lys Cys Asp Pro Gly Gln
    210                 215                 220

gcc acc aag tac cta tat gag ctg ctc tac aac gac cct atc aag atc     720
Ala Thr Lys Tyr Leu Tyr Glu Leu Leu Tyr Asn Asp Pro Ile Lys Ile
225                 230                 235                 240

atc ctt atg cct ggc tgc agc tct gtc tcc acg ctg gtg gct gag gct     768
Ile Leu Met Pro Gly Cys Ser Ser Val Ser Thr Leu Val Ala Glu Ala
```

-continued

```
                245                 250                 255

gct agg atg tgg aac ctc att gtg ctt tcc tat ggc tcc agc tca cca      816
Ala Arg Met Trp Asn Leu Ile Val Leu Ser Tyr Gly Ser Ser Ser Pro
            260                 265                 270

gcc ctg tca aac cgg cag cgt ttc ccc act ttc ttc cga acg cac cca      864
Ala Leu Ser Asn Arg Gln Arg Phe Pro Thr Phe Phe Arg Thr His Pro
        275                 280                 285

tca gcc aca ctc cac aac cct acc cgc gtg aaa ctc ttt gaa aag tgg      912
Ser Ala Thr Leu His Asn Pro Thr Arg Val Lys Leu Phe Glu Lys Trp
    290                 295                 300

ggc tgg aag aag att gct acc atc cag cag acc act gag gtc ttc act      960
Gly Trp Lys Lys Ile Ala Thr Ile Gln Gln Thr Thr Glu Val Phe Thr
305                 310                 315                 320

tcg act ctg gac gac ctg gag gaa cga gtg aag gag gct gga att gag     1008
Ser Thr Leu Asp Asp Leu Glu Glu Arg Val Lys Glu Ala Gly Ile Glu
                325                 330                 335

att act ttc cgc cag agt ttc ttc tca gat cca gct gtg ccc gtc aaa     1056
Ile Thr Phe Arg Gln Ser Phe Phe Ser Asp Pro Ala Val Pro Val Lys
            340                 345                 350

aac ctg aag cgc cag gat gcc cga atc atc gtg gga ctt ttc tat gag     1104
Asn Leu Lys Arg Gln Asp Ala Arg Ile Ile Val Gly Leu Phe Tyr Glu
        355                 360                 365

act gaa gcc cgg aaa gtt ttt tgt gag gtg tac aag gag cgt ctc ttt     1152
Thr Glu Ala Arg Lys Val Phe Cys Glu Val Tyr Lys Glu Arg Leu Phe
    370                 375                 380

ggg aag aag tac gtc tgg ttc ctc att ggg tgg tat gct gac aat tgg     1200
Gly Lys Lys Tyr Val Trp Phe Leu Ile Gly Trp Tyr Ala Asp Asn Trp
385                 390                 395                 400

ttc aag atc tac gac cct tct atc aac tgc aca gtg gat gag atg act     1248
Phe Lys Ile Tyr Asp Pro Ser Ile Asn Cys Thr Val Asp Glu Met Thr
                405                 410                 415

gag gcg gtg gag ggc cac atc aca act gag att gtc atg ctg aat cct     1296
Glu Ala Val Glu Gly His Ile Thr Thr Glu Ile Val Met Leu Asn Pro
            420                 425                 430

gcc aat acc cgc agc att tcc aac atg aca tcc cag gaa ttt gtg gag     1344
Ala Asn Thr Arg Ser Ile Ser Asn Met Thr Ser Gln Glu Phe Val Glu
        435                 440                 445

aaa cta acc aag cga ctg aaa aga cac cct gag gag aca gga ggc ttc     1392
Lys Leu Thr Lys Arg Leu Lys Arg His Pro Glu Glu Thr Gly Gly Phe
    450                 455                 460

cag gag gca ccg ctg gcc tat gat gcc atc tgg gcc ttg gca ctg gcc     1440
Gln Glu Ala Pro Leu Ala Tyr Asp Ala Ile Trp Ala Leu Ala Leu Ala
465                 470                 475                 480

ctg aac aag aca tct gga gga ggc ggc cgt tct ggt gtg cgc ctg gag     1488
Leu Asn Lys Thr Ser Gly Gly Gly Gly Arg Ser Gly Val Arg Leu Glu
                485                 490                 495

gac ttc aac tac aac aac cag acc att acc gac caa atc tac cgg gca     1536
Asp Phe Asn Tyr Asn Asn Gln Thr Ile Thr Asp Gln Ile Tyr Arg Ala
            500                 505                 510

atg aac tct tcg tcc ttt gag ggt gtc tct ggc cat gtg gtg ttt gat     1584
Met Asn Ser Ser Ser Phe Glu Gly Val Ser Gly His Val Val Phe Asp
        515                 520                 525

gcc agc ggc tct cgg atg gca tgg acg ctt atc gag cag ctt cag ggt     1632
Ala Ser Gly Ser Arg Met Ala Trp Thr Leu Ile Glu Gln Leu Gln Gly
    530                 535                 540

ggc agc tac aag aag att ggc tac tat gac agc acc aag gat gat ctt     1680
Gly Ser Tyr Lys Lys Ile Gly Tyr Tyr Asp Ser Thr Lys Asp Asp Leu
545                 550                 555                 560

tcc tgg tcc aaa aca gat aaa tgg att gga ggg tcc ccc cca gct gac     1728
```

-continued

```
Ser Trp Ser Lys Thr Asp Lys Trp Ile Gly Gly Ser Pro Pro Ala Asp
                565                 570                 575

cag acc ctg gtc atc aag aca ttc cgc ttc ctg tca cag aaa ctc ttt      1776
Gln Thr Leu Val Ile Lys Thr Phe Arg Phe Leu Ser Gln Lys Leu Phe
            580                 585                 590

atc tcc gtc tca gtt ctc tcc agc ctg ggc att gtc cta gct gtt gtc      1824
Ile Ser Val Ser Val Leu Ser Ser Leu Gly Ile Val Leu Ala Val Val
        595                 600                 605

tgt ctg tcc ttt aac atc tac aac tca cat gtc cgt tat atc cag aac      1872
Cys Leu Ser Phe Asn Ile Tyr Asn Ser His Val Arg Tyr Ile Gln Asn
    610                 615                 620

tca cag ccc aac ctg aac aac ctg act gct gtg ggc tgc tca ctg gct      1920
Ser Gln Pro Asn Leu Asn Asn Leu Thr Ala Val Gly Cys Ser Leu Ala
625                 630                 635                 640

tta gct gct gtc ttc ccc ctg ggg ctc gat ggt tac cac att ggg agg      1968
Leu Ala Ala Val Phe Pro Leu Gly Leu Asp Gly Tyr His Ile Gly Arg
                645                 650                 655

aac cag ttt cct ttc gtc tgc cag gcc cgc ctc tgg ctc ctg ggc ctg      2016
Asn Gln Phe Pro Phe Val Cys Gln Ala Arg Leu Trp Leu Leu Gly Leu
            660                 665                 670

ggc ttt agt ctg ggc tac ggt tcc atg ttc acc aag att tgg tgg gtc      2064
Gly Phe Ser Leu Gly Tyr Gly Ser Met Phe Thr Lys Ile Trp Trp Val
        675                 680                 685

cac acg gtc ttc aca aag aag gaa gaa aag aag gag tgg agg aag act      2112
His Thr Val Phe Thr Lys Lys Glu Glu Lys Lys Glu Trp Arg Lys Thr
    690                 695                 700

ctg gaa ccc tgg aag ctg tat gcc aca gtg ggc ctg ctg gtg ggc atg      2160
Leu Glu Pro Trp Lys Leu Tyr Ala Thr Val Gly Leu Leu Val Gly Met
705                 710                 715                 720

gat gtc ctc act ctc gcc atc tgg cag atc gtg gac cct ctg cac cgg      2208
Asp Val Leu Thr Leu Ala Ile Trp Gln Ile Val Asp Pro Leu His Arg
                725                 730                 735

acc att gag aca ttt gcc aag gag gaa cct aag gaa gat att gac gtc      2256
Thr Ile Glu Thr Phe Ala Lys Glu Glu Pro Lys Glu Asp Ile Asp Val
            740                 745                 750

tct att ctg ccc cag ctg gag cat tgc agc tcc agg aag atg aat aca      2304
Ser Ile Leu Pro Gln Leu Glu His Cys Ser Ser Arg Lys Met Asn Thr
        755                 760                 765

tgg ctt ggc att ttc tat ggt tac aag ggg ctg ctg ctg ctg ctg gga      2352
Trp Leu Gly Ile Phe Tyr Gly Tyr Lys Gly Leu Leu Leu Leu Leu Gly
    770                 775                 780

atc ttc ctt gct tat gag acc aag agt gtg tcc act gag aag atc aat      2400
Ile Phe Leu Ala Tyr Glu Thr Lys Ser Val Ser Thr Glu Lys Ile Asn
785                 790                 795                 800

gat cac cgg gct gtg ggc atg gct atc tac aat gtg gca gtc ctg tgc      2448
Asp His Arg Ala Val Gly Met Ala Ile Tyr Asn Val Ala Val Leu Cys
                805                 810                 815

ctc atc act gct cct gtc acc atg att ctg tcc agc cag cag gat gca      2496
Leu Ile Thr Ala Pro Val Thr Met Ile Leu Ser Ser Gln Gln Asp Ala
            820                 825                 830

gcc ttt gcc ttt gcc tct ctt gcc ata gtt ttc tcc tcc tat atc act      2544
Ala Phe Ala Phe Ala Ser Leu Ala Ile Val Phe Ser Ser Tyr Ile Thr
        835                 840                 845

ctt gtt gtg ctc ttt gtg ccc aag atg cgc agg ctg atc acc cga ggg      2592
Leu Val Val Leu Phe Val Pro Lys Met Arg Arg Leu Ile Thr Arg Gly
    850                 855                 860

gaa tgg cag tcg gag gcg cag gac acc atg aag aca ggg tca tcg acc      2640
Glu Trp Gln Ser Glu Ala Gln Asp Thr Met Lys Thr Gly Ser Ser Thr
865                 870                 875                 880
```

-continued

```
aac aac aac gag gag gag aag tcc cgg ctg ttg gag aag gag aac cgt      2688
Asn Asn Asn Glu Glu Glu Lys Ser Arg Leu Leu Glu Lys Glu Asn Arg
                885                 890                 895

gaa ctg gaa aag atc att gct gag aaa gag gag cgt gtc tct gaa ctg      2736
Glu Leu Glu Lys Ile Ile Ala Glu Lys Glu Glu Arg Val Ser Glu Leu
            900                 905                 910

cgc cat caa ctc cag tct cgg cag cag ctc cgc tcc cgg cgc cac cca      2784
Arg His Gln Leu Gln Ser Arg Gln Gln Leu Arg Ser Arg Arg His Pro
        915                 920                 925

ccg aca ccc cca gaa ccc tct ggg ggc ctg ccc agg gga ccc cct gag      2832
Pro Thr Pro Pro Glu Pro Ser Gly Gly Leu Pro Arg Gly Pro Pro Glu
    930                 935                 940

ccc ccc gac cgg ctt agc tgt gat ggg agt cga gtg cat ttg ctt tat      2880
Pro Pro Asp Arg Leu Ser Cys Asp Gly Ser Arg Val His Leu Leu Tyr
945                 950                 955                 960

aag tga                                                              2886
Lys


<210> SEQ ID NO 49
<211> LENGTH: 961
<212> TYPE: PRT
<213> ORGANISM: Homo sapiens

<400> SEQUENCE: 49

Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Val Gly Ser Ser Arg Ser Ile
    130                 135                 140

Cys Ser Gln Gly Gln Trp Ser Thr Pro Lys Pro His Cys Gln Val Asn
145                 150                 155                 160

Arg Thr Pro His Ser Glu Arg Arg Ala Val Tyr Ile Gly Ala Leu Phe
                165                 170                 175

Pro Met Ser Gly Gly Trp Pro Gly Gly Gln Ala Cys Gln Pro Ala Val
            180                 185                 190

Glu Met Ala Leu Glu Asp Val Asn Ser Arg Arg Asp Ile Leu Pro Asp
        195                 200                 205

Tyr Glu Leu Lys Leu Ile His His Asp Ser Lys Cys Asp Pro Gly Gln
    210                 215                 220

Ala Thr Lys Tyr Leu Tyr Glu Leu Leu Tyr Asn Asp Pro Ile Lys Ile
225                 230                 235                 240

Ile Leu Met Pro Gly Cys Ser Ser Val Ser Thr Leu Val Ala Glu Ala
                245                 250                 255
```

-continued

```
Ala Arg Met Trp Asn Leu Ile Val Leu Ser Tyr Gly Ser Ser Ser Pro
            260                 265                 270

Ala Leu Ser Asn Arg Gln Arg Phe Pro Thr Phe Phe Arg Thr His Pro
        275                 280                 285

Ser Ala Thr Leu His Asn Pro Thr Arg Val Lys Leu Phe Glu Lys Trp
    290                 295                 300

Gly Trp Lys Lys Ile Ala Thr Ile Gln Gln Thr Thr Glu Val Phe Thr
305                 310                 315                 320

Ser Thr Leu Asp Asp Leu Glu Glu Arg Val Lys Glu Ala Gly Ile Glu
                325                 330                 335

Ile Thr Phe Arg Gln Ser Phe Phe Ser Asp Pro Ala Val Pro Val Lys
            340                 345                 350

Asn Leu Lys Arg Gln Asp Ala Arg Ile Ile Val Gly Leu Phe Tyr Glu
        355                 360                 365

Thr Glu Ala Arg Lys Val Phe Cys Glu Val Tyr Lys Glu Arg Leu Phe
    370                 375                 380

Gly Lys Lys Tyr Val Trp Phe Leu Ile Gly Trp Tyr Ala Asp Asn Trp
385                 390                 395                 400

Phe Lys Ile Tyr Asp Pro Ser Ile Asn Cys Thr Val Asp Glu Met Thr
                405                 410                 415

Glu Ala Val Glu Gly His Ile Thr Thr Glu Ile Val Met Leu Asn Pro
            420                 425                 430

Ala Asn Thr Arg Ser Ile Ser Asn Met Thr Ser Gln Glu Phe Val Glu
        435                 440                 445

Lys Leu Thr Lys Arg Leu Lys Arg His Pro Glu Glu Thr Gly Gly Phe
    450                 455                 460

Gln Glu Ala Pro Leu Ala Tyr Asp Ala Ile Trp Ala Leu Ala Leu Ala
465                 470                 475                 480

Leu Asn Lys Thr Ser Gly Gly Gly Gly Arg Ser Gly Val Arg Leu Glu
                485                 490                 495

Asp Phe Asn Tyr Asn Asn Gln Thr Ile Thr Asp Gln Ile Tyr Arg Ala
            500                 505                 510

Met Asn Ser Ser Ser Phe Glu Gly Val Ser Gly His Val Val Phe Asp
        515                 520                 525

Ala Ser Gly Ser Arg Met Ala Trp Thr Leu Ile Glu Gln Leu Gln Gly
    530                 535                 540

Gly Ser Tyr Lys Lys Ile Gly Tyr Tyr Asp Ser Thr Lys Asp Asp Leu
545                 550                 555                 560

Ser Trp Ser Lys Thr Asp Lys Trp Ile Gly Gly Ser Pro Pro Ala Asp
                565                 570                 575

Gln Thr Leu Val Ile Lys Thr Phe Arg Phe Leu Ser Gln Lys Leu Phe
            580                 585                 590

Ile Ser Val Ser Val Leu Ser Ser Leu Gly Ile Val Leu Ala Val Val
        595                 600                 605

Cys Leu Ser Phe Asn Ile Tyr Asn Ser His Val Arg Tyr Ile Gln Asn
    610                 615                 620

Ser Gln Pro Asn Leu Asn Asn Leu Thr Ala Val Gly Cys Ser Leu Ala
625                 630                 635                 640

Leu Ala Ala Val Phe Pro Leu Gly Leu Asp Gly Tyr His Ile Gly Arg
                645                 650                 655

Asn Gln Phe Pro Phe Val Cys Gln Ala Arg Leu Trp Leu Leu Gly Leu
            660                 665                 670

Gly Phe Ser Leu Gly Tyr Gly Ser Met Phe Thr Lys Ile Trp Trp Val
```

```
        675                 680                 685

His Thr Val Phe Thr Lys Lys Glu Glu Lys Lys Glu Trp Arg Lys Thr
    690                 695                 700

Leu Glu Pro Trp Lys Leu Tyr Ala Thr Val Gly Leu Leu Val Gly Met
705                 710                 715                 720

Asp Val Leu Thr Leu Ala Ile Trp Gln Ile Val Asp Pro Leu His Arg
                725                 730                 735

Thr Ile Glu Thr Phe Ala Lys Glu Glu Pro Lys Glu Asp Ile Asp Val
            740                 745                 750

Ser Ile Leu Pro Gln Leu Glu His Cys Ser Ser Arg Lys Met Asn Thr
        755                 760                 765

Trp Leu Gly Ile Phe Tyr Gly Tyr Lys Gly Leu Leu Leu Leu Leu Gly
    770                 775                 780

Ile Phe Leu Ala Tyr Glu Thr Lys Ser Val Ser Thr Glu Lys Ile Asn
785                 790                 795                 800

Asp His Arg Ala Val Gly Met Ala Ile Tyr Asn Val Ala Val Leu Cys
                805                 810                 815

Leu Ile Thr Ala Pro Val Thr Met Ile Leu Ser Ser Gln Gln Asp Ala
            820                 825                 830

Ala Phe Ala Phe Ala Ser Leu Ala Ile Val Phe Ser Ser Tyr Ile Thr
        835                 840                 845

Leu Val Val Leu Phe Val Pro Lys Met Arg Arg Leu Ile Thr Arg Gly
    850                 855                 860

Glu Trp Gln Ser Glu Ala Gln Asp Thr Met Lys Thr Gly Ser Ser Thr
865                 870                 875                 880

Asn Asn Asn Glu Glu Glu Lys Ser Arg Leu Leu Glu Lys Glu Asn Arg
                885                 890                 895

Glu Leu Glu Lys Ile Ile Ala Glu Lys Glu Glu Arg Val Ser Glu Leu
            900                 905                 910

Arg His Gln Leu Gln Ser Arg Gln Gln Leu Arg Ser Arg Arg His Pro
        915                 920                 925

Pro Thr Pro Pro Glu Pro Ser Gly Gly Leu Pro Arg Gly Pro Pro Glu
    930                 935                 940

Pro Pro Asp Arg Leu Ser Cys Asp Gly Ser Arg Val His Leu Leu Tyr
945                 950                 955                 960

Lys


<210> SEQ ID NO 50
<211> LENGTH: 2535
<212> TYPE: DNA
<213> ORGANISM: Homo sapiens
<220> FEATURE:
<221> NAME/KEY: CDS
<222> LOCATION: (1)...(2532)

<400> SEQUENCE: 50

atg ggg ccc ggg gcc cct ttt gcc cgg gtg ggg tgg cca ctg ccg ctt       48
Met Gly Pro Gly Ala Pro Phe Ala Arg Val Gly Trp Pro Leu Pro Leu
 1               5                  10                  15

ctg gtt gtg atg gcg gca ggg gtg gct ccg gtg tgg gcc tcc cac tcc       96
Leu Val Val Met Ala Ala Gly Val Ala Pro Val Trp Ala Ser His Ser
            20                  25                  30

ccc cat ctc ccg cgg cct cac tcg cgg gtc ccc ccg cac ccc tcc tca      144
Pro His Leu Pro Arg Pro His Ser Arg Val Pro Pro His Pro Ser Ser
        35                  40                  45

gaa cgg cgc gca gtg tac atc ggg gca ctg ttt ccc atg agc ggg ggc      192
```

-continued

```
Glu Arg Arg Ala Val Tyr Ile Gly Ala Leu Phe Pro Met Ser Gly Gly
     50                  55                  60

tgg cca ggg ggc cag gcc tgc cag ccc gcg gtg gag atg gcg ctg gag      240
Trp Pro Gly Gly Gln Ala Cys Gln Pro Ala Val Glu Met Ala Leu Glu
 65                  70                  75                  80

gac gtg aat agc cgc agg gac atc ctg ccg gac tat gag ctc aag ctc      288
Asp Val Asn Ser Arg Arg Asp Ile Leu Pro Asp Tyr Glu Leu Lys Leu
                 85                  90                  95

atc cac cac gac agc aag tgt gat cca ggc caa gcc acc aag tac cta      336
Ile His His Asp Ser Lys Cys Asp Pro Gly Gln Ala Thr Lys Tyr Leu
            100                 105                 110

tat gag ctg ctc tac aac gac cct atc aag atc atc ctt atg cct ggc      384
Tyr Glu Leu Leu Tyr Asn Asp Pro Ile Lys Ile Ile Leu Met Pro Gly
        115                 120                 125

tgc agc tct gtc tcc acg ctg gtg gct gag gct gct agg atg tgg aac      432
Cys Ser Ser Val Ser Thr Leu Val Ala Glu Ala Ala Arg Met Trp Asn
    130                 135                 140

ctc att gtg ctt tcc tat ggc tcc agc tca cca gcc ctg tca aac cgg      480
Leu Ile Val Leu Ser Tyr Gly Ser Ser Ser Pro Ala Leu Ser Asn Arg
145                 150                 155                 160

cag cgt ttc ccc act ttc ttc cga acg cac cca tca gcc aca ctc cac      528
Gln Arg Phe Pro Thr Phe Phe Arg Thr His Pro Ser Ala Thr Leu His
                165                 170                 175

aac cct acc cgc gtg aaa ctc ttt gaa aag tgg ggc tgg aag aag att      576
Asn Pro Thr Arg Val Lys Leu Phe Glu Lys Trp Gly Trp Lys Lys Ile
            180                 185                 190

gct acc atc cag cag acc act gag gtc ttc act tcg act ctg gac gac      624
Ala Thr Ile Gln Gln Thr Thr Glu Val Phe Thr Ser Thr Leu Asp Asp
        195                 200                 205

ctg gag gaa cga gtg aag gag gct gga att gag att act ttc cgc cag      672
Leu Glu Glu Arg Val Lys Glu Ala Gly Ile Glu Ile Thr Phe Arg Gln
    210                 215                 220

agt ttc ttc tca gat cca gct gtg ccc gtc aaa aac ctg aag cgc cag      720
Ser Phe Phe Ser Asp Pro Ala Val Pro Val Lys Asn Leu Lys Arg Gln
225                 230                 235                 240

gat gcc cga atc atc gtg gga ctt ttc tat gag act gaa gcc cgg aaa      768
Asp Ala Arg Ile Ile Val Gly Leu Phe Tyr Glu Thr Glu Ala Arg Lys
                245                 250                 255

gtt ttt tgt gag gtg tac aag gag cgt ctc ttt ggg aag aag tac gtc      816
Val Phe Cys Glu Val Tyr Lys Glu Arg Leu Phe Gly Lys Lys Tyr Val
            260                 265                 270

tgg ttc ctc att ggg tgg tat gct gac aat tgg ttc aag atc tac gac      864
Trp Phe Leu Ile Gly Trp Tyr Ala Asp Asn Trp Phe Lys Ile Tyr Asp
        275                 280                 285

cct tct atc aac tgc aca gtg gat gag atg act gag gcg gtg gag ggc      912
Pro Ser Ile Asn Cys Thr Val Asp Glu Met Thr Glu Ala Val Glu Gly
    290                 295                 300

cac atc aca act gag att gtc atg ctg aat cct gcc aat acc cgc agc      960
His Ile Thr Thr Glu Ile Val Met Leu Asn Pro Ala Asn Thr Arg Ser
305                 310                 315                 320

att tcc aac atg aca tcc cag gaa ttt gtg gag aaa cta acc aag cga     1008
Ile Ser Asn Met Thr Ser Gln Glu Phe Val Glu Lys Leu Thr Lys Arg
                325                 330                 335

ctg aaa aga cac cct gag gag aca gga ggc ttc cag gag gca ccg ctg     1056
Leu Lys Arg His Pro Glu Glu Thr Gly Gly Phe Gln Glu Ala Pro Leu
            340                 345                 350

gcc tat gat gcc atc tgg gcc ttg gca ctg gcc ctg aac aag aca tct     1104
Ala Tyr Asp Ala Ile Trp Ala Leu Ala Leu Ala Leu Asn Lys Thr Ser
        355                 360                 365
```

-continued

```
gga gga ggc ggc cgt tct ggt gtg cgc ctg gag gac ttc aac tac aac     1152
Gly Gly Gly Gly Arg Ser Gly Val Arg Leu Glu Asp Phe Asn Tyr Asn
    370                 375                 380

aac cag acc att acc gac caa atc tac cgg gca atg aac tct tcg tcc     1200
Asn Gln Thr Ile Thr Asp Gln Ile Tyr Arg Ala Met Asn Ser Ser Ser
385                 390                 395                 400

ttt gag ggt gtc tct ggc cat gtg gtg ttt gat gcc agc ggc tct cgg     1248
Phe Glu Gly Val Ser Gly His Val Val Phe Asp Ala Ser Gly Ser Arg
                405                 410                 415

atg gca tgg acg ctt atc gag cag ctt cag ggt ggc agc tac aag aag     1296
Met Ala Trp Thr Leu Ile Glu Gln Leu Gln Gly Gly Ser Tyr Lys Lys
            420                 425                 430

att ggc tac tat gac agc acc aag gat gat ctt tcc tgg tcc aaa aca     1344
Ile Gly Tyr Tyr Asp Ser Thr Lys Asp Asp Leu Ser Trp Ser Lys Thr
        435                 440                 445

gat aaa tgg att gga ggg tcc ccc cca gct gac cag acc ctg gtc atc     1392
Asp Lys Trp Ile Gly Gly Ser Pro Pro Ala Asp Gln Thr Leu Val Ile
    450                 455                 460

aag aca ttc cgc ttc ctg tca cag aaa ctc ttt atc tcc gtc tca gtt     1440
Lys Thr Phe Arg Phe Leu Ser Gln Lys Leu Phe Ile Ser Val Ser Val
465                 470                 475                 480

ctc tcc agc ctg ggc att gtc cta gct gtt gtc tgt ctg tcc ttt aac     1488
Leu Ser Ser Leu Gly Ile Val Leu Ala Val Val Cys Leu Ser Phe Asn
                485                 490                 495

atc tac aac tca cat gtc cgt tat atc cag aac tca cag ccc aac ctg     1536
Ile Tyr Asn Ser His Val Arg Tyr Ile Gln Asn Ser Gln Pro Asn Leu
            500                 505                 510

aac aac ctg act gct gtg ggc tgc tca ctg gct tta gct gct gtc ttc     1584
Asn Asn Leu Thr Ala Val Gly Cys Ser Leu Ala Leu Ala Ala Val Phe
        515                 520                 525

ccc ctg ggg ctc gat ggt tac cac att ggg agg aac cag ttt cct ttc     1632
Pro Leu Gly Leu Asp Gly Tyr His Ile Gly Arg Asn Gln Phe Pro Phe
    530                 535                 540

gtc tgc cag gcc cgc ctc tgg ctc ctg ggc ctg ggc ttt agt ctg ggc     1680
Val Cys Gln Ala Arg Leu Trp Leu Leu Gly Leu Gly Phe Ser Leu Gly
545                 550                 555                 560

tac ggt tcc atg ttc acc aag att tgg tgg gtc cac acg gtc ttc aca     1728
Tyr Gly Ser Met Phe Thr Lys Ile Trp Trp Val His Thr Val Phe Thr
                565                 570                 575

aag aag gaa gaa aag aag gag tgg agg aag act ctg gaa ccc tgg aag     1776
Lys Lys Glu Glu Lys Lys Glu Trp Arg Lys Thr Leu Glu Pro Trp Lys
            580                 585                 590

ctg tat gcc aca gtg ggc ctg ctg gtg ggc atg gat gtc ctc act ctc     1824
Leu Tyr Ala Thr Val Gly Leu Leu Val Gly Met Asp Val Leu Thr Leu
        595                 600                 605

gcc atc tgg cag atc gtg gac cct ctg cac cgg acc att gag aca ttt     1872
Ala Ile Trp Gln Ile Val Asp Pro Leu His Arg Thr Ile Glu Thr Phe
    610                 615                 620

gcc aag gag gaa cct aag gaa gat att gac gtc tct att ctg ccc cag     1920
Ala Lys Glu Glu Pro Lys Glu Asp Ile Asp Val Ser Ile Leu Pro Gln
625                 630                 635                 640

ctg gag cat tgc agc tcc agg aag atg aat aca tgg ctt ggc att ttc     1968
Leu Glu His Cys Ser Ser Arg Lys Met Asn Thr Trp Leu Gly Ile Phe
                645                 650                 655

tat ggt tac aag ggg ctg ctg ctg ctg ctg gga atc ttc ctt gct tat     2016
Tyr Gly Tyr Lys Gly Leu Leu Leu Leu Leu Gly Ile Phe Leu Ala Tyr
            660                 665                 670

gag acc aag agt gtg tcc act gag aag atc aat gat cac cgg gct gtg     2064
Glu Thr Lys Ser Val Ser Thr Glu Lys Ile Asn Asp His Arg Ala Val
        675                 680                 685
```

-continued

```
ggc atg gct atc tac aat gtg gca gtc ctg tgc ctc atc act gct cct     2112
Gly Met Ala Ile Tyr Asn Val Ala Val Leu Cys Leu Ile Thr Ala Pro
    690                 695                 700

gtc acc atg att ctg tcc agc cag cag gat gca gcc ttt gcc ttt gcc     2160
Val Thr Met Ile Leu Ser Ser Gln Gln Asp Ala Ala Phe Ala Phe Ala
705                 710                 715                 720

tct ctt gcc ata gtt ttc tcc tcc tat atc act ctt gtt gtg ctc ttt     2208
Ser Leu Ala Ile Val Phe Ser Ser Tyr Ile Thr Leu Val Val Leu Phe
                725                 730                 735

gtg ccc aag atg cgc agg ctg atc acc cga ggg gaa tgg cag tcg gag     2256
Val Pro Lys Met Arg Arg Leu Ile Thr Arg Gly Glu Trp Gln Ser Glu
            740                 745                 750

gcg cag gac acc atg aag aca ggg tca tcg acc aac aac aac gag gag     2304
Ala Gln Asp Thr Met Lys Thr Gly Ser Ser Thr Asn Asn Asn Glu Glu
        755                 760                 765

gag aag tcc cgg ctg ttg gag aag gag aac cgt gaa ctg gaa aag atc     2352
Glu Lys Ser Arg Leu Leu Glu Lys Glu Asn Arg Glu Leu Glu Lys Ile
    770                 775                 780

att gct gag aaa gag gag cgt gtc tct gaa ctg cgc cat caa ctc cag     2400
Ile Ala Glu Lys Glu Glu Arg Val Ser Glu Leu Arg His Gln Leu Gln
785                 790                 795                 800

tct cgg cag cag ctc cgc tcc cgg cgc cac cca ccg aca ccc cca gaa     2448
Ser Arg Gln Gln Leu Arg Ser Arg Arg His Pro Pro Thr Pro Pro Glu
                805                 810                 815

ccc tct ggg ggc ctg ccc agg gga ccc cct gag ccc ccc gac cgg ctt     2496
Pro Ser Gly Gly Leu Pro Arg Gly Pro Pro Glu Pro Pro Asp Arg Leu
            820                 825                 830

agc tgt gat ggg agt cga gtg cat ttg ctt tat aag tga                 2535
Ser Cys Asp Gly Ser Arg Val His Leu Leu Tyr Lys
        835                 840


<210> SEQ ID NO 51
<211> LENGTH: 844
<212> TYPE: PRT
<213> ORGANISM: Homo sapiens

<400> SEQUENCE: 51

Met Gly Pro Gly Ala Pro Phe Ala Arg Val Gly Trp Pro Leu Pro Leu
 1               5                  10                  15

Leu Val Val Met Ala Ala Gly Val Ala Pro Val Trp Ala Ser His Ser
            20                  25                  30

Pro His Leu Pro Arg Pro His Ser Arg Val Pro Pro His Pro Ser Ser
        35                  40                  45

Glu Arg Arg Ala Val Tyr Ile Gly Ala Leu Phe Pro Met Ser Gly Gly
    50                  55                  60

Trp Pro Gly Gly Gln Ala Cys Gln Pro Ala Val Glu Met Ala Leu Glu
65                  70                  75                  80

Asp Val Asn Ser Arg Arg Asp Ile Leu Pro Asp Tyr Glu Leu Lys Leu
                85                  90                  95

Ile His His Asp Ser Lys Cys Asp Pro Gly Gln Ala Thr Lys Tyr Leu
            100                 105                 110

Tyr Glu Leu Leu Tyr Asn Asp Pro Ile Lys Ile Ile Leu Met Pro Gly
        115                 120                 125

Cys Ser Ser Val Ser Thr Leu Val Ala Glu Ala Ala Arg Met Trp Asn
    130                 135                 140

Leu Ile Val Leu Ser Tyr Gly Ser Ser Ser Pro Ala Leu Ser Asn Arg
145                 150                 155                 160
```

-continued

```
Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
            180                 185                 190

Ala Thr Ile Gln Gln Thr Thr Glu Val Phe Thr Ser Thr Leu Asp Asp
        195                 200                 205

Leu Glu Glu Arg Val Lys Glu Ala Gly Ile Glu Ile Thr Phe Arg Gln
    210                 215                 220

Ser Phe Phe Ser Asp Pro Ala Val Pro Val Lys Asn Leu Lys Arg Gln
225                 230                 235                 240

Asp Ala Arg Ile Ile Val Gly Leu Phe Tyr Glu Thr Glu Ala Arg Lys
                245                 250                 255

Val Phe Cys Glu Val Tyr Lys Glu Arg Leu Phe Gly Lys Lys Tyr Val
            260                 265                 270

Trp Phe Leu Ile Gly Trp Tyr Ala Asp Asn Trp Phe Lys Ile Tyr Asp
        275                 280                 285

Pro Ser Ile Asn Cys Thr Val Asp Glu Met Thr Glu Ala Val Glu Gly
    290                 295                 300

His Ile Thr Thr Glu Ile Val Met Leu Asn Pro Ala Asn Thr Arg Ser
305                 310                 315                 320

Ile Ser Asn Met Thr Ser Gln Glu Phe Val Glu Lys Leu Thr Lys Arg
                325                 330                 335

Leu Lys Arg His Pro Glu Glu Thr Gly Gly Phe Gln Glu Ala Pro Leu
            340                 345                 350

Ala Tyr Asp Ala Ile Trp Ala Leu Ala Leu Ala Leu Asn Lys Thr Ser
        355                 360                 365

Gly Gly Gly Gly Arg Ser Gly Val Arg Leu Glu Asp Phe Asn Tyr Asn
    370                 375                 380

Asn Gln Thr Ile Thr Asp Gln Ile Tyr Arg Ala Met Asn Ser Ser Ser
385                 390                 395                 400

Phe Glu Gly Val Ser Gly His Val Val Phe Asp Ala Ser Gly Ser Arg
                405                 410                 415

Met Ala Trp Thr Leu Ile Glu Gln Leu Gln Gly Gly Ser Tyr Lys Lys
            420                 425                 430

Ile Gly Tyr Tyr Asp Ser Thr Lys Asp Asp Leu Ser Trp Ser Lys Thr
        435                 440                 445

Asp Lys Trp Ile Gly Gly Ser Pro Pro Ala Asp Gln Thr Leu Val Ile
    450                 455                 460

Lys Thr Phe Arg Phe Leu Ser Gln Lys Leu Phe Ile Ser Val Ser Val
465                 470                 475                 480

Leu Ser Ser Leu Gly Ile Val Leu Ala Val Val Cys Leu Ser Phe Asn
                485                 490                 495

Ile Tyr Asn Ser His Val Arg Tyr Ile Gln Asn Ser Gln Pro Asn Leu
            500                 505                 510

Asn Asn Leu Thr Ala Val Gly Cys Ser Leu Ala Leu Ala Ala Val Phe
        515                 520                 525

Pro Leu Gly Leu Asp Gly Tyr His Ile Gly Arg Asn Gln Phe Pro Phe
    530                 535                 540

Val Cys Gln Ala Arg Leu Trp Leu Leu Gly Leu Gly Phe Ser Leu Gly
545                 550                 555                 560

Tyr Gly Ser Met Phe Thr Lys Ile Trp Trp Val His Thr Val Phe Thr
                565                 570                 575

Lys Lys Glu Glu Lys Lys Glu Trp Arg Lys Thr Leu Glu Pro Trp Lys
```

-continued

```
            580                 585                 590

Leu Tyr Ala Thr Val Gly Leu Leu Val Gly Met Asp Val Leu Thr Leu
        595                 600                 605

Ala Ile Trp Gln Ile Val Asp Pro Leu His Arg Thr Ile Glu Thr Phe
    610                 615                 620

Ala Lys Glu Glu Pro Lys Glu Asp Ile Asp Val Ser Ile Leu Pro Gln
625                 630                 635                 640

Leu Glu His Cys Ser Ser Arg Lys Met Asn Thr Trp Leu Gly Ile Phe
                645                 650                 655

Tyr Gly Tyr Lys Gly Leu Leu Leu Leu Leu Gly Ile Phe Leu Ala Tyr
            660                 665                 670

Glu Thr Lys Ser Val Ser Thr Glu Lys Ile Asn Asp His Arg Ala Val
        675                 680                 685

Gly Met Ala Ile Tyr Asn Val Ala Val Leu Cys Leu Ile Thr Ala Pro
    690                 695                 700

Val Thr Met Ile Leu Ser Ser Gln Gln Asp Ala Ala Phe Ala Phe Ala
705                 710                 715                 720

Ser Leu Ala Ile Val Phe Ser Ser Tyr Ile Thr Leu Val Val Leu Phe
                725                 730                 735

Val Pro Lys Met Arg Arg Leu Ile Thr Arg Gly Glu Trp Gln Ser Glu
            740                 745                 750

Ala Gln Asp Thr Met Lys Thr Gly Ser Ser Thr Asn Asn Asn Glu Glu
        755                 760                 765

Glu Lys Ser Arg Leu Leu Glu Lys Glu Asn Arg Glu Leu Glu Lys Ile
    770                 775                 780

Ile Ala Glu Lys Glu Glu Arg Val Ser Glu Leu Arg His Gln Leu Gln
785                 790                 795                 800

Ser Arg Gln Gln Leu Arg Ser Arg Arg His Pro Pro Thr Pro Pro Glu
                805                 810                 815

Pro Ser Gly Gly Leu Pro Arg Gly Pro Pro Glu Pro Pro Asp Arg Leu
            820                 825                 830

Ser Cys Asp Gly Ser Arg Val His Leu Leu Tyr Lys
        835                 840


<210> SEQ ID NO 52
<211> LENGTH: 2895
<212> TYPE: DNA
<213> ORGANISM: Canis familiaris
<220> FEATURE:
<221> NAME/KEY: CDS
<222> LOCATION: (1)...(2892)

<400> SEQUENCE: 52

atg ctg ctg ctg ctc ctg ccg ctg gcg ctg gcg ccg ctc ttc ctc cgc       48
Met Leu Leu Leu Leu Leu Pro Leu Ala Leu Ala Pro Leu Phe Leu Arg
 1               5                  10                  15

ccc ccg ggc gcg ggc ggg gca cag acc ccc aac gcc acc tcg gaa ggt       96
Pro Pro Gly Ala Gly Gly Ala Gln Thr Pro Asn Ala Thr Ser Glu Gly
            20                  25                  30

tgc cag atc ata cac ccg cct tgg gaa ggg ggt atc agg tac agg ggc      144
Cys Gln Ile Ile His Pro Pro Trp Glu Gly Gly Ile Arg Tyr Arg Gly
        35                  40                  45

ctg act cgt gac cag gtg aag gct atc aac ttc ctg ccg gtg gac tat      192
Leu Thr Arg Asp Gln Val Lys Ala Ile Asn Phe Leu Pro Val Asp Tyr
    50                  55                  60

gag att gag tat gtg tgc cgg gga gag cga gag gtg gtg ggg ccc aag      240
Glu Ile Glu Tyr Val Cys Arg Gly Glu Arg Glu Val Val Gly Pro Lys
```

-continued

```
 65                  70                  75                  80

gtc cga aag tgc ctg gcc aat ggc tcc tgg aca gat atg gac aca ccc      288
Val Arg Lys Cys Leu Ala Asn Gly Ser Trp Thr Asp Met Asp Thr Pro
                 85                  90                  95

agc cgc tgt gtc cga atc tgt tcc aag tca tat ttg gcc ctg gaa aat      336
Ser Arg Cys Val Arg Ile Cys Ser Lys Ser Tyr Leu Ala Leu Glu Asn
            100                 105                 110

ggg aag gtc ttc ctg acg ggt ggg gac ctc ccc gct ctg gat gga gcc      384
Gly Lys Val Phe Leu Thr Gly Gly Asp Leu Pro Ala Leu Asp Gly Ala
        115                 120                 125

cgg gtg gat ttc cgg tgt gac cct gac ttc cat ctt gtg ggc agc tcc      432
Arg Val Asp Phe Arg Cys Asp Pro Asp Phe His Leu Val Gly Ser Ser
    130                 135                 140

cgg agt atc tgt agt cag ggc cag tgg agc act ccc aag ccc cac tgc      480
Arg Ser Ile Cys Ser Gln Gly Gln Trp Ser Thr Pro Lys Pro His Cys
145                 150                 155                 160

cag gtg agc cga acg ccg cac tca gag cgg cga gcg gtg tac atc ggg      528
Gln Val Ser Arg Thr Pro His Ser Glu Arg Arg Ala Val Tyr Ile Gly
                165                 170                 175

gcg ctg ttt ccc atg agc ggg ggc tgg ccg ggg ggc cag gcc tgc cag      576
Ala Leu Phe Pro Met Ser Gly Gly Trp Pro Gly Gly Gln Ala Cys Gln
            180                 185                 190

ccc gcg gtg gag atg gcg ctg gag gac gtg aat agc cgc agg gac atc      624
Pro Ala Val Glu Met Ala Leu Glu Asp Val Asn Ser Arg Arg Asp Ile
        195                 200                 205

ctg ccg gac tac gag ctc aag ctc atc cac cac gac agc aag tgt gac      672
Leu Pro Asp Tyr Glu Leu Lys Leu Ile His His Asp Ser Lys Cys Asp
    210                 215                 220

cca ggc caa gct acc aag tac ctg tat gaa ctg ctc tac aac gac ccc      720
Pro Gly Gln Ala Thr Lys Tyr Leu Tyr Glu Leu Leu Tyr Asn Asp Pro
225                 230                 235                 240

atc aag atc atc ctc atg cct ggc tgc agc tct gtc tcc acg ctt gtg      768
Ile Lys Ile Ile Leu Met Pro Gly Cys Ser Ser Val Ser Thr Leu Val
                245                 250                 255

gct gag gct gcc agg atg tgg aac ctc att gtg ctc tcc tat ggt tcc      816
Ala Glu Ala Ala Arg Met Trp Asn Leu Ile Val Leu Ser Tyr Gly Ser
            260                 265                 270

agc tca cca gct ctg tcc aac cgg cag cgc ttt cct acc ttc ttc cga      864
Ser Ser Pro Ala Leu Ser Asn Arg Gln Arg Phe Pro Thr Phe Phe Arg
        275                 280                 285

act cat ccc tcg gcc acg ctc cac aac cct acg cga gtg aag ctc ttt      912
Thr His Pro Ser Ala Thr Leu His Asn Pro Thr Arg Val Lys Leu Phe
    290                 295                 300

gag aag tgg ggc tgg agg aag att gcc acc atc cag cag acc acc gag      960
Glu Lys Trp Gly Trp Arg Lys Ile Ala Thr Ile Gln Gln Thr Thr Glu
305                 310                 315                 320

gtg ttc aca tcg act ctg gac gac cta gag gaa cga gtg aag gag gct     1008
Val Phe Thr Ser Thr Leu Asp Asp Leu Glu Glu Arg Val Lys Glu Ala
                325                 330                 335

ggg att gag att act ttc cgc cag agc ttc ttc tca gat cct gcc gtg     1056
Gly Ile Glu Ile Thr Phe Arg Gln Ser Phe Phe Ser Asp Pro Ala Val
            340                 345                 350

cct gtc aag aac ctc aag cgc cag gat gcc cga atc atc gtg gga ctt     1104
Pro Val Lys Asn Leu Lys Arg Gln Asp Ala Arg Ile Ile Val Gly Leu
        355                 360                 365

ttc tat gag act gaa gcc cgg aaa gtg ttc tgt gag gta tac aag gag     1152
Phe Tyr Glu Thr Glu Ala Arg Lys Val Phe Cys Glu Val Tyr Lys Glu
    370                 375                 380

cgg ctc ttt ggg aag aag tat gtg tgg ttc ctc att ggg tgg tat gct     1200
```

-continued

```
Arg Leu Phe Gly Lys Lys Tyr Val Trp Phe Leu Ile Gly Trp Tyr Ala
385                 390                 395                 400

gac aat tgg ttc aag acc tac gac ccc tcc atc aac tgc aca gtg gat     1248
Asp Asn Trp Phe Lys Thr Tyr Asp Pro Ser Ile Asn Cys Thr Val Asp
                405                 410                 415

gag atg acc gag gct gtg gaa ggc cac atc acc act gag att gtc atg     1296
Glu Met Thr Glu Ala Val Glu Gly His Ile Thr Thr Glu Ile Val Met
            420                 425                 430

ctg aac cca gcc aac acc cgc agc atc tcc aac atg aca tcc cag gag     1344
Leu Asn Pro Ala Asn Thr Arg Ser Ile Ser Asn Met Thr Ser Gln Glu
        435                 440                 445

ttt gtg gag aaa ctg acc aag aga ctc aag aga cac cct gag gag aca     1392
Phe Val Glu Lys Leu Thr Lys Arg Leu Lys Arg His Pro Glu Glu Thr
    450                 455                 460

ggc ggc ttc cag gag gca ccg ctg gcc tat gat gcc atc tgg gcc ttg     1440
Gly Gly Phe Gln Glu Ala Pro Leu Ala Tyr Asp Ala Ile Trp Ala Leu
465                 470                 475                 480

gca ttg gcc ctg aac aag aca tct gga ggg agc ggc cgt tcg ggg gtg     1488
Ala Leu Ala Leu Asn Lys Thr Ser Gly Gly Ser Gly Arg Ser Gly Val
                485                 490                 495

cgc ctg gaa gac ttc aac tac aac aac cag acg atc aca gac caa atc     1536
Arg Leu Glu Asp Phe Asn Tyr Asn Asn Gln Thr Ile Thr Asp Gln Ile
            500                 505                 510

tac cgc gca atg aac tcc tcg tcc ttt gag ggt gtc tct ggc cac gtg     1584
Tyr Arg Ala Met Asn Ser Ser Ser Phe Glu Gly Val Ser Gly His Val
        515                 520                 525

gtg ttt gat gcc agc ggc tca cgg atg gcc tgg act ctg att gag cag     1632
Val Phe Asp Ala Ser Gly Ser Arg Met Ala Trp Thr Leu Ile Glu Gln
    530                 535                 540

ctg cag ggt ggc agc tac aag aag atc ggc tac tat gac agc acc aag     1680
Leu Gln Gly Gly Ser Tyr Lys Lys Ile Gly Tyr Tyr Asp Ser Thr Lys
545                 550                 555                 560

gat gac ctt tcc tgg tct aaa acg gac aaa tgg att gga ggg gcc ccc     1728
Asp Asp Leu Ser Trp Ser Lys Thr Asp Lys Trp Ile Gly Gly Ala Pro
                565                 570                 575

ccg gcc gac cag acc ctg gtc atc aag aca ttt cgc ttc atg tca cag     1776
Pro Ala Asp Gln Thr Leu Val Ile Lys Thr Phe Arg Phe Met Ser Gln
            580                 585                 590

aag ctc ttc att tca gtc tct gtc ctc tcc agc ctg ggc att gtc ctg     1824
Lys Leu Phe Ile Ser Val Ser Val Leu Ser Ser Leu Gly Ile Val Leu
        595                 600                 605

gct gtg gtc tgt ctg tcc ttt aac atc tac aac tct cat gtc cgt tac     1872
Ala Val Val Cys Leu Ser Phe Asn Ile Tyr Asn Ser His Val Arg Tyr
    610                 615                 620

atc cag aac tcc cag ccc aac ttg aac aat ctg act gct gtg ggc tgc     1920
Ile Gln Asn Ser Gln Pro Asn Leu Asn Asn Leu Thr Ala Val Gly Cys
625                 630                 635                 640

tcc ctg gca ttg gct gcc gtc ttc ccc ctg ggg cta gat ggg tac cac     1968
Ser Leu Ala Leu Ala Ala Val Phe Pro Leu Gly Leu Asp Gly Tyr His
                645                 650                 655

atc ggg aga agc cag ttt cct ttt gtg tgt cag gca cgc ctc tgg ctc     2016
Ile Gly Arg Ser Gln Phe Pro Phe Val Cys Gln Ala Arg Leu Trp Leu
            660                 665                 670

ctg ggt ctg ggc ttc agt ctg ggc tat ggc tcc atg ttc acg aag atc     2064
Leu Gly Leu Gly Phe Ser Leu Gly Tyr Gly Ser Met Phe Thr Lys Ile
        675                 680                 685

tgg tgg gtc cac acg gtc ttc act aag aag gag gag aag aag gag tgg     2112
Trp Trp Val His Thr Val Phe Thr Lys Lys Glu Glu Lys Lys Glu Trp
    690                 695                 700
```

-continued

```
agg aag acc ctg gag ccc tgg aag ctg tac acc aca gtg ggc ttg cta      2160
Arg Lys Thr Leu Glu Pro Trp Lys Leu Tyr Thr Thr Val Gly Leu Leu
705                 710                 715                 720

gtg ggc atg gat gtc ctc act ctt gcc att tgg cag atg gta gac ccc      2208
Val Gly Met Asp Val Leu Thr Leu Ala Ile Trp Gln Met Val Asp Pro
                725                 730                 735

ttg cac cgg acc att gag act ttt gcc aag gag gaa cca aag gaa gat      2256
Leu His Arg Thr Ile Glu Thr Phe Ala Lys Glu Glu Pro Lys Glu Asp
            740                 745                 750

att gat gtg tcc atc ctg ccc cag ctg gag cac tgc agc tcc aag aaa      2304
Ile Asp Val Ser Ile Leu Pro Gln Leu Glu His Cys Ser Ser Lys Lys
        755                 760                 765

atg aac acc tgg ctt ggc att ttc tat ggt tac aag ggg ctg ctg ctg      2352
Met Asn Thr Trp Leu Gly Ile Phe Tyr Gly Tyr Lys Gly Leu Leu Leu
    770                 775                 780

ctg cta ggc atc ttt ctt gct tat gag acc aag agc gtg tct act gag      2400
Leu Leu Gly Ile Phe Leu Ala Tyr Glu Thr Lys Ser Val Ser Thr Glu
785                 790                 795                 800

aag atc aat gac cac cgg gct gtg ggc atg gcc atg tac aac gtg gcg      2448
Lys Ile Asn Asp His Arg Ala Val Gly Met Ala Met Tyr Asn Val Ala
                805                 810                 815

gtc ctg tgc ctc atc act gcc ccg gtc acc atg atc ctg tcc agc cag      2496
Val Leu Cys Leu Ile Thr Ala Pro Val Thr Met Ile Leu Ser Ser Gln
            820                 825                 830

cag gat gca gct ttc gcc ttt gca gct ctt gcc ata gtg ttc tcc tcc      2544
Gln Asp Ala Ala Phe Ala Phe Ala Ala Leu Ala Ile Val Phe Ser Ser
        835                 840                 845

tac atc act ctg gtc gtt ctg ttc gtg ccg aag atg cgc agg ttg atc      2592
Tyr Ile Thr Leu Val Val Leu Phe Val Pro Lys Met Arg Arg Leu Ile
    850                 855                 860

acc cgg ggt gag tgg cag tcg gag gcg cag gat acc atg aaa acg ggg      2640
Thr Arg Gly Glu Trp Gln Ser Glu Ala Gln Asp Thr Met Lys Thr Gly
865                 870                 875                 880

tcg tcg acc aac aac aat gag gaa gag aag tcc cga ctg ttg gag aag      2688
Ser Ser Thr Asn Asn Asn Glu Glu Glu Lys Ser Arg Leu Leu Glu Lys
                885                 890                 895

gag aac cgg gag ctg gag aag atc att gct gag aaa gag gag cga gtg      2736
Glu Asn Arg Glu Leu Glu Lys Ile Ile Ala Glu Lys Glu Glu Arg Val
            900                 905                 910

tcc gag ctg cgc cat cag ctt cgt tct cgg cag cag ctg cgc cct cgg      2784
Ser Glu Leu Arg His Gln Leu Arg Ser Arg Gln Gln Leu Arg Pro Arg
        915                 920                 925

cgt cac ccc ccg acg ccc cca gac ccc tca ggg ggc ctg ccc agg gga      2832
Arg His Pro Pro Thr Pro Pro Asp Pro Ser Gly Gly Leu Pro Arg Gly
    930                 935                 940

ccc cat gag ccc cct gac cgg ctc agc tgt gac ggg agc cgg gtt cac      2880
Pro His Glu Pro Pro Asp Arg Leu Ser Cys Asp Gly Ser Arg Val His
945                 950                 955                 960

ttg ctg tac aag tga                                                  2895
Leu Leu Tyr Lys


<210> SEQ ID NO 53
<211> LENGTH: 964
<212> TYPE: PRT
<213> ORGANISM: Canis familiaris

<400> SEQUENCE: 53

Met Leu Leu Leu Leu Leu Pro Leu Ala Leu Ala Pro Leu Phe Leu Arg
 1              5                   10                  15

Pro Pro Gly Ala Gly Gly Ala Gln Thr Pro Asn Ala Thr Ser Glu Gly
```

-continued

```
            20                  25                  30

Cys Gln Ile Ile His Pro Pro Trp Glu Gly Gly Ile Arg Tyr Arg Gly
        35                  40                  45

Leu Thr Arg Asp Gln Val Lys Ala Ile Asn Phe Leu Pro Val Asp Tyr
    50                  55                  60

Glu Ile Glu Tyr Val Cys Arg Gly Glu Arg Glu Val Val Gly Pro Lys
65                  70                  75                  80

Val Arg Lys Cys Leu Ala Asn Gly Ser Trp Thr Asp Met Asp Thr Pro
                85                  90                  95

Ser Arg Cys Val Arg Ile Cys Ser Lys Ser Tyr Leu Ala Leu Glu Asn
            100                 105                 110

Gly Lys Val Phe Leu Thr Gly Gly Asp Leu Pro Ala Leu Asp Gly Ala
        115                 120                 125

Arg Val Asp Phe Arg Cys Asp Pro Asp Phe His Leu Val Gly Ser Ser
    130                 135                 140

Arg Ser Ile Cys Ser Gln Gly Gln Trp Ser Thr Pro Lys Pro His Cys
145                 150                 155                 160

Gln Val Ser Arg Thr Pro His Ser Glu Arg Arg Ala Val Tyr Ile Gly
                165                 170                 175

Ala Leu Phe Pro Met Ser Gly Gly Trp Pro Gly Gly Gln Ala Cys Gln
            180                 185                 190

Pro Ala Val Glu Met Ala Leu Glu Asp Val Asn Ser Arg Arg Asp Ile
        195                 200                 205

Leu Pro Asp Tyr Glu Leu Lys Leu Ile His His Asp Ser Lys Cys Asp
    210                 215                 220

Pro Gly Gln Ala Thr Lys Tyr Leu Tyr Glu Leu Leu Tyr Asn Asp Pro
225                 230                 235                 240

Ile Lys Ile Ile Leu Met Pro Gly Cys Ser Ser Val Ser Thr Leu Val
                245                 250                 255

Ala Glu Ala Ala Arg Met Trp Asn Leu Ile Val Leu Ser Tyr Gly Ser
            260                 265                 270

Ser Ser Pro Ala Leu Ser Asn Arg Gln Arg Phe Pro Thr Phe Phe Arg
        275                 280                 285

Thr His Pro Ser Ala Thr Leu His Asn Pro Thr Arg Val Lys Leu Phe
    290                 295                 300

Glu Lys Trp Gly Trp Arg Lys Ile Ala Thr Ile Gln Gln Thr Thr Glu
305                 310                 315                 320

Val Phe Thr Ser Thr Leu Asp Asp Leu Glu Glu Arg Val Lys Glu Ala
                325                 330                 335

Gly Ile Glu Ile Thr Phe Arg Gln Ser Phe Phe Ser Asp Pro Ala Val
            340                 345                 350

Pro Val Lys Asn Leu Lys Arg Gln Asp Ala Arg Ile Ile Val Gly Leu
        355                 360                 365

Phe Tyr Glu Thr Glu Ala Arg Lys Val Phe Cys Glu Val Tyr Lys Glu
    370                 375                 380

Arg Leu Phe Gly Lys Lys Tyr Val Trp Phe Leu Ile Gly Trp Tyr Ala
385                 390                 395                 400

Asp Asn Trp Phe Lys Thr Tyr Asp Pro Ser Ile Asn Cys Thr Val Asp
                405                 410                 415

Glu Met Thr Glu Ala Val Glu Gly His Ile Thr Thr Glu Ile Val Met
            420                 425                 430

Leu Asn Pro Ala Asn Thr Arg Ser Ile Ser Asn Met Thr Ser Gln Glu
        435                 440                 445
```

-continued

```
Phe Val Glu Lys Leu Thr Lys Arg Leu Lys Arg His Pro Glu Glu Thr
    450                 455                 460

Gly Gly Phe Gln Glu Ala Pro Leu Ala Tyr Asp Ala Ile Trp Ala Leu
465                 470                 475                 480

Ala Leu Ala Leu Asn Lys Thr Ser Gly Gly Ser Gly Arg Ser Gly Val
                485                 490                 495

Arg Leu Glu Asp Phe Asn Tyr Asn Asn Gln Thr Ile Thr Asp Gln Ile
            500                 505                 510

Tyr Arg Ala Met Asn Ser Ser Ser Phe Glu Gly Val Ser Gly His Val
        515                 520                 525

Val Phe Asp Ala Ser Gly Ser Arg Met Ala Trp Thr Leu Ile Glu Gln
    530                 535                 540

Leu Gln Gly Gly Ser Tyr Lys Lys Ile Gly Tyr Tyr Asp Ser Thr Lys
545                 550                 555                 560

Asp Asp Leu Ser Trp Ser Lys Thr Asp Lys Trp Ile Gly Gly Ala Pro
                565                 570                 575

Pro Ala Asp Gln Thr Leu Val Ile Lys Thr Phe Arg Phe Met Ser Gln
            580                 585                 590

Lys Leu Phe Ile Ser Val Ser Val Leu Ser Ser Leu Gly Ile Val Leu
        595                 600                 605

Ala Val Val Cys Leu Ser Phe Asn Ile Tyr Asn Ser His Val Arg Tyr
    610                 615                 620

Ile Gln Asn Ser Gln Pro Asn Leu Asn Asn Leu Thr Ala Val Gly Cys
625                 630                 635                 640

Ser Leu Ala Leu Ala Ala Val Phe Pro Leu Gly Leu Asp Gly Tyr His
                645                 650                 655

Ile Gly Arg Ser Gln Phe Pro Phe Val Cys Gln Ala Arg Leu Trp Leu
            660                 665                 670

Leu Gly Leu Gly Phe Ser Leu Gly Tyr Gly Ser Met Phe Thr Lys Ile
        675                 680                 685

Trp Trp Val His Thr Val Phe Thr Lys Lys Glu Glu Lys Lys Glu Trp
    690                 695                 700

Arg Lys Thr Leu Glu Pro Trp Lys Leu Tyr Thr Thr Val Gly Leu Leu
705                 710                 715                 720

Val Gly Met Asp Val Leu Thr Leu Ala Ile Trp Gln Met Val Asp Pro
                725                 730                 735

Leu His Arg Thr Ile Glu Thr Phe Ala Lys Glu Glu Pro Lys Glu Asp
            740                 745                 750

Ile Asp Val Ser Ile Leu Pro Gln Leu Glu His Cys Ser Ser Lys Lys
        755                 760                 765

Met Asn Thr Trp Leu Gly Ile Phe Tyr Gly Tyr Lys Gly Leu Leu Leu
    770                 775                 780

Leu Leu Gly Ile Phe Leu Ala Tyr Glu Thr Lys Ser Val Ser Thr Glu
785                 790                 795                 800

Lys Ile Asn Asp His Arg Ala Val Gly Met Ala Met Tyr Asn Val Ala
                805                 810                 815

Val Leu Cys Leu Ile Thr Ala Pro Val Thr Met Ile Leu Ser Ser Gln
            820                 825                 830

Gln Asp Ala Ala Phe Ala Phe Ala Ala Leu Ala Ile Val Phe Ser Ser
        835                 840                 845

Tyr Ile Thr Leu Val Val Leu Phe Val Pro Lys Met Arg Arg Leu Ile
    850                 855                 860
```

-continued

```
Thr Arg Gly Glu Trp Gln Ser Glu Ala Gln Asp Thr Met Lys Thr Gly
865                 870                 875                 880

Ser Ser Thr Asn Asn Asn Glu Glu Glu Lys Ser Arg Leu Leu Glu Lys
                885                 890                 895

Glu Asn Arg Glu Leu Glu Lys Ile Ile Ala Glu Lys Glu Glu Arg Val
            900                 905                 910

Ser Glu Leu Arg His Gln Leu Arg Ser Arg Gln Gln Leu Arg Pro Arg
        915                 920                 925

Arg His Pro Pro Thr Pro Pro Asp Pro Ser Gly Gly Leu Pro Arg Gly
    930                 935                 940

Pro His Glu Pro Pro Asp Arg Leu Ser Cys Asp Gly Ser Arg Val His
945                 950                 955                 960

Leu Leu Tyr Lys


<210> SEQ ID NO 54
<211> LENGTH: 1737
<212> TYPE: DNA
<213> ORGANISM: Homo sapiens
<220> FEATURE:
<221> NAME/KEY: CDS
<222> LOCATION: (1)...(1734)

<400> SEQUENCE: 54

atg ttg ctg ctg ctg cta ctg gcg cca ctc ttc ctc cgc ccc ccg ggc       48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc       96
Ala Gly Gly Ala Gln Thr Pro Asn Ala Thr Ser Glu Gly Cys Gln Ile
            20                  25                  30

ata cac ccg ccc tgg gaa ggg ggc atc agg tac cgg ggc ctg act cgg      144
Ile His Pro Pro Trp Glu Gly Gly Ile Arg Tyr Arg Gly Leu Thr Arg
        35                  40                  45

gac cag gtg aag gct atc aac ttc ctg cca gtg gac tat gag att gag      192
Asp Gln Val Lys Ala Ile Asn Phe Leu Pro Val Asp Tyr Glu Ile Glu
     50                  55                  60

tat gtg tgc cgg ggg gag cgc gag gtg gtg ggg ccc aag gtc cgc aag      240
Tyr Val Cys Arg Gly Glu Arg Glu Val Val Gly Pro Lys Val Arg Lys
 65                  70                  75                  80

tgc ctg gcc aac ggc tcc tgg aca gat atg gac aca ccc agc cgc tgt      288
Cys Leu Ala Asn Gly Ser Trp Thr Asp Met Asp Thr Pro Ser Arg Cys
                 85                  90                  95

gtc cga atc tgc tcc aag tct tat ttg acc ctg gaa aat ggg aag gtt      336
Val Arg Ile Cys Ser Lys Ser Tyr Leu Thr Leu Glu Asn Gly Lys Val
            100                 105                 110

ttc ctg acg ggt ggg gac ctc cca gct ctg gac gga gcc cgg gtg gat      384
Phe Leu Thr Gly Gly Asp Leu Pro Ala Leu Asp Gly Ala Arg Val Asp
        115                 120                 125

ttc cgg tgt gac ccc gac ttc cat ctg gtg ggc agc tcc cgg agc atc      432
Phe Arg Cys Asp Pro Asp Phe His Leu Val Gly Ser Ser Arg Ser Ile
    130                 135                 140

tgt agt cag ggc cag tgg agc acc ccc aag ccc cac tgc cag gtg aat      480
Cys Ser Gln Gly Gln Trp Ser Thr Pro Lys Pro His Cys Gln Val Asn
145                 150                 155                 160

cga acg cca cac tca gaa cgg cgc gca gtg tac atc ggg gca ctg ttt      528
Arg Thr Pro His Ser Glu Arg Arg Ala Val Tyr Ile Gly Ala Leu Phe
                165                 170                 175

ccc atg agc ggg ggc tgg cca ggg ggc cag gcc tgc cag ccc gcg gtg      576
Pro Met Ser Gly Gly Trp Pro Gly Gly Gln Ala Cys Gln Pro Ala Val
            180                 185                 190
```

-continued

```
gag atg gcg ctg gag gac gtg aat agc cgc agg gac atc ctg ccg gac      624
Glu Met Ala Leu Glu Asp Val Asn Ser Arg Arg Asp Ile Leu Pro Asp
        195                 200                 205

tat gag ctc aag ctc atc cac cac gac agc aag tgt gat cca ggc caa      672
Tyr Glu Leu Lys Leu Ile His His Asp Ser Lys Cys Asp Pro Gly Gln
    210                 215                 220

gcc acc aag tac cta tat gag ctg ctc tac aac gac cct atc aag atc      720
Ala Thr Lys Tyr Leu Tyr Glu Leu Leu Tyr Asn Asp Pro Ile Lys Ile
225                 230                 235                 240

atc ctt atg cct ggc tgc agc tct gtc tcc acg ctg gtg gct gag gct      768
Ile Leu Met Pro Gly Cys Ser Ser Val Ser Thr Leu Val Ala Glu Ala
                245                 250                 255

gct agg atg tgg aac ctc att gtg ctt tcc tat ggc tcc agc tca cca      816
Ala Arg Met Trp Asn Leu Ile Val Leu Ser Tyr Gly Ser Ser Ser Pro
            260                 265                 270

gcc ctg tca aac cgg cag cgt ttc ccc act ttc ttc cga acg cac cca      864
Ala Leu Ser Asn Arg Gln Arg Phe Pro Thr Phe Phe Arg Thr His Pro
        275                 280                 285

tca gcc aca ctc cac aac cct acc cgc gtg aaa ctc ttt gaa aag tgg      912
Ser Ala Thr Leu His Asn Pro Thr Arg Val Lys Leu Phe Glu Lys Trp
    290                 295                 300

ggc tgg aag aag att gct acc atc cag cag acc act gag gtc ttc act      960
Gly Trp Lys Lys Ile Ala Thr Ile Gln Gln Thr Thr Glu Val Phe Thr
305                 310                 315                 320

tcg act ctg gac gac ctg gag gaa cga gtg aag gag gct gga att gag     1008
Ser Thr Leu Asp Asp Leu Glu Glu Arg Val Lys Glu Ala Gly Ile Glu
                325                 330                 335

att act ttc cgc cag agt ttc ttc tca gat cca gct gtg ccc gtc aaa     1056
Ile Thr Phe Arg Gln Ser Phe Phe Ser Asp Pro Ala Val Pro Val Lys
            340                 345                 350

aac ctg aag cgc cag gat gcc cga atc atc gtg gga ctt ttc tat gag     1104
Asn Leu Lys Arg Gln Asp Ala Arg Ile Ile Val Gly Leu Phe Tyr Glu
        355                 360                 365

act gaa gcc cgg aaa gtt ttt tgt gag gtg tac aag gag cgt ctc ttt     1152
Thr Glu Ala Arg Lys Val Phe Cys Glu Val Tyr Lys Glu Arg Leu Phe
    370                 375                 380

ggg aag aag tac gtc tgg ttc ctc att ggg tgg tat gct gac aat tgg     1200
Gly Lys Lys Tyr Val Trp Phe Leu Ile Gly Trp Tyr Ala Asp Asn Trp
385                 390                 395                 400

ttc aag atc tac gac cct tct atc aac tgc aca gtg gat gag atg act     1248
Phe Lys Ile Tyr Asp Pro Ser Ile Asn Cys Thr Val Asp Glu Met Thr
                405                 410                 415

gag gcg gtg gag ggc cac atc aca act gag att gtc atg ctg aat cct     1296
Glu Ala Val Glu Gly His Ile Thr Thr Glu Ile Val Met Leu Asn Pro
            420                 425                 430

gcc aat acc cgc agc att tcc aac atg aca tcc cag gaa ttt gtg gag     1344
Ala Asn Thr Arg Ser Ile Ser Asn Met Thr Ser Gln Glu Phe Val Glu
        435                 440                 445

aaa cta acc aag cga ctg aaa aga cac cct gag gag aca gga ggc ttc     1392
Lys Leu Thr Lys Arg Leu Lys Arg His Pro Glu Glu Thr Gly Gly Phe
    450                 455                 460

cag gag gca ccg ctg gcc tat gat gcc atc tgg gcc ttg gca ctg gcc     1440
Gln Glu Ala Pro Leu Ala Tyr Asp Ala Ile Trp Ala Leu Ala Leu Ala
465                 470                 475                 480

ctg aac aag aca tct gga gga ggc ggc cgt tct ggt gtg cgc ctg gag     1488
Leu Asn Lys Thr Ser Gly Gly Gly Gly Arg Ser Gly Val Arg Leu Glu
                485                 490                 495

gac ttc aac tac aac aac cag acc att acc gac caa atc tac cgg gca     1536
Asp Phe Asn Tyr Asn Asn Gln Thr Ile Thr Asp Gln Ile Tyr Arg Ala
            500                 505                 510
```

```
atg aac tct tcg tcc ttt gag ggt gtc tct ggc cat gtg gtg ttt gat     1584
Met Asn Ser Ser Ser Phe Glu Gly Val Ser Gly His Val Val Phe Asp
        515                 520                 525

gcc agc ggc tct cgg atg gca tgg acg ctt atc gag cag ctt cag ggt     1632
Ala Ser Gly Ser Arg Met Ala Trp Thr Leu Ile Glu Gln Leu Gln Gly
    530                 535                 540

ggc agc tac aag aag att ggc tac tat gac agc acc aag gat gat ctt     1680
Gly Ser Tyr Lys Lys Ile Gly Tyr Tyr Asp Ser Thr Lys Asp Asp Leu
545                 550                 555                 560

tcc tgg tcc aaa aca gat aaa tgg att gtt ata tcc aga act cac agc     1728
Ser Trp Ser Lys Thr Asp Lys Trp Ile Val Ile Ser Arg Thr His Ser
                565                 570                 575

cca acc tga                                                         1737
Pro Thr


<210> SEQ ID NO 55
<211> LENGTH: 578
<212> TYPE: PRT
<213> ORGANISM: Homo sapiens

<400> SEQUENCE: 55

Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Val Gly Ser Ser Arg Ser Ile
    130                 135                 140

Cys Ser Gln Gly Gln Trp Ser Thr Pro Lys Pro His Cys Gln Val Asn
145                 150                 155                 160

Arg Thr Pro His Ser Glu Arg Arg Ala Val Tyr Ile Gly Ala Leu Phe
                165                 170                 175

Pro Met Ser Gly Gly Trp Pro Gly Gly Gln Ala Cys Gln Pro Ala Val
            180                 185                 190

Glu Met Ala Leu Glu Asp Val Asn Ser Arg Arg Asp Ile Leu Pro Asp
        195                 200                 205

Tyr Glu Leu Lys Leu Ile His His Asp Ser Lys Cys Asp Pro Gly Gln
    210                 215                 220

Ala Thr Lys Tyr Leu Tyr Glu Leu Leu Tyr Asn Asp Pro Ile Lys Ile
225                 230                 235                 240

Ile Leu Met Pro Gly Cys Ser Ser Val Ser Thr Leu Val Ala Glu Ala
                245                 250                 255

Ala Arg Met Trp Asn Leu Ile Val Leu Ser Tyr Gly Ser Ser Ser Pro
            260                 265                 270
```

-continued

```
Ala Leu Ser Asn Arg Gln Arg Phe Pro Thr Phe Phe Arg Thr His Pro
        275                 280                 285

Ser Ala Thr Leu His Asn Pro Thr Arg Val Lys Leu Phe Glu Lys Trp
    290                 295                 300

Gly Trp Lys Lys Ile Ala Thr Ile Gln Gln Thr Thr Glu Val Phe Thr
305                 310                 315                 320

Ser Thr Leu Asp Asp Leu Glu Glu Arg Val Lys Glu Ala Gly Ile Glu
                325                 330                 335

Ile Thr Phe Arg Gln Ser Phe Phe Ser Asp Pro Ala Val Pro Val Lys
            340                 345                 350

Asn Leu Lys Arg Gln Asp Ala Arg Ile Ile Val Gly Leu Phe Tyr Glu
        355                 360                 365

Thr Glu Ala Arg Lys Val Phe Cys Glu Val Tyr Lys Glu Arg Leu Phe
    370                 375                 380

Gly Lys Lys Tyr Val Trp Phe Leu Ile Gly Trp Tyr Ala Asp Asn Trp
385                 390                 395                 400

Phe Lys Ile Tyr Asp Pro Ser Ile Asn Cys Thr Val Asp Glu Met Thr
                405                 410                 415

Glu Ala Val Glu Gly His Ile Thr Thr Glu Ile Val Met Leu Asn Pro
            420                 425                 430

Ala Asn Thr Arg Ser Ile Ser Asn Met Thr Ser Gln Glu Phe Val Glu
        435                 440                 445

Lys Leu Thr Lys Arg Leu Lys Arg His Pro Glu Glu Thr Gly Gly Phe
    450                 455                 460

Gln Glu Ala Pro Leu Ala Tyr Asp Ala Ile Trp Ala Leu Ala Leu Ala
465                 470                 475                 480

Leu Asn Lys Thr Ser Gly Gly Gly Gly Arg Ser Gly Val Arg Leu Glu
                485                 490                 495

Asp Phe Asn Tyr Asn Asn Gln Thr Ile Thr Asp Gln Ile Tyr Arg Ala
            500                 505                 510

Met Asn Ser Ser Ser Phe Glu Gly Val Ser Gly His Val Val Phe Asp
        515                 520                 525

Ala Ser Gly Ser Arg Met Ala Trp Thr Leu Ile Glu Gln Leu Gln Gly
    530                 535                 540

Gly Ser Tyr Lys Lys Ile Gly Tyr Tyr Asp Ser Thr Lys Asp Asp Leu
545                 550                 555                 560

Ser Trp Ser Lys Thr Asp Lys Trp Ile Val Ile Ser Arg Thr His Ser
                565                 570                 575

Pro Thr


<210> SEQ ID NO 56
<211> LENGTH: 1386
<212> TYPE: DNA
<213> ORGANISM: Homo sapiens
<220> FEATURE:
<221> NAME/KEY: CDS
<222> LOCATION: (1)...(1383)

<400> SEQUENCE: 56

atg ggg ccc ggg gcc cct ttt gcc cgg gtg ggg tgg cca ctg ccg ctt       48
Met Gly Pro Gly Ala Pro Phe Ala Arg Val Gly Trp Pro Leu Pro Leu
 1               5                  10                  15

ctg gtt gtg atg gcg gca ggg gtg gct ccg gtg tgg gcc tcc cac tcc       96
Leu Val Val Met Ala Ala Gly Val Ala Pro Val Trp Ala Ser His Ser
            20                  25                  30

ccc cat ctc ccg cgg cct cac tcg cgg gtc ccc ccg cac ccc tcc tca      144
```

-continued

```
Pro His Leu Pro Arg Pro His Ser Arg Val Pro Pro His Pro Ser Ser
        35                  40                  45

gaa cgg cgc gca gtg tac atc ggg gca ctg ttt ccc atg agc ggg ggc      192
Glu Arg Arg Ala Val Tyr Ile Gly Ala Leu Phe Pro Met Ser Gly Gly
    50                  55                  60

tgg cca ggg ggc cag gcc tgc cag ccc gcg gtg gag atg gcg ctg gag      240
Trp Pro Gly Gly Gln Ala Cys Gln Pro Ala Val Glu Met Ala Leu Glu
 65                  70                  75                  80

gac gtg aat agc cgc agg gac atc ctg ccg gac tat gag ctc aag ctc      288
Asp Val Asn Ser Arg Arg Asp Ile Leu Pro Asp Tyr Glu Leu Lys Leu
                 85                  90                  95

atc cac cac gac agc aag tgt gat cca ggc caa gcc acc aag tac cta      336
Ile His His Asp Ser Lys Cys Asp Pro Gly Gln Ala Thr Lys Tyr Leu
            100                 105                 110

tat gag ctg ctc tac aac gac cct atc aag atc atc ctt atg cct ggc      384
Tyr Glu Leu Leu Tyr Asn Asp Pro Ile Lys Ile Ile Leu Met Pro Gly
        115                 120                 125

tgc agc tct gtc tcc acg ctg gtg gct gag gct gct agg atg tgg aac      432
Cys Ser Ser Val Ser Thr Leu Val Ala Glu Ala Ala Arg Met Trp Asn
    130                 135                 140

ctc att gtg ctt tcc tat ggc tcc agc tca cca gcc ctg tca aac cgg      480
Leu Ile Val Leu Ser Tyr Gly Ser Ser Ser Pro Ala Leu Ser Asn Arg
145                 150                 155                 160

cag cgt ttc ccc act ttc ttc cga acg cac cca tca gcc aca ctc cac      528
Gln Arg Phe Pro Thr Phe Phe Arg Thr His Pro Ser Ala Thr Leu His
                165                 170                 175

aac cct acc cgc gtg aaa ctc ttt gaa aag tgg ggc tgg aag aag att      576
Asn Pro Thr Arg Val Lys Leu Phe Glu Lys Trp Gly Trp Lys Lys Ile
            180                 185                 190

gct acc atc cag cag acc act gag gtc ttc act tcg act ctg gac gac      624
Ala Thr Ile Gln Gln Thr Thr Glu Val Phe Thr Ser Thr Leu Asp Asp
        195                 200                 205

ctg gag gaa cga gtg aag gag gct gga att gag att act ttc cgc cag      672
Leu Glu Glu Arg Val Lys Glu Ala Gly Ile Glu Ile Thr Phe Arg Gln
    210                 215                 220

agt ttc ttc tca gat cca gct gtg ccc gtc aaa aac ctg aag cgc cag      720
Ser Phe Phe Ser Asp Pro Ala Val Pro Val Lys Asn Leu Lys Arg Gln
225                 230                 235                 240

gat gcc cga atc atc gtg gga ctt ttc tat gag act gaa gcc cgg aaa      768
Asp Ala Arg Ile Ile Val Gly Leu Phe Tyr Glu Thr Glu Ala Arg Lys
                245                 250                 255

gtt ttt tgt gag gtg tac aag gag cgt ctc ttt ggg aag aag tac gtc      816
Val Phe Cys Glu Val Tyr Lys Glu Arg Leu Phe Gly Lys Lys Tyr Val
            260                 265                 270

tgg ttc ctc att ggg tgg tat gct gac aat tgg ttc aag atc tac gac      864
Trp Phe Leu Ile Gly Trp Tyr Ala Asp Asn Trp Phe Lys Ile Tyr Asp
        275                 280                 285

cct tct atc aac tgc aca gtg gat gag atg act gag gcg gtg gag ggc      912
Pro Ser Ile Asn Cys Thr Val Asp Glu Met Thr Glu Ala Val Glu Gly
    290                 295                 300

cac atc aca act gag att gtc atg ctg aat cct gcc aat acc cgc agc      960
His Ile Thr Thr Glu Ile Val Met Leu Asn Pro Ala Asn Thr Arg Ser
305                 310                 315                 320

att tcc aac atg aca tcc cag gaa ttt gtg gag aaa cta acc aag cga     1008
Ile Ser Asn Met Thr Ser Gln Glu Phe Val Glu Lys Leu Thr Lys Arg
                325                 330                 335

ctg aaa aga cac cct gag gag aca gga ggc ttc cag gag gca ccg ctg     1056
Leu Lys Arg His Pro Glu Glu Thr Gly Gly Phe Gln Glu Ala Pro Leu
            340                 345                 350
```

-continued

```
gcc tat gat gcc atc tgg gcc ttg gca ctg gcc ctg aac aag aca tct     1104
Ala Tyr Asp Ala Ile Trp Ala Leu Ala Leu Ala Leu Asn Lys Thr Ser
        355                 360                 365

gga gga ggc ggc cgt tct ggt gtg cgc ctg gag gac ttc aac tac aac     1152
Gly Gly Gly Gly Arg Ser Gly Val Arg Leu Glu Asp Phe Asn Tyr Asn
    370                 375                 380

aac cag acc att acc gac caa atc tac cgg gca atg aac tct tcg tcc     1200
Asn Gln Thr Ile Thr Asp Gln Ile Tyr Arg Ala Met Asn Ser Ser Ser
385                 390                 395                 400

ttt gag ggt gtc tct ggc cat gtg gtg ttt gat gcc agc ggc tct cgg     1248
Phe Glu Gly Val Ser Gly His Val Val Phe Asp Ala Ser Gly Ser Arg
                405                 410                 415

atg gca tgg acg ctt atc gag cag ctt cag ggt ggc agc tac aag aag     1296
Met Ala Trp Thr Leu Ile Glu Gln Leu Gln Gly Gly Ser Tyr Lys Lys
            420                 425                 430

att ggc tac tat gac agc acc aag gat gat ctt tcc tgg tcc aaa aca     1344
Ile Gly Tyr Tyr Asp Ser Thr Lys Asp Asp Leu Ser Trp Ser Lys Thr
        435                 440                 445

gat aaa tgg att gtt ata tcc aga act cac agc cca acc tga             1386
Asp Lys Trp Ile Val Ile Ser Arg Thr His Ser Pro Thr
    450                 455                 460


<210> SEQ ID NO 57
<211> LENGTH: 461
<212> TYPE: PRT
<213> ORGANISM: Homo sapiens

<400> SEQUENCE: 57

Met Gly Pro Gly Ala Pro Phe Ala Arg Val Gly Trp Pro Leu Pro Leu
 1               5                  10                  15

Leu Val Val Met Ala Ala Gly Val Ala Pro Val Trp Ala Ser His Ser
            20                  25                  30

Pro His Leu Pro Arg Pro His Ser Arg Val Pro Pro His Pro Ser Ser
        35                  40                  45

Glu Arg Arg Ala Val Tyr Ile Gly Ala Leu Phe Pro Met Ser Gly Gly
    50                  55                  60

Trp Pro Gly Gly Gln Ala Cys Gln Pro Ala Val Glu Met Ala Leu Glu
65                  70                  75                  80

Asp Val Asn Ser Arg Arg Asp Ile Leu Pro Asp Tyr Glu Leu Lys Leu
                85                  90                  95

Ile His His Asp Ser Lys Cys Asp Pro Gly Gln Ala Thr Lys Tyr Leu
            100                 105                 110

Tyr Glu Leu Leu Tyr Asn Asp Pro Ile Lys Ile Ile Leu Met Pro Gly
        115                 120                 125

Cys Ser Ser Val Ser Thr Leu Val Ala Glu Ala Ala Arg Met Trp Asn
    130                 135                 140

Leu Ile Val Leu Ser Tyr Gly Ser Ser Ser Pro Ala Leu Ser Asn Arg
145                 150                 155                 160

Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
            180                 185                 190

Ala Thr Ile Gln Gln Thr Thr Glu Val Phe Thr Ser Thr Leu Asp Asp
        195                 200                 205

Leu Glu Glu Arg Val Lys Glu Ala Gly Ile Glu Ile Thr Phe Arg Gln
    210                 215                 220

Ser Phe Phe Ser Asp Pro Ala Val Pro Val Lys Asn Leu Lys Arg Gln
```

-continued

```
225                 230                 235                 240

Asp Ala Arg Ile Ile Val Gly Leu Phe Tyr Glu Thr Glu Ala Arg Lys
                245                 250                 255

Val Phe Cys Glu Val Tyr Lys Glu Arg Leu Phe Gly Lys Lys Tyr Val
            260                 265                 270

Trp Phe Leu Ile Gly Trp Tyr Ala Asp Asn Trp Phe Lys Ile Tyr Asp
        275                 280                 285

Pro Ser Ile Asn Cys Thr Val Asp Glu Met Thr Glu Ala Val Glu Gly
    290                 295                 300

His Ile Thr Thr Glu Ile Val Met Leu Asn Pro Ala Asn Thr Arg Ser
305                 310                 315                 320

Ile Ser Asn Met Thr Ser Gln Glu Phe Val Glu Lys Leu Thr Lys Arg
                325                 330                 335

Leu Lys Arg His Pro Glu Glu Thr Gly Gly Phe Gln Glu Ala Pro Leu
            340                 345                 350

Ala Tyr Asp Ala Ile Trp Ala Leu Ala Leu Ala Leu Asn Lys Thr Ser
        355                 360                 365

Gly Gly Gly Gly Arg Ser Gly Val Arg Leu Glu Asp Phe Asn Tyr Asn
    370                 375                 380

Asn Gln Thr Ile Thr Asp Gln Ile Tyr Arg Ala Met Asn Ser Ser Ser
385                 390                 395                 400

Phe Glu Gly Val Ser Gly His Val Val Phe Asp Ala Ser Gly Ser Arg
                405                 410                 415

Met Ala Trp Thr Leu Ile Glu Gln Leu Gln Gly Gly Ser Tyr Lys Lys
            420                 425                 430

Ile Gly Tyr Tyr Asp Ser Thr Lys Asp Asp Leu Ser Trp Ser Lys Thr
        435                 440                 445

Asp Lys Trp Ile Val Ile Ser Arg Thr His Ser Pro Thr
    450                 455                 460


<210> SEQ ID NO 58
<211> LENGTH: 1746
<212> TYPE: DNA
<213> ORGANISM: Canis familiaris
<220> FEATURE:
<221> NAME/KEY: CDS
<222> LOCATION: (1)...(1743)

<400> SEQUENCE: 58

atg ctg ctg ctg ctc ctg ccg ctg gcg ctg gcg ccg ctc ttc ctc cgc       48
Met Leu Leu Leu Leu Leu Pro Leu Ala Leu Ala Pro Leu Phe Leu Arg
 1               5                  10                  15

ccc ccg ggc gcg ggc ggg gca cag acc ccc aac gcc acc tcg gaa ggt       96
Pro Pro Gly Ala Gly Gly Ala Gln Thr Pro Asn Ala Thr Ser Glu Gly
            20                  25                  30

tgc cag atc ata cac ccg cct tgg gaa ggg ggt atc agg tac agg ggc      144
Cys Gln Ile Ile His Pro Pro Trp Glu Gly Gly Ile Arg Tyr Arg Gly
        35                  40                  45

ctg act cgt gac cag gtg aag gct atc aac ttc ctg ccg gtg gac tat      192
Leu Thr Arg Asp Gln Val Lys Ala Ile Asn Phe Leu Pro Val Asp Tyr
     50                  55                  60

gag att gag tat gtg tgc cgg gga gag cga gag gtg gtg ggg ccc aag      240
Glu Ile Glu Tyr Val Cys Arg Gly Glu Arg Glu Val Val Gly Pro Lys
 65                  70                  75                  80

gtc cga aag tgc ctg gcc aat ggc tcc tgg aca gat atg gac aca ccc      288
Val Arg Lys Cys Leu Ala Asn Gly Ser Trp Thr Asp Met Asp Thr Pro
                 85                  90                  95
```

-continued

```
agc cgc tgt gtc cga atc tgt tcc aag tca tat ttg gcc ctg gaa aat      336
Ser Arg Cys Val Arg Ile Cys Ser Lys Ser Tyr Leu Ala Leu Glu Asn
            100                 105                 110

ggg aag gtc ttc ctg acg ggt ggg gac ctc ccc gct ctg gat gga gcc      384
Gly Lys Val Phe Leu Thr Gly Gly Asp Leu Pro Ala Leu Asp Gly Ala
        115                 120                 125

cgg gtg gat ttc cgg tgt gac cct gac ttc cat ctt gtg ggc agc tcc      432
Arg Val Asp Phe Arg Cys Asp Pro Asp Phe His Leu Val Gly Ser Ser
    130                 135                 140

cgg agt atc tgt agt cag ggc cag tgg agc act ccc aag ccc cac tgc      480
Arg Ser Ile Cys Ser Gln Gly Gln Trp Ser Thr Pro Lys Pro His Cys
145                 150                 155                 160

cag gtg agc cga acg ccg cac tca gag cgg cga gcg gtg tac atc ggg      528
Gln Val Ser Arg Thr Pro His Ser Glu Arg Arg Ala Val Tyr Ile Gly
                165                 170                 175

gcg ctg ttt ccc atg agc ggg ggc tgg ccg ggg ggc cag gcc tgc cag      576
Ala Leu Phe Pro Met Ser Gly Gly Trp Pro Gly Gly Gln Ala Cys Gln
            180                 185                 190

ccc gcg gtg gag atg gcg ctg gag gac gtg aat agc cgc agg gac atc      624
Pro Ala Val Glu Met Ala Leu Glu Asp Val Asn Ser Arg Arg Asp Ile
        195                 200                 205

ctg ccg gac tac gag ctc aag ctc atc cac cac gac agc aag tgt gac      672
Leu Pro Asp Tyr Glu Leu Lys Leu Ile His His Asp Ser Lys Cys Asp
    210                 215                 220

cca ggc caa gct acc aag tac ctg tat gaa ctg ctc tac aac gac ccc      720
Pro Gly Gln Ala Thr Lys Tyr Leu Tyr Glu Leu Leu Tyr Asn Asp Pro
225                 230                 235                 240

atc aag atc atc ctc atg cct ggc tgc agc tct gtc tcc acg ctt gtg      768
Ile Lys Ile Ile Leu Met Pro Gly Cys Ser Ser Val Ser Thr Leu Val
                245                 250                 255

gct gag gct gcc agg atg tgg aac ctc att gtg ctc tcc tat ggt tcc      816
Ala Glu Ala Ala Arg Met Trp Asn Leu Ile Val Leu Ser Tyr Gly Ser
            260                 265                 270

agc tca cca gct ctg tcc aac cgg cag cgc ttt cct acc ttc ttc cga      864
Ser Ser Pro Ala Leu Ser Asn Arg Gln Arg Phe Pro Thr Phe Phe Arg
        275                 280                 285

act cat ccc tcg gcc acg ctc cac aac cct acg cga gtg aag ctc ttt      912
Thr His Pro Ser Ala Thr Leu His Asn Pro Thr Arg Val Lys Leu Phe
    290                 295                 300

gag aag tgg ggc tgg agg aag att gcc acc atc cag cag acc acc gag      960
Glu Lys Trp Gly Trp Arg Lys Ile Ala Thr Ile Gln Gln Thr Thr Glu
305                 310                 315                 320

gtg ttc aca tcg act ctg gac gac cta gag gaa cga gtg aag gag gct     1008
Val Phe Thr Ser Thr Leu Asp Asp Leu Glu Glu Arg Val Lys Glu Ala
                325                 330                 335

ggg att gag att act ttc cgc cag agc ttc ttc tca gat cct gcc gtg     1056
Gly Ile Glu Ile Thr Phe Arg Gln Ser Phe Phe Ser Asp Pro Ala Val
            340                 345                 350

cct gtc aag aac ctc aag cgc cag gat gcc cga atc atc gtg gga ctt     1104
Pro Val Lys Asn Leu Lys Arg Gln Asp Ala Arg Ile Ile Val Gly Leu
        355                 360                 365

ttc tat gag act gaa gcc cgg aaa gtg ttc tgt gag gta tac aag gag     1152
Phe Tyr Glu Thr Glu Ala Arg Lys Val Phe Cys Glu Val Tyr Lys Glu
    370                 375                 380

cgg ctc ttt ggg aag aag tat gtg tgg ttc ctc att ggg tgg tat gct     1200
Arg Leu Phe Gly Lys Lys Tyr Val Trp Phe Leu Ile Gly Trp Tyr Ala
385                 390                 395                 400

gac aat tgg ttc aag acc tac gac ccc tcc atc aac tgc aca gtg gat     1248
Asp Asn Trp Phe Lys Thr Tyr Asp Pro Ser Ile Asn Cys Thr Val Asp
                405                 410                 415
```

-continued

```
gag atg acc gag gct gtg gaa ggc cac atc acc act gag att gtc atg      1296
Glu Met Thr Glu Ala Val Glu Gly His Ile Thr Thr Glu Ile Val Met
            420                 425                 430

ctg aac cca gcc aac acc cgc agc atc tcc aac atg aca tcc cag gag      1344
Leu Asn Pro Ala Asn Thr Arg Ser Ile Ser Asn Met Thr Ser Gln Glu
        435                 440                 445

ttt gtg gag aaa ctg acc aag aga ctc aag aga cac cct gag gag aca      1392
Phe Val Glu Lys Leu Thr Lys Arg Leu Lys Arg His Pro Glu Glu Thr
    450                 455                 460

ggc ggc ttc cag gag gca ccg ctg gcc tat gat gcc atc tgg gcc ttg      1440
Gly Gly Phe Gln Glu Ala Pro Leu Ala Tyr Asp Ala Ile Trp Ala Leu
465                 470                 475                 480

gca ttg gcc ctg aac aag aca tct gga ggg agc ggc cgt tcg ggg gtg      1488
Ala Leu Ala Leu Asn Lys Thr Ser Gly Gly Ser Gly Arg Ser Gly Val
                485                 490                 495

cgc ctg gaa gac ttc aac tac aac aac cag acg atc aca gac caa atc      1536
Arg Leu Glu Asp Phe Asn Tyr Asn Asn Gln Thr Ile Thr Asp Gln Ile
            500                 505                 510

tac cgc gca atg aac tcc tcg tcc ttt gag ggt gtc tct ggc cac gtg      1584
Tyr Arg Ala Met Asn Ser Ser Ser Phe Glu Gly Val Ser Gly His Val
        515                 520                 525

gtg ttt gat gcc agc ggc tca cgg atg gcc tgg act ctg att gag cag      1632
Val Phe Asp Ala Ser Gly Ser Arg Met Ala Trp Thr Leu Ile Glu Gln
    530                 535                 540

ctg cag ggt ggc agc tac aag aag atc ggc tac tat gac agc acc aag      1680
Leu Gln Gly Gly Ser Tyr Lys Lys Ile Gly Tyr Tyr Asp Ser Thr Lys
545                 550                 555                 560

gat gac ctt tcc tgg tct aaa acg gac aaa tgg att gtt aca tcc aga      1728
Asp Asp Leu Ser Trp Ser Lys Thr Asp Lys Trp Ile Val Thr Ser Arg
                565                 570                 575

act ccc agc cca act tga                                              1746
Thr Pro Ser Pro Thr
            580


<210> SEQ ID NO 59
<211> LENGTH: 581
<212> TYPE: PRT
<213> ORGANISM: Canis familiaris

<400> SEQUENCE: 59

Met Leu Leu Leu Leu Leu Pro Leu Ala Leu Ala Pro Leu Phe Leu Arg
 1               5                  10                  15

Pro Pro Gly Ala Gly Gly Ala Gln Thr Pro Asn Ala Thr Ser Glu Gly
            20                  25                  30

Cys Gln Ile Ile His Pro Pro Trp Glu Gly Gly Ile Arg Tyr Arg Gly
        35                  40                  45

Leu Thr Arg Asp Gln Val Lys Ala Ile Asn Phe Leu Pro Val Asp Tyr
    50                  55                  60

Glu Ile Glu Tyr Val Cys Arg Gly Glu Arg Glu Val Val Gly Pro Lys
65                  70                  75                  80

Val Arg Lys Cys Leu Ala Asn Gly Ser Trp Thr Asp Met Asp Thr Pro
                85                  90                  95

Ser Arg Cys Val Arg Ile Cys Ser Lys Ser Tyr Leu Ala Leu Glu Asn
            100                 105                 110

Gly Lys Val Phe Leu Thr Gly Gly Asp Leu Pro Ala Leu Asp Gly Ala
        115                 120                 125

Arg Val Asp Phe Arg Cys Asp Pro Asp Phe His Leu Val Gly Ser Ser
    130                 135                 140
```

-continued

```
Arg Ser Ile Cys Ser Gln Gly Gln Trp Ser Thr Pro Lys Pro His Cys
145                 150                 155                 160

Gln Val Ser Arg Thr Pro His Ser Glu Arg Arg Ala Val Tyr Ile Gly
                165                 170                 175

Ala Leu Phe Pro Met Ser Gly Gly Trp Pro Gly Gly Gln Ala Cys Gln
            180                 185                 190

Pro Ala Val Glu Met Ala Leu Glu Asp Val Asn Ser Arg Arg Asp Ile
        195                 200                 205

Leu Pro Asp Tyr Glu Leu Lys Leu Ile His His Asp Ser Lys Cys Asp
    210                 215                 220

Pro Gly Gln Ala Thr Lys Tyr Leu Tyr Glu Leu Leu Tyr Asn Asp Pro
225                 230                 235                 240

Ile Lys Ile Ile Leu Met Pro Gly Cys Ser Ser Val Ser Thr Leu Val
                245                 250                 255

Ala Glu Ala Ala Arg Met Trp Asn Leu Ile Val Leu Ser Tyr Gly Ser
            260                 265                 270

Ser Ser Pro Ala Leu Ser Asn Arg Gln Arg Phe Pro Thr Phe Phe Arg
        275                 280                 285

Thr His Pro Ser Ala Thr Leu His Asn Pro Thr Arg Val Lys Leu Phe
    290                 295                 300

Glu Lys Trp Gly Trp Arg Lys Ile Ala Thr Ile Gln Gln Thr Thr Glu
305                 310                 315                 320

Val Phe Thr Ser Thr Leu Asp Asp Leu Glu Glu Arg Val Lys Glu Ala
                325                 330                 335

Gly Ile Glu Ile Thr Phe Arg Gln Ser Phe Phe Ser Asp Pro Ala Val
            340                 345                 350

Pro Val Lys Asn Leu Lys Arg Gln Asp Ala Arg Ile Ile Val Gly Leu
        355                 360                 365

Phe Tyr Glu Thr Glu Ala Arg Lys Val Phe Cys Glu Val Tyr Lys Glu
    370                 375                 380

Arg Leu Phe Gly Lys Lys Tyr Val Trp Phe Leu Ile Gly Trp Tyr Ala
385                 390                 395                 400

Asp Asn Trp Phe Lys Thr Tyr Asp Pro Ser Ile Asn Cys Thr Val Asp
                405                 410                 415

Glu Met Thr Glu Ala Val Glu Gly His Ile Thr Thr Glu Ile Val Met
            420                 425                 430

Leu Asn Pro Ala Asn Thr Arg Ser Ile Ser Asn Met Thr Ser Gln Glu
        435                 440                 445

Phe Val Glu Lys Leu Thr Lys Arg Leu Lys Arg His Pro Glu Glu Thr
    450                 455                 460

Gly Gly Phe Gln Glu Ala Pro Leu Ala Tyr Asp Ala Ile Trp Ala Leu
465                 470                 475                 480

Ala Leu Ala Leu Asn Lys Thr Ser Gly Gly Ser Gly Arg Ser Gly Val
                485                 490                 495

Arg Leu Glu Asp Phe Asn Tyr Asn Asn Gln Thr Ile Thr Asp Gln Ile
            500                 505                 510

Tyr Arg Ala Met Asn Ser Ser Ser Phe Glu Gly Val Ser Gly His Val
        515                 520                 525

Val Phe Asp Ala Ser Gly Ser Arg Met Ala Trp Thr Leu Ile Glu Gln
    530                 535                 540

Leu Gln Gly Gly Ser Tyr Lys Lys Ile Gly Tyr Tyr Asp Ser Thr Lys
545                 550                 555                 560
```

```
Asp Asp Leu Ser Trp Ser Lys Thr Asp Lys Trp Ile Val Thr Ser Arg
            565                 570                 575

Thr Pro Ser Pro Thr
        580


<210> SEQ ID NO 60
<211> LENGTH: 15652
<212> TYPE: DNA
<213> ORGANISM: Homo sapiens
<220> FEATURE:
<221> NAME/KEY: misc_feature
<222> LOCATION: (1)...(15652)
<223> OTHER INFORMATION: n = A, T, G, or C
<221> NAME/KEY: misc_feature
<222> LOCATION: (1)...(15652)
<223> OTHER INFORMATION: r = G or A; y = T/U or C; m = A or C;
      k = G or T/U; s = G or C; w = A or T/U;
      b = G, C, or T/U; d = A, G, or T/U;
      h = A, C, or T/U; v = A, G, or C
<221> NAME/KEY: exon
<222> LOCATION: (3419)...(3444)
<221> NAME/KEY: intron
<222> LOCATION: (3445)...(3908)
<221> NAME/KEY: exon
<222> LOCATION: (3909)...(3993)
<221> NAME/KEY: intron
<222> LOCATION: (3994)...(4694)
<221> NAME/KEY: exon
<222> LOCATION: (4695)...(4898)
<221> NAME/KEY: intron
<222> LOCATION: (4899)...(5652)
<221> NAME/KEY: exon
<222> LOCATION: (5653)...(5838)
<221> NAME/KEY: intron
<222> LOCATION: (5839)...(7184)
<221> NAME/KEY: exon
<222> LOCATION: (7185)...(7205)
<221> NAME/KEY: intron
<222> LOCATION: (7206)...(8310)
<221> NAME/KEY: exon
<222> LOCATION: (8311)...(8806)
<221> NAME/KEY: intron
<222> LOCATION: (8807)...(12271)
<221> NAME/KEY: exon
<222> LOCATION: (12272)...(12406)
<221> NAME/KEY: intron
<222> LOCATION: (12407)...(12820)
<221> NAME/KEY: exon
<222> LOCATION: (12821)...(12991)
<221> NAME/KEY: intron
<222> LOCATION: (12992)...(14089)
<221> NAME/KEY: exon
<222> LOCATION: (14090)...(14191)
<221> NAME/KEY: intron
<222> LOCATION: (14192)...(14477)
<221> NAME/KEY: exon
<222> LOCATION: (14478)...(14543)
<221> NAME/KEY: intron
<222> LOCATION: (14544)...(15002)
<221> NAME/KEY: exon
<222> LOCATION: (15003)...(15194)
<221> NAME/KEY: intron
<222> LOCATION: (15195)...(15652)

<400> SEQUENCE: 60

gatcatatta atttgaaggt ggcggggcag gatggttctg tggtgcagtt taagattaag     60

aggcatacac cacttagtaa actaatgaaa gcctattgtg aacgacaggg attgtcaatg    120

aggcagatca gattccgatt cgacgggcaa ccaatgaaac agacacacct gcacagttgg    180

aaatggagga tgaagataca attgatgtgt tccaacagca gacgggaggt gtctactgaa    240

aagggaacct gcttctttac tccagaactc tgttctttaa agaccaagat tacattctca    300

attagaaaac tgcaatttgc ttccaccaca tcctgactac taccgtatag ttttctctat    360
```

-continued

```
tctttcattt ccccttccc cattccttta ctgtacataa agtaactggt atatgtgcac    420
aagcatatta cttttttttt ttaaaactaa acagccaatg gtatgttttg attgacatca    480
agttggagac ggggggggaaa atactgattc tgtgaaaata ccccctttct ccattagtgg    540
catgctcatt cagctcttat ctttatattc cagtaagtta ttttgctctc actgttttaa    600
caacaacaac aaaaaaacaa caacataaaa atccttgcat accttgttca attggagaat    660
tttaatgttt ttcatttatc attgtaaaac caaggacaat tttataactt ttttgtactt    720
agctgttaca tgcagagcaa tctgtcttta agtagggata aattactcta aaacaaaaaa    780
gaatcctaga tagttttccc ttcaagtcaa gcgtcttgtt gtttaaataa acttcttgtt    840
taaaaaaaaa aaaagtaaaa aagaaaagtt atgcaacaat taatggccca gaggcaatcc    900
ttgttaacat tttgatgcat cttttagctg tttttttttt tttttttttt tttgactgag    960
tttgactctt gtcacccagg ctgaagtgca atggcatggc atgatcttgg ctcactgcaa   1020
cctccgcctc ccgggttcaa gtgattctcc tgcctcagcc tcctgagtag ctaggattac   1080
gggcatgcac caccatgcct ggctaatttt gtatttttag tagagttggg gcttctccac   1140
actggtcagg ctggtctcga actcccaacc tcaggtgata agggaagggg cactattgac   1200
atttatggtt ggggcagaag tgtaagatat tcttcaaagc actacctaca tgttgaagaa   1260
ttgttcctca cccagattct caaaagtccc ccaggacatt cacgtagtga aaacctgtgt   1320
ttaattatct gagcctataa cttaatacag ttttaaaatt tttttttaaa tatacagtga   1380
actttctagg aatgcaatta tagttgtgtg ttaaattagg gaaaattaac tttgctacca   1440
agagttgttc aacattttgt taaatcactt cattgatggc aacatgctgg aggtagttga   1500
gtcaccaact cagcacctgg atcagcctgt gttggtagca gtttcatccc cgtggttctg   1560
tgaataggtg gaagcatctg cttactccat caggacttct agggtagtcg ggccttggca   1620
ctcacacatt aaaatactgt ttatgttatt ttattgcaag ttacttttct ttcatttccc   1680
ctntacgtta cagaaaggga agcattttgc tttctgttta aagttgtgta tgtaggtagg   1740
ttatatcatc taagactttc tctccctcct tccctttctt tttgtttgag atggagtctt   1800
gctctgtcac ccaggctgga gtgcagtggt gcgatcttgg ctcactgcaa cctctgcctc   1860
ccgggttcaa gcgattctgg tgtctcagct gggattacag gcgcacacca tcacaccacg   1920
ctaatttttc tatttttagt agagatgggg tttcgccatg ctggccaggc caggctggtc   1980
tcaaactcct gagctcaagt gatcagtccg cctcggcctc ccaaagttct gggatttcag   2040
gcgtgagcyt catctatgaa tctcaattta ggacagtaaa agtgtcatwa caaaaatatt   2100
tattgtaaaa aagggttgga ggttgagaat ctcaattcta gtcagtctct cagtgtttgg   2160
tttcttccta ccatttttcc ccctaggacc agccagaaag cagctttttt tttgtccccc   2220
ccaacaagga gcccactgtt tcctctccca gcccaaactc aggcctacga acaacaacag   2280
cactacacac acacacacac acacacacac acacacacac acacccttcc atttcaaggt   2340
atagccaaga gcttctggag ccgtcaaaaa ggtctgtacc tgctgtcttt agagcttcca   2400
gtttgccctt ggtcaagaaa tactgtttgc taggctctgc tggagtacat caggtaatac   2460
tggcttctaa accaccctga ggttcttttc tcttgtcctt ttactccctt cgtacttcaa   2520
tttctctcct tgatgtcccc ctccctgttt tgttttttgc ctccaatccg ttctgcgcgt   2580
tccctgcaga gcaggcgagt agcaatgctg ctggaccatg gagctgctct agtctcccag   2640
aaatctcttc tacacccaac ccttcttgcg cttaggtggt cytcagtccc cctcccccac   2700
```

-continued

```
ttccttctga cccaggcttc tttctcgccc tccggtcgca gttctcctgg gcatctgcct   2760
ctgcctctct cctctcaccc ggatctaggg ctgctttctc tttgtgcagc cgtctttctc   2820
caccttcatc ccagactccc tgtctcagcg ccagctcctc tgcctttggc tcgggttccc   2880
tctcccccac cccagcttcc agttgtttgg cccgcaggtc cctcggcagt gaccggcgcc   2940
ccccgacgag tgcgtgtgca ccagggcacc tccctctccc ccacctctca gccccgcgcc   3000
tctccaccgc ccgccccacc gcgctgtggg cggtccaggg cggggctggg atccggggcg   3060
gctcccgggg ctcgggttgt gggaggcgcc ctctccccgg tcttcccctc ttcttccccc   3120
cgccctgcct tcccttgcac cctccttctt ccctccgccc gggagctctc cctggtcccc   3180
cggcgccgcc tccttccctc ccggctcccc gctccccgct cccgtggctg ccgccgcccc   3240
ggggaagaag agacaggggt ggggtttggg ggaagcgaga gaggagggga gagaccctgg   3300
ccaggctgga gcctggattc gaggggagga gggacgggag gaggagaaag gtggaaggag   3360
aagggagggg ggagcgggga ggagcggccg ggcctggggc cttgaggccc ggggagagcc   3420
ggggagccgg gcccgcgcgc cgaggtaaga gccaagggcc ccgggttagc agggctcgga   3480
gagggggcgc scggcgtggt gggggagggg gcagtgggcg cagggcccag ctgggggaag   3540
cggggctggg ggagaggagg aaccgcgggg atggaatcgg ggagcgctga ggcggccgat   3600
gccgggagcg tgggtaagcc aggcttctgc gagccgcggg ggccggggga gaggaggtgg   3660
tgagaggtgg agtccgggag ggttggggcc cgagggaggc aggaggaggg tggggacagg   3720
ctttctctcc tcctctcccc ccaccccgcg cggggctccg cccccgcctc ctccgcgggg   3780
cgctctcttg gtccccaggc tgagcccggt cggagcctgc gaggcaaccg gcaagaggtc   3840
gagtagtctc cgggtgcggg ccgcgccggc ggggctcggt ccagtcctca tggccgcctc   3900
tcacttagat gttgctgctg ctgctactgg cgccactctt cctccgcccc ccgggcgcgg   3960
gcggggcgca gacccccaac gccacctcag aaggtgcatc cttcttcgac gacctccggc   4020
cctccttcgc tccacttccc tttccctgca tctcctcatt tctggtcctc atcactatcc   4080
catcagtccc acatatcatc ccggnctggc aacccccttct gctcggnccg actttactac   4140
tgctgacctc cttctgtcac cccacgttac tatccagcac ctcttttctc tgcccacatt   4200
gctacactat accaccttcc tgtgcatttt ctccgcctca atccccttc ccagccccac   4260
attamtacyt caattactcc cttttcttgg tcccactttg ctgtccarat gatcttatwa   4320
gcctcccttt atcytcctat cctaattcaa ytsgaatatc ctcatttagc cttttttttt   4380
aaagaaaagc tccacccaca tatcataccc ttcatgattt cttaattact tttctttctt   4440
acytccaccc agcacccttc cytccccact ngtgggttct ctcatcagct ttaaccctgg   4500
ccctttactc tytgtccttt agccagggga tntgtacctg tccccactcc caccctctag   4560
tgccccatcc ctcttcctct gtccccagcc tgcccacaga ccacgcccta ctctcccctt   4620
cctcccaskg gggagcskgc cttttcytct ttcccaccat tcctctctgt atgcctcccc   4680
gactcacccc ttaggttgcc agatcataca cccgccctgg gaagggggca tcaggtaccg   4740
gggcctgact cgggaccagg tgaaggctat caacttcctg ccagtggact atgagatkga   4800
gtatgtgtgc cggggggagc gcgaggtggt ggggcccaag gtccgcaagt gcctggccaa   4860
cggctcctgg acagatatgg acacacccag ccgctgtggt gagtagcctc ggaagcccct   4920
cccctcttca agactattcc ttttcctgcc gcaaacttag cattactgct tgcaagtcag   4980
cactttaaat ccagtatacc aaaattcaca aatacattta ttgaatgact actacataag   5040
agcaattttg ctctgtgcgg ttggaggtag tagagctagc agcctgcaca gttcatttca   5100
```

-continued

```
tcctcccttc attaggccac tgatcattgg cctataacat tgataattca tcttgtcagt   5160
tattctcttk gaggatcatt agtggcagat gatgacaaaa aaaattctaa aatgatttca   5220
tcacattttt gaataccttc tgtcaccaac ccagagacca tatgcccaag aaacaaaagc   5280
cagtttaata ttaatagaag ccaactataa taagaaaagc aaatctgatt gtgcatccaa   5340
agttatatac atctacatat ttcaaagcca gagaaccgcc cactgtagct gactttgaag   5400
agatcccatt ttgtgtgctt atagccccat cttgggttcc taaaatggta attttttttt   5460
tcttttggga atgtgtggat gcttgcacag gtaagggagg attggaagat aggtaggcaa   5520
atccttttca catgtgattt tctttagagc aggatgcttg tggacccaaa cctgcamctg   5580
agtcccctgy tctttaaagg gaaagagcct tcttcaaytc gcctytcttc ttattttccw   5640
atctctccac agtccgaatc tgctccaagt cttatttgac cctggaaaat gggaaggttt   5700
tcctgacggg tggggacctc ccasctctgg acggagcccg ggtggatttc cggtgtgacc   5760
ccracttcca tctggtgggc asctcccgga gcatctgtag tcrgggccag tggagcaccc   5820
ccaagcccca ctgccagggt gaggggaaca gctgcctgca tgcagctgat gaggacsctt   5880
gtgtgaggat gggagtgggg tgggaatgga taatgggaaa raatggarag ctataaaawt   5940
gtgggggagg acactggaaa ggggagatra aagtcccttt ttcctccatc acctgcctca   6000
aacttcctct tgcagtcccc ggtatcctct gtwggtkggg ggcttccttc ctttaccttt   6060
taaaaaaatc ttcctgctcc cgattcttag accycacgtt ttctcttttc ctttatgaat   6120
ctcacctctc tcaccttctt caggtttaaa tactccaatt ttccctttct ctaaacttag   6180
aaatttccat gcatcaccct cttctagaat ycctcaccat tccttatata attgatttat   6240
tgtaaagact cagaaataaa tcaaacattc tactaagaaa aattgagaag gggagctctg   6300
ggggtggaaa catattaggg taaaagactt aaaattggag gcagcattat cagaagatga   6360
agaacaactc agggatgggg tgggaagaag acaggtcctt ttctgtactt cctagacaac   6420
ctccattatt ccctaaggga atcagtgttg tgtctgtcta cttttttttt ttttttttg    6480
ccacgtnatt ttacaaactc tccctttttct aggcacccga actctctgcc atcttctctc   6540
ctgggakgca gtcatcccat ttgtatgcyt cawacttcyt ctaccctggt agattctttc   6600
aagatccttg ggctttwactt tcctcacata actcagttat tctgcttcta gtttaccatt   6660
ttattctgga aattgagagt cccatccagg ggtggactta tgacactact gaaacttaga   6720
cttcaaggtt cctcacctac agggccytct tcctgtgctc taataatata garggctcga   6780
tggatatgtg ttcatatggt aacaggcttt tgtwaaaatt gcagaaataa gattttaaca   6840
gcmattgctt aaagccmawt gtatgtgtwa ttttttttct taaagactcc cmattttgtw   6900
atattcaggc mccmcagaac caagatctgc cccaaactta gctattggca ttcccgtctc   6960
aaattctgtt gtcctatgaa aaatcgaaga agaaaataag tcctgacccc cttaccccca   7020
gacccacctt gttcttatcc ccaggcaccc tcccctcaga aacgcaggct tctgctctcc   7080
ccggtcttca gcatggacag gtgtgggagg gggctgggga tcaggccagg gaagctgggc   7140
gccagtggta actcttctct gatccccgtc tttcctgctg ccagtgaatc gaacgccaca   7200
ctcaggtgag atgagaaacc cttaccgcgc gcactgcaat gccctcccct tcactctgca   7260
ccctccaccc ccctgaaatt ctgcccttag gctacggggc gtcgtccttt cgcaccttcc   7320
ccaacccacc ccaktttgcg gccaccccct tccctcccta cctgtttcct gcctccagtc   7380
ccggttttcc acraggctgc ggtctctcct tgtccctgct tggctacact tccctgggct   7440
```

-continued

```
ccacctcctc ccagactgag cctcgccggt gtcaggcaga gcccancara aggcggcagg   7500
gtgctgggag accctgagct cccaccacgt tttcccctgt ggggttcctt gcgaccttcg   7560
ctggaacctt ttccagcctg ctgcctccta ggatttcacc taatggactt tctcagcctg   7620
tyccacccat yccaaccctg gscaggcctc tcgcgctctt ccccacatct tttccttccg   7680
tgtacccttc cctcgtcttt tctcaattcc atgtcctgtc tccctttctt aaggyttctg   7740
tctacccagc cccaggytcc yttccacrac cccaccaytc cytcaaacca gcytcccttc   7800
cgtacccaac tcgttccctc caaaaccgtt tcctctcccc cacatcctca gtgcttcact   7860
gtatcgactc atactcccac ttcagacctc aggcgccagc cccgtttctc tcccgtccca   7920
ctcgcatcct tcccttccta ccctggttcc tccgtgcttc agcctcccgc ggctccctcc   7980
gcccaccccg ccytcytggc acgccccgtc cccatttctc ctcccctcgg gtccccttaa   8040
gtgagatccc tcccttcctc tttcgttcct ttcctcctcg aggttgcatc ccccctcccc   8100
tccccgcccc tccgactgtc gctcccacct cggcgctcgc ttccctcccc gccccccttcc  8160
tgcctcccca gctcccgccc gcccccccac cccccgctgc cgcgcgccgc ccgtgacgtc   8220
agagcccccct cccagcccca catctccctc ctgctcctcc tcctcccctc cgtcggtcag  8280
tcagtccgcg aggagagtcc gcggtggcgg cgacggtggc gagagccgcg ggggccgtag   8340
gaagccaacc ttccctgctt ctccggggcc ctcgccccyt cctccccaca aaatcaggga   8400
tggaggcgcc tccccggcac chtcttagca gccctccccg ggaaaagtgt ccccccctgag  8460
ctcctaacgc tccccaacag ctacccctgc cccccacgcc atggggcccg gggccccttt   8520
tgcccgggtg gggtggccac tgccgcttct ggttgtgatg gcggcagggg tggctccggt   8580
gtgggcctcc cactcccccc atctcccgcg gcctcactcg cgggtccccc cgcacccctc   8640
ctcagaacgg cgcgcagtgt acatcggggc actgtttccc atgagcgggg gctggccagg   8700
gggccaggcc tgccagcccg cggtggagat ggcgctggag gacgtraata gccgcaggga   8760
catcctgccg gactatgagc tcaagctcat ccaccacrac agcaaggtas ccctrgacat   8820
gggggtgggt gggakgtggg gscttgcggg gcaggggggcc aagcaagctt gcacgcgccc  8880
ccatctgtct gagtcgtctc tgggattgcg aggcagaccc ctcccttgtg tgactggcag   8940
gagatgggct gggggtgcag gagcttggga agagtcgcag gggctggagg tccaagatga   9000
gggtctaggg gctcaagatg gttaagcatg ctgcaaggca gacccttctg ccccgctgcg   9060
ggagtctcgc agaagtgtcg gggtttggag aaactggtgg tggatttaag gtattaggag   9120
acactgatcc tctgagggag taaactaacc ctggaatggg ttgggggtgg agggaatgtc   9180
agaggtgggg agctggattg gggggttaca tttaccatgg taacaaggta aaatcttggc   9240
gtaggttgga gctggaagga atagggacag aatgaggaaa attttgagag acttgagagc   9300
tctagtttat ttatcttaac aaaacagcaa ggtagtggtg agccctacct gactccttct   9360
catccttcta ttcccaaccc tgttgagcat tcccagactg tgggatagat ggcatatggt   9420
gattggggaa ggctaatgat caagaggtgg gcagaggcac tgggaaaatg aattggattg   9480
gggatccaca tgggaacccc cacaatagca tggggatgaa gaagagtcaa catacaagga   9540
gaagagaaca gaaaagaatg gcagtggggg agaggggcaa ggaggtagcg tggggataat   9600
gagagatctt ggggcacctt atggaacttg ggtcctgacc ttcccttccc ttatagcatt   9660
gtggcctcta ggatgtgaga agggaaatgg gatgtaggga ttagggaggt gagttgaggg   9720
agagagagaa ggtaagcaaa tttgggtcca ggggtattag gggatagctt ataatgaggt   9780
ttttttccc acccctctcc cctacatgaa taattggggg tgcagggaag gatgtgacac   9840
```

-continued

```
agggaaggag atttaagatc tcaaatttat cttcactgac atgtggcccc agagacttaa   9900
ggaattgggt tagggtgaaa tagagtacac aaggtgagaa tttggtgatc ttaccaaata   9960
tcaaccttgg ggtgatccaa ggatttatat tcatttttag aacatcacta tacacctaga  10020
aataggtgtg tgtctgggat aggtgtgtga ggggacagaa gtgaggttga aggtagggtg  10080
cttgaagaga agagagcaca aggattatca ggagcttggc aagagaactt aaaatccttt  10140
ttgactgtta ctttctcgtg gttctcagcc ttcagtgtac ataagaatca ccagaggagt  10200
ttgttaaaaa tacagattct agctccttgt tcagggatga atcccaagta tttatctgta  10260
tttttactaa tagacatccc tatcttggtg gattcctgag ctgtaagcta accccagaat  10320
gcctatggga agagcagcag ggtacaggaa aataattagg tattagggta cgggaggcag  10380
gaagagaagt agaggatcag atctggtaga gggtcagact tgggacagtc agagagatca  10440
ttggttttgg ggagtggagt gtgaagaaaa tgacagggag agatgggtgc aggctttatg  10500
ataggggatc acaggagata ggggaggcct ggctgtgagc tcaaactcat ccaccatgac  10560
aggtgattcc ctggaggtgg cggggagcag acgtgggacc tgggagaagg gaactggaga  10620
acatcagagg catcaagcgg ggtgggatgg gaaggcagaa gaaccagaat gtgtcaattg  10680
gaatgagtcg gtttcctgcc tgcaaatcca gatccttgca agagcaaaga gagggaggag  10740
aactaaggaa atctattggg gagggggaga gaatcacgtg gtggagagaa tctgcagtga  10800
tgaatagtgt gtggaagagg gaaacggttg caagaaaagg tagataagaa atcaggaaac  10860
aaaatggggg gcatgcctgg ccctgttgat aggtatctta tatgttcttg aatgtcctca  10920
ttgttcnnat taacccctgt ctttagagaa gtggaggggc actgaggggc tgtgggagaa  10980
gctgggagca ggatctggag taatagatgt ggggagagtg caggaaggtg ggtcctgaga  11040
atggtaaaga tttacaaagt tgccctagtg ggaggcataa agagaaaacc ttccaatgtt  11100
gttgagcact gcccttggcc agagtgaggg tagggtgggc aacagagaat tctcagtgac  11160
tgctggttct tcagattcca acagcttccc ctggctcccc cttctccaac ttcccaccgt  11220
gtcccaaatg tcaggcctca gtgggaggta agcaggctcc agagtgcttt ctttatttcc  11280
tttctactta tcctcccctc ctggcaacat ttcaccctcc ttagtcccct gagccccctg  11340
tctgtgtccc ctctgccctg gctccccact ggctgccatt tcgtcttcac atgcattggg  11400
gttccagcag cttctgaaat gtcatatatc agtgggaggg gaacaggcag tgggagaccc  11460
aaggctggct cttcctcccc catttcccct cctcccaagc ttcctttctt ctccagcttt  11520
ctgcttgttt actttcccta gctccaagcc tctctttaag gcacctctca aattgtctgg  11580
tttcttgaga gttccattct attcattctc tctgttcttt cctcatccta cattcttccc  11640
tacttccacc ccccagtgtc tttttttcta atggacctgt caaatgtcag cgcccagcag  11700
gagggatgga tcactgagcg ggacccccta ctggtcttgt tcctgttctc tcttwactta  11760
tcactagctc tgaaaagaga agagggagga aacaaatgga aggtggggag aaggggtttg  11820
cagaggtgag gaaggaattt tcataatatg gctttgagca agctatctgg ggatgtggaa  11880
agagtttacc gtattcctac tgacttcttc cacccactgg tgtttgaagc atagaaacat  11940
ggggtaaagg gcttggtgac agagggaagg gggatgtctg agggtgagct gaaaggaggt  12000
aaggtggtat gttcattaat accaaaggag gggtgtgcag gagaggtgat gggtaaggct  12060
ccagatggaa gacagagaag gaagtttaat gaaagargag aaaaaaggca cttgacagga  12120
agagatgcca gaaaggagaa gaaaacggta attaatgatg aaagtgagta attgagaaag  12180
```

-continued

```
gaactaattt gttcgagaaa gataagagca ggaattgcag acaggggagg ggccccagga  12240
gagcttgccc tcatctcctc ttgtctttca gtgtgatcca ggccaagcca ccaagtacct  12300
atatgagctg ctctacaacg accctatcaa gatcatcctt atgcctggct gcagctctgt  12360
ctccacgctg gtggctgagg ctgctaggat gtggaacctc attgtggtaa gcagggctat  12420
gggggtcaga agatggggtc attccctttt gagctctact gaagggacga tggcgattgt  12480
gggtttgtat tgaaaaggag tgtggaggac ctgctactaa gattcagagt cctctgcaga  12540
cctgagctag gcagcytcct agcaacagtg scctgacagt gctgcagctg acctccttct  12600
tcagaaggaa ttgaaattag atcagtgaaa gagcatcccg gttgtgaggg gtgtgtgggc  12660
ctttgagaat ctcttttcct taggcagacc agaggtgggg aggtttggag agagtaagga  12720
agagaaaccc aaaggcagga agagggttaa aggaactctt ggccactctt ggtgtcctca  12780
gtgaacagac cctgttgcac tcactctccc tgccccacag ctttcctatg gctccagctc  12840
accagccctg tcaaaccggc agcgtttccc cactttcttc cgaacgcacc catcagccac  12900
actccacaac cctacccgcg tgaaactctt tgaaaagtgg ggctggaaga agattgctac  12960
catccagcag accactgagg tcttcacttc ggtgaggagg ggttgggcaa ggggtaaagg  13020
gacataagct caaattccag caccaggaga tgtgacgtga gagtcacttt taggggcaag  13080
aacttgattc ttcattgaaa gagaacgcat tccatgtgga ttaagtgcag ttctttctgt  13140
agccagggga aagaatgagt tgagtttttg ggatcctctc tgtctttatg attttatgat  13200
ttttttcccc tgtttgatgc cctgttcccc agacatatag acccagaatg actcagttct  13260
gttaaagtag gttcaatcca aagtgggggc aagagatggg agcgaagatg agataggaat  13320
ccaggaaggc agcagattcc agaagctttc aagggggggtg gtgggtgggt gttaatggga  13380
acagaaggga tggagccagt ggattacmga rgagagaggg rgagraagag agagagagag  13440
aggaatgagg gagaggagag agaggggcag aaaggcagct gcatggatct ggtagttggt  13500
actaagagag agaagccgac agacaaggag aggttgaggg ggaagaggga gatttgggga  13560
ggtagagagg aaatacaggc tctacatctg aagaaggcag tctgctccct cccttttatt  13620
ctattctttg ggtcttctat ccactgtgtt cagtggccct ttaatcctcc cccactttca  13680
ctctgattca gaccattctt ctctgatcct ttgtctgtct gcccatttgc ctcttgaggt  13740
agacatcatg ctgtctgtcc cagtccttgc cttgtctttt cctggttcct ttatgtttct  13800
ttaccccatc tttgccttca gtggtaggag tgggtgaatg gagtggcttc ccccacacag  13860
agcctcagca ggggctcacc attcaccttc ccacttggaa tccacatcct aagaccagat  13920
gccttcccga actcctcact tcagggacag aagctgttga aggaaggttc agaatggctg  13980
cttctttgct ctatctgagt attgctctga aatccccagt taacctctct ggtctttatt  14040
ccctcatgca ccccgtgttt ttccaacttg ttttttattc ccacccaaga ctctggacga  14100
cctggaggaa cgagtgaagg aggctggaat tgagattact ttccgccaga gtttcttctc  14160
akatccagct gtgcccgtca aaaacctgaa ggtcagatgg ctgggagtgg tgggctctgt  14220
ttacggaggg accaagctgg gggacagtga ctggttggas aggaaagcca ggcgggggca  14280
ggttttgatt ctctgaggca atancatctc ctggggaagt ttagctccat cttccagttg  14340
acgtttattc actatacgtt gagcgttacc ctgcactaag cactttggga tgggaaatca  14400
aagctgtgaa gacatctggc ttagcccctc aggcattccc gggcatccct caggagctgt  14460
ttctttctct gttgtagcgc caggatgccc gaatcatcgt gggacttttc tatgagactg  14520
aagcccggaa agttttttgt gaggtggart tggatctgaa gagggagggg cactgggtgg  14580
```

```
gagtttccct tggttttctt gtggggcctc ctcttggcat ctgtgcctga gttgatagca  14640

tatgatctga ggtgacgatt cataggatgt ctctgtctgt tggctctgac tgcatccctt  14700

gtctgcacac acatgatact ttcttcagat ctcatttttc tactgctttg tgtttccyga  14760

gaagcccatg aattccatct gtcctgactg gctggaaaag gccactcaga aatacagggg  14820

ctggggagaa acttagaagg aagaattgtc agcctttcct actatcccca agacttgtag  14880

atttctcttt ttagttctac tgctcttccc tgattcccaa gaggctaaat agtatcaagt  14940

gagataagac aaaaacaaac aaatgagcaa acaaaaactc agccattctc ctctgtattc  15000

aggtgtacaa ggagcgtctc tttgggaaga agtacgtctg gttcctcatt gggtggtatg  15060

ctgacaattg gttcaagatc tacgaccctt ctatcaactg cacagtggat gagatgactg  15120

aggcggtgga gggccacatc acaactgaga ttgtcatgct gaatcctgcc aatacccgca  15180

gcatttccaa catggtgaga gtgtggggac ttgcagtctg gcacctggga gggtggagag  15240

gactgagggg sccttgcagg ggaaagggtg gcagggagag ggtgcggaat ttggatataa  15300

aggagaagag ggggctgtgc ccaccctgaa cttgtctgca ttatgtttcc tgtggatcct  15360

acctttgctc tgacttcctt gggtwgagag agaaaaaaaa aaaaacgatg gagttgtatg  15420

ttcagtaggt tcctgatgag tggaagggct gttaccatgg agacraggag cagttggtga  15480

gaagtcagga ggaaccggca ttaatgataa tatggatgct tgtwtactca agcacacctt  15540

tacaggagca ctgtgtctgg gcagaattgc atttcatttt cttggtgatt tatgttagtg  15600

ttttagagtt gcttaatatt cactcatgat tgatatgcma ttagcttgga tc          15652
```

```
<210> SEQ ID NO 61
<211> LENGTH: 13187
<212> TYPE: DNA
<213> ORGANISM: Homo sapiens
<220> FEATURE:
<221> NAME/KEY: misc_feature
<222> LOCATION: (1)...(13187)
<223> OTHER INFORMATION: n = A, T, G, or C
<221> NAME/KEY: misc_feature
<222> LOCATION: (1)...(15652)
<223> OTHER INFORMATION: r = G or A; y = T/U or C; m = A or C;
      k = G or T/U; s = G or C; w = A or T/U;
      b = G, C, or T/U; d = A, G, or T/U;
      h = A, C, or T/U; v = A, G, or C
<221> NAME/KEY: intron
<222> LOCATION: (1)...(1924)
<221> NAME/KEY: exon
<222> LOCATION: (1925)...(2167)
<221> NAME/KEY: intron
<222> LOCATION: (2168)...(2795)
<221> NAME/KEY: exon
<222> LOCATION: (2796)...(2859)
<221> NAME/KEY: intron
<222> LOCATION: (2860)...(4408)
<221> NAME/KEY: exon
<222> LOCATION: (4409)...(4486)
<221> NAME/KEY: intron
<222> LOCATION: (4487)...(6030)
<221> NAME/KEY: exon
<222> LOCATION: (6031)...(6181)
<221> NAME/KEY: intron
<222> LOCATION: (6182)...(6678)
<221> NAME/KEY: exon
<222> LOCATION: (6679)...(6811)
<221> NAME/KEY: intron
<222> LOCATION: (6812)...(8194)
<221> NAME/KEY: exon
<222> LOCATION: (8195)...(8311)
<221> NAME/KEY: intron
<222> LOCATION: (8312)...(8408)
<221> NAME/KEY: exon
```

<222> LOCATION: (8409)...(8516)
<221> NAME/KEY: intron
<222> LOCATION: (8517)...(8928)
<221> NAME/KEY: exon
<222> LOCATION: (8929)...(9022)
<221> NAME/KEY: intron
<222> LOCATION: (9023)...(9716)
<221> NAME/KEY: exon
<222> LOCATION: (9717)...(9844)
<221> NAME/KEY: intron
<222> LOCATION: (9845)...(10424)
<221> NAME/KEY: exon
<222> LOCATION: (10425)...(10553)
<221> NAME/KEY: intron
<222> LOCATION: (10554)...(10775)
<221> NAME/KEY: exon
<222> LOCATION: (10776)...(10919)
<221> NAME/KEY: intron
<222> LOCATION: (10920)...(11700)
<221> NAME/KEY: exon
<222> LOCATION: (11701)...(13187)

<400> SEQUENCE: 61
gaattcctga cctcaggtga tccaccctcc ttggcctccc aaagagctgg gattacaagt 60
gtgagccact gtgcccagcc tgacttgttt tttataatgc cttttttttt tttttttgag 120
acggagtctt gctctgtcgc ccaggctgga gtgtagtggc gtcatctcag ctcactgtaa 180
cctccacctc ctgggttgaa gtgattttct cacctcagcc ctcagcctcc tgagtagttg 240
ggactgcaag tgcacaccac catgcccagc taattttttg tattttagta gagatggggt 300
ttcaccatgt tgcccagctg gtctttaact cctgagctca ggcagtctgc ttaccttggc 360
ctcccaaagt gctaggatta aaggtgtgag ccactgtgcc tggccttttt tttttttttt 420
ttttttttga gcagttttag tttcccagca gaattgagat gaaggtacag aaacttccca 480
tatgcttccc acatgcatag ccttctacat tatcgacatc ctccgccaga gtggtacatt 540
tgttacaact gatgaaccta cattgataca tcataatcac ccaaagtcca tagtttacat 600
tagagttcac ccttggtgtt atatattcta tgggtttgga caaatgtata atgagacgta 660
tctactatta aatactttac agagtatttt cactggccta atccaatgga catttattgt 720
tacttcatta tggttgggca cagtgctaga tgctgatgat taagagaggg catgggattt 780
ggtcttgtcc tcaagggtag aacctaggcc cattgcatct tcaaagccca ggctccttca 840
aagcccagtg tagtagcaac tgctgtacct tgcctgtgcc ctttgcgtat ctcactcctc 900
tatctctcta gaaagttgga gagaaaagtg agcaaggcat gaggaacaaa gttatttatt 960
tattcttcat tcatctattt attctttcat taccgtttgt gttaaaacat tccaaaccca 1020
aacaattatt tgtatggtcc cctgtgtatt acttgtggtt tcccaagaag tagttgctaa 1080
gcttttcctt gtatggtttc tgtgaggtaa ggaaggaatg atgtgatttt ctccagtatg 1140
tagaatgcag ttccaagagg ttaagtaatt tacttacagt tatttagcca aacaaggtta 1200
ctgcaaggta tatgaagtca ggtctcttga cccagttcat gagagagtta aaggaactat 1260
cattcttttt agctttcatg gaaaaagaag gttgagtgtt gggaggggtg tgggtaggat 1320
tgataatgga cttcaaaaat gtgaagggta tttctgtagt tttcattctt ctgaaagcct 1380
tctaagaggc agtgaaccaa aagcacacaa gaatggcaag aagttagcat gctgaagaaa 1440
tatcctcctg gctggcaagc agagtgagaa gactgctatc accttttcta gaatcttttg 1500
gaattgtagg agctgttaga tcctgggtta actctatgaa gaaagtcaga aggatcagag 1560
aacatcagtg tcacagctct tcattggaat atccatgtct cctcctttac tctgctctac 1620
cttccatcct ttgccactaa ttatccagag tgtttgtcaa aattctctgt ttgcagttct 1680

-continued gagctagcaa ctgtacacac taacaccatc agacacagct aatacctact ctagtctagt 1740
agcttccgat ctaaggcaga cacatgggta tagttaaaga ttttgaatgt acatgtgtcc 1800
aatctgacaa cagtaacaca aaccatccat tcaagtagaa gtgattgagt cagaattgga 1860
ttgcacccct tcccccacac ccacacacat ttcagttctt tcctcatgat tttttcctcc 1920
caagacatcc caggaatttg tggagaaact aaccaagcga ctgaaaagac accctgagga 1980
gacaggaggc ttccaggagg caccgctggc ctatgatgcc atctgggcct tggcactggc 2040
cctgaacaag acatctggag gaggcggccg ttctggtgtg cgcctggagg acttcaacta 2100
caacaaccag accattaccg accaaatcta ccgggcaatg aactcttcgt cctttgaggg 2160
tgtctctgtg agttaaaact tccttcatac tcccctgtct tcccaatctt gagagagact 2220
cccaagaggc accttctaca aacatgcatt ctctgttttt ctcagttact tctttgcaga 2280
atcagtctcc gaccagagaa gtagggacct tcaaattaga agaacccatc aaagactaga 2340
ggaaaaaaaa tgatgtattc catttttttta aacccctccc ctcatttctt ttcaaactag 2400
accaagtatt catgagtcag atgagaacta taggattttg aaagacaaaa cagtctgaaa 2460
ggtcatcttc ttattccttt taaaatgaaa agattagttt ccagagagat ttgctgactt 2520
gcttaggcca cacaaccaga agcctgctgg tgttctgtct ggggattttt tcccattcaa 2580
atctcataag tgaagctcct tctccaaaga ataatgtttc taaaatctag ggtatgggca 2640
tctggggtat gtcctatatg caggcaaatg ccataaatag cattcattca gaggctcaat 2700
tacatcaaaa acagaaggat ttaaagagtc cctgatgttc tctttcactc ttgcttttgt 2760
ctcctttgcc ttgctccaca tgttccttcc ctcagggcca tgtggtgttt gatgccagcg 2820
gctctcggat ggcatggacg cttatcgagc agcttcaggg ttagtacagg ggcaggaggg 2880
gaccggacat gggggctagg ctggggctgg gctgggatgc cccctgggga agaatgccag 2940
agacatcaca agattgccct ggcacctccc aacttctgcc cttctctttt aactctgttc 3000
atcaagcttg taaataataa taataataag cttaactaca agaagattga tgtctttgag 3060
ttgcactggt tttgctcttg aaaagaggtg tgcaggctgg gtgtggtggc tcacccctgt 3120
aatcccagca cttttgggag gccaaggcag gcagatcatg atcatggtca ggagtttgag 3180
accagccaga ccaacatggt gaaacctgtc tctaccaaaa atacaaaaaa aaaaaaaaaa 3240
attagctggg tgtggtggca ggtgcctgta gtcccagcta cttgggaggc tgaggcagga 3300
gaatcacttg aacccaggag gcagaggttg cagtgagctg agatcacgcc actgcactcc 3360
agcctgggtg atagagtaag actctgtctc aaagaaaaaa gaaaagaaaa gagacatgca 3420
aattaaaaac agctactctc tttcccagtg gcttccatta atttcaggaa tttccccttg 3480
agtggcttgg gttgagaggt tgatgacctg tcagttagac tcaagaaagc tgaatctagg 3540
agaaccgcta tttttttttt aagggaatct gccaaatttc cttgctgtgt aaagcttcaa 3600
tgtgtatagc ttggcttttg tagattgtat tttcttgaaa cttagcacac aggtatttgc 3660
agaacttcta ggagttaatt tttctgctcc actcggctct cagtctttta cggcatggcc 3720
aagagagcta tttcttggcc tcctgtgaaa agtttctttc ttcctttctc cccacctcca 3780
catcctttca gctcctcttt gtatccagga caagaggaaa tggacttcag ccatggtgaa 3840
aggagtgtga gttggctttt gaaggaaaag ttatggtaac ggaaacagtt ctagaacaga 3900
aatcttagaa atgaccaaat tttactcaat ggcgctttaa gaggcagata taacttatcc 3960
aaggaattaa aacccaagcc aacagaagag aatgttctaa aattaaaatg aaagccactg 4020

-continued

```
ggaaaataga gcctgcccat catgagagga agaataagca gaaatatgtg taaagcttta   4080
gaagccaaam tcaaagtgag agacatctcg ccgagagagg tgtgaggaat ggaataggtg   4140
gcagacatgt tgtggagcct cctcactgaa gacttttaaa catagatatt cttatttatt   4200
tgagttgtct tgggaaccac cyyayattgc ttttaagtca tgttgctgat tcaagagtct   4260
cgtaggtcct tccaagcatc cttagggcct caggtgaaaa taaaatcaga tacaaccatg   4320
caaagctcta gggaagtggg aagttgaaaa tgcctaggat cagctctttg gctacctgtg   4380
gtcactcctt tyattgtcgt ctgcccaggt ggcagctaca agaagattgg ctactatgac   4440
agcaccaagg atgatctttc ctggtccaaa acagataaat ggattggtga gtggatcttg   4500
tttgtatttt ccttcagccc ctctcgacag tcaaggggaa aaagtcatgc ctttgagtga   4560
ggatggaatg gtagagactg ttaggttgga atgtggctgg cagctgggcc aggagaaagg   4620
gttaagtgag agtgaataca acccctaagg cgtgggtagg ggagactggt gtatttggag   4680
agggaatagg cggtggttag tactattttt aatggtgcat tgctggggta actggggatt   4740
agaggcaggg ggtgggcaga gggcgggaaa tggaaactcc atttgggttt cccagatgtc   4800
ctggtgtctt gatatatttg aaccagctac ttcaagccca gagctgtctc tttgtctgtc   4860
tctgtcagga aaacggttgc ttaaactatg gaggaggagg gaaaacctca tgtaattgtc   4920
atctgccaaa atgtgctttt tatttttata tgtattttta aaaattttcc tatttttatg   4980
taatttagag gtagacgtgc agttgtgtta catgaatata ttgcatagtg gtgaagtccg   5040
ggcgtttagt gtgcctgtca cccgaacagt gcaccttgta cctaataggt agtattacat   5100
ccctcaaaat atacttttta aagagagaaa gcaagcagtt attctttgtg tacttggtct   5160
aaatgatagg acataggaga gaaactgaag gtggacaaaa ggaaggacct actgataaaa   5220
gaaagcctcc ttgagaatga aggggaggct caaccattga agatggctgc cgtctgccct   5280
gcccagcaga tatccagtca ttcccagcac tgctggagtt ttgccctttt tttttttttt   5340
ttacaattcg aatttaggac aatgttctgg attgctataa atgctgcatg gcctaaatta   5400
ttctttaaaa aaaaactaag caaattgaaa ttagtttttt ttggtgaact ctgacaaatt   5460
gaacttcccc ctaataataa ctggaaaaca tatttgggaa tattaccctg ccaggattaa   5520
natttcagat kagctttcct tctttgtttg kttggtctta agaataggtg tccacactag   5580
atacttcaag gccttyttag ctttatgatt ccataattgt catttaaaam tttgatttgg   5640
gttataagaa accttataac attttttaak gatccccttc tttctcctcc cattttcctt   5700
tgctgtaaga aagacagaaa aacttaaaga acaaacaaaa acaaagacta caactttggg   5760
gacatgcctc agcatttccc aacctatgga tagaccattc actccatctt ctcatctcat   5820
ttctggttgc ttcctaacgg ccccagtggc actgagcatt ctgcctgcag taacctctgt   5880
ccagtgcagt tagggcctca tgtccccagc caatgactga atgtccatca gcaatctagt   5940
tctttgccct tttctcctat cccgtcttca ttcctttgtc ctccttccct tctcttttcc   6000
cttcccctct tcctcccctg tgccatgcag gagggtcccc cccagctgac cagaccctgg   6060
tcatcaagac attccgcttc ctgtcacaga aactctttat ctccgtctca gttctctcca   6120
gcctgggcat tgtcctagct gttgtctgtc tgtcctttaa catctacaac tcacatgtcc   6180
ggtnagtttc tcttctgacg ttttccttgt ctgcctctct gagatactga tcwtgtttcc   6240
tggacaggat gagaataaaa cctgkgtway tcccatggcc natgtatcat ggagtttttc   6300
attctgactt gttgagaatg aaaacaggga aaccagatat aacccccayt cctactccaa   6360
agtagctrrc gggaggaaaa aagaaaagaa gagaaaaaaa cmwcctttgg ggccaggtct   6420
```

-continued

```
cacagtcttg gactctacat aaatagcctg tattctagtg gggcctgtg cttgggaagc   6480
cytctgcaac tccatcttca gccccatgac tgcattgctc tgcctctcra ggctccactg   6540
tcttctccaa tcctgtcttc ctttagcccc tggccctgaa attagggtca tgccattgcg   6600
tggtatttgg agagctcagc ctccctggag aagaggggta attctctctc cctctcaccc   6660
tctccacctc tgccctagtt atatccagaa ctcacagccc aacctgaaca acctgactgc   6720
tgtgggctgc tcactggctt tagctgctgt cttscccctg gggctcgatg gttaccacat   6780
tgggaggaac cagtttcctt tcgtctgcca ggtgaggagg tggtgggcaa attccttaca   6840
ggatgtgact ctcccacccg tctcaggagc accttccatg atttatgatt ctctgccctt   6900
cctcctcagc tttccctgac tcttgtccct gttctttcct tctagcatca cccctctgtt   6960
ctctgtttgg ctctgtccct tctttctgtg tctgcaggcc attttcattc tgtagtttac   7020
ttgtcagttc caaggttgcc atggcagscc tygcagagaa gaggagggag ccattgaagg   7080
caaaggaagg ggatctgctc aaaggtctcc tgaacaatgg tggcttgtct gtggtatggg   7140
ggctgagaat cagaactgtg gactttttt gggagccttt gttgggtttg gaaggataga   7200
agcagagatg gaaacacagc agagagttgg ggggaaggga ccactgccac acaggggagg   7260
aggggctctg ggactgttgg tacatggaag gttctagtgc tgtggggaga ggccagcttc   7320
aacagtgata gttgagtggt tctcttttcc actggtggaa acacccactc tttctcctga   7380
tctgcctgcc tgtccttgct ctctctttt cctctgctct gtgctgtcct gatcatacat   7440
ctgtgcacat ggcatttcca tgcacatgca catgcagttc atcaggaatc ctctgttccc   7500
agtgaggcca gagtgcagct ggagaagcag acaattagct gtagtgcaat aggagaggtt   7560
ccagagtagg gatctgcaca aagtgctttg ggggcaaaga agggaacaca gttcactgct   7620
ggcgtgattg ggtggacctc actgaagagg tggcatttga atactgaagg acaaatagga   7680
ttttatcagc tagagaaata gaggaaggct acttcagggg catagggagc atcgtgtggc   7740
tagaaaatac atgaaagaga gtagatgaag agaaagtgag tagttcagca tggctggagc   7800
gtggggtagg tgtggggctg ggagatgagc ctagctggac aggtggatgg gagcatgttg   7860
tgaagggtct gtgtcatatc cagaagtgtt caggctataa cttatagata ttggggagtg   7920
gttggaggtt tttggccact aaagccagga ggttttagca agatcaccct ggtggtgtgg   7980
aagtagaggg tggatgggag gaattgttca aggtggggag actgctctcc tcctgccgct   8040
ccccgtcctg ctcacatttt cgcatcctcc ctgtgccacc atgagctccc tgcccgtgct   8100
ccctgcccac tctcccttag ggttctgccc atccttactg cagtcccggc tactactcta   8160
ccctgttctg cctgtgccct ctcttccttt ctaggcccgc ctctggctcc tgggcctggg   8220
ctttagtctg ggctacggtt ccatgttcac caagatttgg tgggtccaca cggtcttcac   8280
aaagaaggaa gaaaagaagg agtggaggaa ggtgagctgc tgcccaatcc tcagccccca   8340
aatccttggc tcctggggca cagagcattt tcccctgacg tgcctgttct ccccacatat   8400
ttatccagac tctggaaccc tggaagctgt atgccacagt gggcctgctg gtgggcatgg   8460
atgtcctcac tctcgccatc tggcagatcg tggaccctct gcaccggacc attgaggtac   8520
cactggagag gaggtgctat ggtcaggaga atgagcaggg ctcagtggcc atcagggccc   8580
tggggctgtg tgtgtcttga gggatgaagc tacttggaga gagtgccttc ctcgtattgg   8640
aagctcttcc tttccttcct agaaggagcc cctcataggc ctccagattc agctgaaraa   8700
aggaaggggt gggaatctgg gaagggtgtg tagaacttcc aggcatcagg gaaagtgggg   8760
```

-continued

```
aacaagcacc tccaagggtt caggaaaaca ttcttaggcc tagaatgaga tttggcatca   8820
gcattgaggg tctcatagga aaacagttgg aagccagaga ctgagaagcg ttgaggagag   8880
gaggggaggc tggcaaccat ctttcttgtg acctygtttc tgccctagac atttgccaag   8940
gaggaaccta aggaagatat tgacgtctct attctgcccc agctggagca ttgcagctcc   9000
aggaagatga atacatggct tggtgtgtgg gatgtgggca aaggagggca gggatgcaca   9060
aaggcaggag ggaaggcagg ggtagagggc ttggagggag argggtcttt ggaagaggag   9120
gtagagagct tgtcaaccca gtttgaacac cctactcttt gttatkgcac tawtcttttc   9180
tgagaatagg ggagagttgy tcttttgcta tgaggagctt agggcccaaa gcacagaaag   9240
cacagatgaa gaacttgtgt tcagcagagg aacaagtggg ggtaacccca cctccagact   9300
tgacattaty ttttagatcc cccttggcct tattagcatt gttcgattca tggtcacaaa   9360
ttgcaaacct accytctgcc tggaaagcca ccttcccacc tgtagggtaa gggtgaggca   9420
tgtgtggccc agactggcct atttctagat attcaacaag cccttgcctg actgacagca   9480
gcttgccacc attgctttcc tgtgtgaatc ccaggaaaaa gtgatgtggt ctgggcaagt   9540
tgggtggaca taagggatag gggacacagg gtgaggtttg ctaggtcaga ggggttggat   9600
tggagaggag ggccccccttt ccatttcaga gtaggtgaag ggcagagagg ggatggggat   9660
tgagtgagga gcattgtggt ccttgttgct caagtgactc tctcctgcca tcctaggcat   9720
tttctatggt tacaaggggc tgctgctgct gctgggaatc ttccttgctt atgagaccaa   9780
gagtgtgtcc actgagaaga tcaatgatca ccgggctgtg ggcatggcta tctacaatgt   9840
ggcagtgagc actgacccca tggcattgac cctgtaggct gaccacagca gcccagatat   9900
agaggactag gaagaatcaa tgctagatct gggatcggtt gcttagaagt cttaaaaagt   9960
ttgttaattc ttcaggtcta taaagcactt tacagtttac aaagctcact acagacattg  10020
tatcattaat cttgcaacta cccagtgaag tagatattag tatccccact ttataggtga  10080
ggaaacagaa acacagagac gttaaattgc ttgtctgtgg ttaatgggct ggactctatt  10140
gacatttcct gccagggacc gactctggag gacccggaat ctgtgcatag agatcctggg  10200
agttcctgcc ttgaggggag gggttaacca agagtgaaaa ctggtttggg acagtttgag  10260
atttttctcm atctatattt gargatgatc ctgaatttgg atccttttca aagggaaagt  10320
tcaccaggaa actgtctgca tagactccct cccatgggaa gtaaactctg gatcttgtct  10380
gagcctgcag acctgagact ccctcaatgt gtctttccct ctaggtcctg tgcctcatca  10440
ctgctcctgt caccatgatt ctgtccagcc agcaggatgc agcctttgcc tttgcctctc  10500
ttgccatagt tttctcctcc tatatcactc ttgttgtgct ctttgtgccc aaggtaagga  10560
tctggctttt ctcccaccct ctttgttccc atgttccctc catccctcct tcctatatta  10620
ctgagttcct ctgcccttcc gttcaccctc ctctcactcc tccccttgtt ttgggcccaa  10680
ctcttatcag cattccttcc acctccaacc ttccatcagc cagtcactag tacagtcctt  10740
gctgggccac cccacgccca aacatttgcc cccagatgcg caggctgatc acccgagggg  10800
aatggcagtc ggaggcgcag gacaccatga agacagggtc atcgaccaac aacaacgagg  10860
aggagaagtc ccggctgttg gagaaggaga accgtgaact ggaaaagatc attgctgagg  10920
tgcgggggtg ggtgtcaggg tagggtgttg gartggtcca rgnaggcttg cgtcttarct  10980
tngggttgtc tgaagcccaa gcctgagata cagggtcaga tgttcttggc tcatggaggg  11040
agggtcctag gagacaacct gtaaggagtg aatggagcag catagggag gggaaagggc  11100
tgagcaagat tctatctcag gcaaaatcca gtgttggcct ggcaggtgga agggctctgg  11160
```

```
agtgggagct atgtggttga ctcagcctcc ttaaggcaag aggatggctg ttggctgtag  11220
gtgacaactg gagagaggca gctgtgagcc tctagtagtc aacactcaca gcagctgggt  11280
gtagcatgca sccccagcat aaaaggacct gggcaggcgt tcactgtgcc ccaggctgtc  11340
attaggggct ggtgcaatgc caaagagagg gatgttccaa ctgggttgac acatctctct  11400
gatttattgg aagctctgtg cactgacttt tctctccttc cccacttttt ccttttgttt  11460
ttaaattctc tcttatttcc ctgatcgcat tttttctatc ggtatcctta tgttctctgg  11520
cttttcttgt tctgttttga tttctccttt taatttattc tgtccactta ccctacgtcc  11580
tccccctaca ttyttctgtg cccttcctct ctttccctgt gcccttcctc tctttccctc  11640
ctccccactc cttcatcacc tcctcttctc ctactatccc aattgtgctt cttcctccag  11700
aaagaggagc gtgtctctga actgcgccat caactccagt ctcggcagca gctccgctcc  11760
cggcgccacc caccgacacc cccagaaccc tctgggggcc tgcccagggg accccctgag  11820
ccccccgacc ggcttagctg tgatgggagt cgagtgcatt tgctttataa gtgagggtag  11880
ggtgagggag gacaggccag taggggggagg gaaagggaga ggggaagggc aggggactca  11940
ggaagcaggg ggtccccatc cccagctggg aagaacatgc tatccaatct catctcttgt  12000
aaatacatgt ccccctgtga gttctgggct gatttgggtc tctcatacct ctgggaaaca  12060
gaccttttc tctcttactg cttcatgtaa ttttgtatca cctcttcaca atttagttcg  12120
tacctggctt gaagctgctc actgctcaca cgctgcctcc tcagcagcct cactgcatct  12180
ttctcttccc atgcaacacc ctcttctagt taccacggca acccctgcag ctcctctgcc  12240
tttgtgctct gttcctgtcc agcaggggtc tcccaacaag tgctctttcc accccaaagg  12300
ggcctctcct tttctccact gtcataatct ctttccatct tacttgccct tctatacttt  12360
ctcacatgtg gctccccctg aattttgctt cctttgggag ctcattcttt tcgccaaggc  12420
tcacatgctc cttgcctctg ctctgtgcac tcacgctcag cacacatgca tcctcccctc  12480
tcctgcgtgt gcccactgaa catgctcatg tgtacacacg cttttcccgt atgctttctt  12540
catgttcagt cacatgtgct ctcgggtgcc ctgcattcac agctacgtgt gcccctctca  12600
tggtcatggg tctgcccttg agcgtgtttg ggtaggcatg tgcaatttgt ctagcatgct  12660
gagtcatgtc tttcctattt gcacacgtcc atgtttatcc atgtactttc cctgtgtacc  12720
ctccatgtac cttgtgtact ttcttccctt aaatcatggt attcttctga cagagccata  12780
tgtaccctac cctgcacatt gttatgcact tttccccaat tcatgtttgg tggggccatc  12840
cacaccctct ccttgtcaca gaatctccat ttctgctcag attcccccca tctccattgc  12900
attcatgtac taccctcagt ctacactcac aatcatcttc tcccaagact gctccctttt  12960
gttttgtgtt tttttgaggg gaattaagga aaaataagtg ggggcaggtt tggagagctg  13020
cttccagtgg atagttgatg agaatcctga ccaaaggaag gcacccttga ctgttgggat  13080
agacagatgg acctatgggg tgggaggtgg tgtccctttc acactgtggt gtctcttggg  13140
gaaggatctc cccgaatctc aataaaccag tgaacagtgt gactcgg               13187
```

<210> SEQ ID NO 62
<211> LENGTH: 50
<212> TYPE: DNA
<213> ORGANISM: Rattus norvegicus

<400> SEQUENCE: 62

```
atgcgcgccg gcagccaaca tgctgctgct gctgctggtg cctctcttcc              50
```

<210> SEQ ID NO 63
<211> LENGTH: 25
<212> TYPE: DNA
<213> ORGANISM: Rattus norvegicus

<400> SEQUENCE: 63
ggtcatccag cgttgaggtg aagac 25

<210> SEQ ID NO 64
<211> LENGTH: 25
<212> TYPE: DNA
<213> ORGANISM: Rattus norvegicus

<400> SEQUENCE: 64
gaaggttgcc agattataca tccgc 25

<210> SEQ ID NO 65
<211> LENGTH: 25
<212> TYPE: DNA
<213> ORGANISM: Rattus norvegicus

<400> SEQUENCE: 65
ccacgatgat tcgagcatct tgacg 25

<210> SEQ ID NO 66
<211> LENGTH: 18
<212> TYPE: DNA
<213> ORGANISM: Homo sapiens

<400> SEQUENCE: 66
ctggttcctc ccaatgtg 18

<210> SEQ ID NO 67
<211> LENGTH: 21
<212> TYPE: DNA
<213> ORGANISM: Homo sapiens

<400> SEQUENCE: 67
ccagtggact atgagattga g 21

<210> SEQ ID NO 68
<211> LENGTH: 18
<212> TYPE: DNA
<213> ORGANISM: Homo sapiens

<400> SEQUENCE: 68
ctggttcctc ccaatgtg 18

<210> SEQ ID NO 69
<211> LENGTH: 21
<212> TYPE: DNA
<213> ORGANISM: Homo sapiens

<400> SEQUENCE: 69
ccagtggact atgagattga g 21

<210> SEQ ID NO 70
<211> LENGTH: 2700
<212> TYPE: DNA
<213> ORGANISM: Homo sapiens
<220> FEATURE:
<221> NAME/KEY: CDS
<222> LOCATION: (1)...(2697)

```
<400> SEQUENCE: 70

atg ttg ctg ctg ctg cta ctg gcg cca ctc ttc ctc cgc ccc ccg ggc       48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc       96
Ala Gly Gly Ala Gln Thr Pro Asn Ala Thr Ser Glu Gly Cys Gln Ile
            20                  25                  30

ata cac ccg ccc tgg gaa ggg ggc atc agg tac cgg ggc ctg act cgg      144
Ile His Pro Pro Trp Glu Gly Gly Ile Arg Tyr Arg Gly Leu Thr Arg
        35                  40                  45

gac cag gtg aag gct atc aac ttc ctg cca gtg gac tat gag att gag      192
Asp Gln Val Lys Ala Ile Asn Phe Leu Pro Val Asp Tyr Glu Ile Glu
    50                  55                  60

tat gtg tgc cgg ggg gag cgc gag gtg gtg ggg ccc aag gtc cgc aag      240
Tyr Val Cys Arg Gly Glu Arg Glu Val Val Gly Pro Lys Val Arg Lys
 65                  70                  75                  80

tgc ctg gcc aac ggc tcc tgg aca gat atg gac aca ccc agc cgc tgt      288
Cys Leu Ala Asn Gly Ser Trp Thr Asp Met Asp Thr Pro Ser Arg Cys
                 85                  90                  95

gtg aat cga acg cca cac tca gaa cgg cgc gca gtg tac atc ggg gca      336
Val Asn Arg Thr Pro His Ser Glu Arg Arg Ala Val Tyr Ile Gly Ala
            100                 105                 110

ctg ttt ccc atg agc ggg ggc tgg cca ggg ggc cag gcc tgc cag ccc      384
Leu Phe Pro Met Ser Gly Gly Trp Pro Gly Gly Gln Ala Cys Gln Pro
        115                 120                 125

gcg gtg gag atg gcg ctg gag gac gtg aat agc cgc agg gac atc ctg      432
Ala Val Glu Met Ala Leu Glu Asp Val Asn Ser Arg Arg Asp Ile Leu
    130                 135                 140

ccg gac tat gag ctc aag ctc atc cac cac gac agc aag tgt gat cca      480
Pro Asp Tyr Glu Leu Lys Leu Ile His His Asp Ser Lys Cys Asp Pro
145                 150                 155                 160

ggc caa gcc acc aag tac cta tat gag ctg ctc tac aac gac cct atc      528
Gly Gln Ala Thr Lys Tyr Leu Tyr Glu Leu Leu Tyr Asn Asp Pro Ile
                165                 170                 175

aag atc atc ctt atg cct ggc tgc agc tct gtc tcc acg ctg gtg gct      576
Lys Ile Ile Leu Met Pro Gly Cys Ser Ser Val Ser Thr Leu Val Ala
            180                 185                 190

gag gct gct agg atg tgg aac ctc att gtg ctt tcc tat ggc tcc agc      624
Glu Ala Ala Arg Met Trp Asn Leu Ile Val Leu Ser Tyr Gly Ser Ser
        195                 200                 205

tca cca gcc ctg tca aac cgg cag cgt ttc ccc act ttc ttc cga acg      672
Ser Pro Ala Leu Ser Asn Arg Gln Arg Phe Pro Thr Phe Phe Arg Thr
    210                 215                 220

cac cca tca gcc aca ctc cac aac cct acc cgc gtg aaa ctc ttt gaa      720
His Pro Ser Ala Thr Leu His Asn Pro Thr Arg Val Lys Leu Phe Glu
225                 230                 235                 240

aag tgg ggc tgg aag aag att gct acc atc cag cag acc act gag gtc      768
Lys Trp Gly Trp Lys Lys Ile Ala Thr Ile Gln Gln Thr Thr Glu Val
                245                 250                 255

ttc act tcg act ctg gac gac ctg gag gaa cga gtg aag gag gct gga      816
Phe Thr Ser Thr Leu Asp Asp Leu Glu Glu Arg Val Lys Glu Ala Gly
            260                 265                 270

att gag att act ttc cgc cag agt ttc ttc tca gat cca gct gtg ccc      864
Ile Glu Ile Thr Phe Arg Gln Ser Phe Phe Ser Asp Pro Ala Val Pro
        275                 280                 285

gtc aaa aac ctg aag cgc cag gat gcc cga atc atc gtg gga ctt ttc      912
Val Lys Asn Leu Lys Arg Gln Asp Ala Arg Ile Ile Val Gly Leu Phe
    290                 295                 300

tat gag act gaa gcc cgg aaa gtt ttt tgt gag gtg tac aag gag cgt      960
```

-continued

```
Tyr Glu Thr Glu Ala Arg Lys Val Phe Cys Glu Val Tyr Lys Glu Arg
305                 310                 315                 320

ctc ttt ggg aag aag tac gtc tgg ttc ctc att ggg tgg tat gct gac      1008
Leu Phe Gly Lys Lys Tyr Val Trp Phe Leu Ile Gly Trp Tyr Ala Asp
                325                 330                 335

aat tgg ttc aag atc tac gac cct tct atc aac tgc aca gtg gat gag      1056
Asn Trp Phe Lys Ile Tyr Asp Pro Ser Ile Asn Cys Thr Val Asp Glu
            340                 345                 350

atg act gag gcg gtg gag ggc cac atc aca act gag att gtc atg ctg      1104
Met Thr Glu Ala Val Glu Gly His Ile Thr Thr Glu Ile Val Met Leu
        355                 360                 365

aat cct gcc aat acc cgc agc att tcc aac atg aca tcc cag gaa ttt      1152
Asn Pro Ala Asn Thr Arg Ser Ile Ser Asn Met Thr Ser Gln Glu Phe
    370                 375                 380

gtg gag aaa cta acc aag cga ctg aaa aga cac cct gag gag aca gga      1200
Val Glu Lys Leu Thr Lys Arg Leu Lys Arg His Pro Glu Glu Thr Gly
385                 390                 395                 400

ggc ttc cag gag gca ccg ctg gcc tat gat gcc atc tgg gcc ttg gca      1248
Gly Phe Gln Glu Ala Pro Leu Ala Tyr Asp Ala Ile Trp Ala Leu Ala
                405                 410                 415

ctg gcc ctg aac aag aca tct gga gga ggc ggc cgt tct ggt gtg cgc      1296
Leu Ala Leu Asn Lys Thr Ser Gly Gly Gly Gly Arg Ser Gly Val Arg
            420                 425                 430

ctg gag gac ttc aac tac aac aac cag acc att acc gac caa atc tac      1344
Leu Glu Asp Phe Asn Tyr Asn Asn Gln Thr Ile Thr Asp Gln Ile Tyr
        435                 440                 445

cgg gca atg aac tct tcg tcc ttt gag ggt gtc tct ggc cat gtg gtg      1392
Arg Ala Met Asn Ser Ser Ser Phe Glu Gly Val Ser Gly His Val Val
    450                 455                 460

ttt gat gcc agc ggc tct cgg atg gca tgg acg ctt atc gag cag ctt      1440
Phe Asp Ala Ser Gly Ser Arg Met Ala Trp Thr Leu Ile Glu Gln Leu
465                 470                 475                 480

cag ggt ggc agc tac aag aag att ggc tac tat gac agc acc aag gat      1488
Gln Gly Gly Ser Tyr Lys Lys Ile Gly Tyr Tyr Asp Ser Thr Lys Asp
                485                 490                 495

gat ctt tcc tgg tcc aaa aca gat aaa tgg att gga ggg tcc ccc cca      1536
Asp Leu Ser Trp Ser Lys Thr Asp Lys Trp Ile Gly Gly Ser Pro Pro
            500                 505                 510

gct gac cag acc ctg gtc atc aag aca ttc cgc ttc ctg tca cag aaa      1584
Ala Asp Gln Thr Leu Val Ile Lys Thr Phe Arg Phe Leu Ser Gln Lys
        515                 520                 525

ctc ttt atc tcc gtc tca gtt ctc tcc agc ctg ggc att gtc cta gct      1632
Leu Phe Ile Ser Val Ser Val Leu Ser Ser Leu Gly Ile Val Leu Ala
    530                 535                 540

gtt gtc tgt ctg tcc ttt aac atc tac aac tca cat gtc cgt tat atc      1680
Val Val Cys Leu Ser Phe Asn Ile Tyr Asn Ser His Val Arg Tyr Ile
545                 550                 555                 560

cag aac tca cag ccc aac ctg aac aac ctg act gct gtg ggc tgc tca      1728
Gln Asn Ser Gln Pro Asn Leu Asn Asn Leu Thr Ala Val Gly Cys Ser
                565                 570                 575

ctg gct tta gct gct gtc ttc ccc ctg ggg ctc gat ggt tac cac att      1776
Leu Ala Leu Ala Ala Val Phe Pro Leu Gly Leu Asp Gly Tyr His Ile
            580                 585                 590

ggg agg aac cag ttt cct ttc gtc tgc cag gcc cgc ctc tgg ctc ctg      1824
Gly Arg Asn Gln Phe Pro Phe Val Cys Gln Ala Arg Leu Trp Leu Leu
        595                 600                 605

ggc ctg ggc ttt agt ctg ggc tac ggt tcc atg ttc acc aag att tgg      1872
Gly Leu Gly Phe Ser Leu Gly Tyr Gly Ser Met Phe Thr Lys Ile Trp
    610                 615                 620
```

-continued

```
tgg gtc cac acg gtc ttc aca aag aag gaa gaa aag aag gag tgg agg      1920
Trp Val His Thr Val Phe Thr Lys Lys Glu Glu Lys Lys Glu Trp Arg
625                 630                 635                 640

aag act ctg gaa ccc tgg aag ctg tat gcc aca gtg ggc ctg ctg gtg      1968
Lys Thr Leu Glu Pro Trp Lys Leu Tyr Ala Thr Val Gly Leu Leu Val
                645                 650                 655

ggc atg gat gtc ctc act ctc gcc atc tgg cag atc gtg gac cct ctg      2016
Gly Met Asp Val Leu Thr Leu Ala Ile Trp Gln Ile Val Asp Pro Leu
            660                 665                 670

cac cgg acc att gag aca ttt gcc aag gag gaa cct aag gaa gat att      2064
His Arg Thr Ile Glu Thr Phe Ala Lys Glu Glu Pro Lys Glu Asp Ile
        675                 680                 685

gac gtc tct att ctg ccc cag ctg gag cat tgc agc tcc agg aag atg      2112
Asp Val Ser Ile Leu Pro Gln Leu Glu His Cys Ser Ser Arg Lys Met
    690                 695                 700

aat aca tgg ctt ggc att ttc tat ggt tac aag ggg ctg ctg ctg ctg      2160
Asn Thr Trp Leu Gly Ile Phe Tyr Gly Tyr Lys Gly Leu Leu Leu Leu
705                 710                 715                 720

ctg gga atc ttc ctt gct tat gag acc aag agt gtg tcc act gag aag      2208
Leu Gly Ile Phe Leu Ala Tyr Glu Thr Lys Ser Val Ser Thr Glu Lys
                725                 730                 735

atc aat gat cac cgg gct gtg ggc atg gct atc tac aat gtg gca gtc      2256
Ile Asn Asp His Arg Ala Val Gly Met Ala Ile Tyr Asn Val Ala Val
            740                 745                 750

ctg tgc ctc atc act gct cct gtc acc atg att ctg tcc agc cag cag      2304
Leu Cys Leu Ile Thr Ala Pro Val Thr Met Ile Leu Ser Ser Gln Gln
        755                 760                 765

gat gca gcc ttt gcc ttt gcc tct ctt gcc ata gtt ttc tcc tcc tat      2352
Asp Ala Ala Phe Ala Phe Ala Ser Leu Ala Ile Val Phe Ser Ser Tyr
    770                 775                 780

atc act ctt gtt gtg ctc ttt gtg ccc aag atg cgc agg ctg atc acc      2400
Ile Thr Leu Val Val Leu Phe Val Pro Lys Met Arg Arg Leu Ile Thr
785                 790                 795                 800

cga ggg gaa tgg cag tcg gag gcg cag gac acc atg aag aca ggg tca      2448
Arg Gly Glu Trp Gln Ser Glu Ala Gln Asp Thr Met Lys Thr Gly Ser
                805                 810                 815

tcg acc aac aac aac gag gag gag aag tcc cgg ctg ttg gag aag gag      2496
Ser Thr Asn Asn Asn Glu Glu Glu Lys Ser Arg Leu Leu Glu Lys Glu
            820                 825                 830

aac cgt gaa ctg gaa aag atc att gct gag aaa gag gag cgt gtc tct      2544
Asn Arg Glu Leu Glu Lys Ile Ile Ala Glu Lys Glu Glu Arg Val Ser
        835                 840                 845

gaa ctg cgc cat caa ctc cag tct cgg cag cag ctc cgc tcc cgg cgc      2592
Glu Leu Arg His Gln Leu Gln Ser Arg Gln Gln Leu Arg Ser Arg Arg
    850                 855                 860

cac cca ccg aca ccc cca gaa ccc tct ggg ggc ctg ccc agg gga ccc      2640
His Pro Pro Thr Pro Pro Glu Pro Ser Gly Gly Leu Pro Arg Gly Pro
865                 870                 875                 880

cct gag ccc ccc gac cgg ctt agc tgt gat ggg agt cga gtg cat ttg      2688
Pro Glu Pro Pro Asp Arg Leu Ser Cys Asp Gly Ser Arg Val His Leu
                885                 890                 895

ctt tat aag tga                                                      2700
Leu Tyr Lys
```

<210> SEQ ID NO 71
<211> LENGTH: 899
<212> TYPE: PRT
<213> ORGANISM: Homo sapiens

<400> SEQUENCE: 71

-continued

```
Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Asn Arg Thr Pro His Ser Glu Arg Arg Ala Val Tyr Ile Gly Ala
            100                 105                 110

Leu Phe Pro Met Ser Gly Gly Trp Pro Gly Gly Gln Ala Cys Gln Pro
        115                 120                 125

Ala Val Glu Met Ala Leu Glu Asp Val Asn Ser Arg Arg Asp Ile Leu
    130                 135                 140

Pro Asp Tyr Glu Leu Lys Leu Ile His His Asp Ser Lys Cys Asp Pro
145                 150                 155                 160

Gly Gln Ala Thr Lys Tyr Leu Tyr Glu Leu Leu Tyr Asn Asp Pro Ile
                165                 170                 175

Lys Ile Ile Leu Met Pro Gly Cys Ser Ser Val Ser Thr Leu Val Ala
            180                 185                 190

Glu Ala Ala Arg Met Trp Asn Leu Ile Val Leu Ser Tyr Gly Ser Ser
        195                 200                 205

Ser Pro Ala Leu Ser Asn Arg Gln Arg Phe Pro Thr Phe Phe Arg Thr
    210                 215                 220

His Pro Ser Ala Thr Leu His Asn Pro Thr Arg Val Lys Leu Phe Glu
225                 230                 235                 240

Lys Trp Gly Trp Lys Lys Ile Ala Thr Ile Gln Gln Thr Thr Glu Val
                245                 250                 255

Phe Thr Ser Thr Leu Asp Asp Leu Glu Glu Arg Val Lys Glu Ala Gly
            260                 265                 270

Ile Glu Ile Thr Phe Arg Gln Ser Phe Phe Ser Asp Pro Ala Val Pro
        275                 280                 285

Val Lys Asn Leu Lys Arg Gln Asp Ala Arg Ile Ile Val Gly Leu Phe
    290                 295                 300

Tyr Glu Thr Glu Ala Arg Lys Val Phe Cys Glu Val Tyr Lys Glu Arg
305                 310                 315                 320

Leu Phe Gly Lys Lys Tyr Val Trp Phe Leu Ile Gly Trp Tyr Ala Asp
                325                 330                 335

Asn Trp Phe Lys Ile Tyr Asp Pro Ser Ile Asn Cys Thr Val Asp Glu
            340                 345                 350

Met Thr Glu Ala Val Glu Gly His Ile Thr Thr Glu Ile Val Met Leu
        355                 360                 365

Asn Pro Ala Asn Thr Arg Ser Ile Ser Asn Met Thr Ser Gln Glu Phe
    370                 375                 380

Val Glu Lys Leu Thr Lys Arg Leu Lys Arg His Pro Glu Glu Thr Gly
385                 390                 395                 400

Gly Phe Gln Glu Ala Pro Leu Ala Tyr Asp Ala Ile Trp Ala Leu Ala
                405                 410                 415

Leu Ala Leu Asn Lys Thr Ser Gly Gly Gly Gly Arg Ser Gly Val Arg
```

-continued

```
            420                 425                 430

Leu Glu Asp Phe Asn Tyr Asn Asn Gln Thr Ile Thr Asp Gln Ile Tyr
        435                 440                 445

Arg Ala Met Asn Ser Ser Ser Phe Glu Gly Val Ser Gly His Val Val
    450                 455                 460

Phe Asp Ala Ser Gly Ser Arg Met Ala Trp Thr Leu Ile Glu Gln Leu
465                 470                 475                 480

Gln Gly Gly Ser Tyr Lys Lys Ile Gly Tyr Tyr Asp Ser Thr Lys Asp
                485                 490                 495

Asp Leu Ser Trp Ser Lys Thr Asp Lys Trp Ile Gly Gly Ser Pro Pro
            500                 505                 510

Ala Asp Gln Thr Leu Val Ile Lys Thr Phe Arg Phe Leu Ser Gln Lys
        515                 520                 525

Leu Phe Ile Ser Val Ser Val Leu Ser Ser Leu Gly Ile Val Leu Ala
    530                 535                 540

Val Val Cys Leu Ser Phe Asn Ile Tyr Asn Ser His Val Arg Tyr Ile
545                 550                 555                 560

Gln Asn Ser Gln Pro Asn Leu Asn Asn Leu Thr Ala Val Gly Cys Ser
                565                 570                 575

Leu Ala Leu Ala Ala Val Phe Pro Leu Gly Leu Asp Gly Tyr His Ile
            580                 585                 590

Gly Arg Asn Gln Phe Pro Phe Val Cys Gln Ala Arg Leu Trp Leu Leu
        595                 600                 605

Gly Leu Gly Phe Ser Leu Gly Tyr Gly Ser Met Phe Thr Lys Ile Trp
    610                 615                 620

Trp Val His Thr Val Phe Thr Lys Lys Glu Glu Lys Lys Glu Trp Arg
625                 630                 635                 640

Lys Thr Leu Glu Pro Trp Lys Leu Tyr Ala Thr Val Gly Leu Leu Val
                645                 650                 655

Gly Met Asp Val Leu Thr Leu Ala Ile Trp Gln Ile Val Asp Pro Leu
            660                 665                 670

His Arg Thr Ile Glu Thr Phe Ala Lys Glu Glu Pro Lys Glu Asp Ile
        675                 680                 685

Asp Val Ser Ile Leu Pro Gln Leu Glu His Cys Ser Ser Arg Lys Met
    690                 695                 700

Asn Thr Trp Leu Gly Ile Phe Tyr Gly Tyr Lys Gly Leu Leu Leu Leu
705                 710                 715                 720

Leu Gly Ile Phe Leu Ala Tyr Glu Thr Lys Ser Val Ser Thr Glu Lys
                725                 730                 735

Ile Asn Asp His Arg Ala Val Gly Met Ala Ile Tyr Asn Val Ala Val
            740                 745                 750

Leu Cys Leu Ile Thr Ala Pro Val Thr Met Ile Leu Ser Ser Gln Gln
        755                 760                 765

Asp Ala Ala Phe Ala Phe Ala Ser Leu Ala Ile Val Phe Ser Ser Tyr
    770                 775                 780

Ile Thr Leu Val Val Leu Phe Val Pro Lys Met Arg Arg Leu Ile Thr
785                 790                 795                 800

Arg Gly Glu Trp Gln Ser Glu Ala Gln Asp Thr Met Lys Thr Gly Ser
                805                 810                 815

Ser Thr Asn Asn Asn Glu Glu Glu Lys Ser Arg Leu Leu Glu Lys Glu
            820                 825                 830

Asn Arg Glu Leu Glu Lys Ile Ile Ala Glu Lys Glu Glu Arg Val Ser
        835                 840                 845
```

```
Glu Leu Arg His Gln Leu Gln Ser Arg Gln Gln Leu Arg Ser Arg Arg
    850                 855                 860

His Pro Pro Thr Pro Pro Glu Pro Ser Gly Gly Leu Pro Arg Gly Pro
865                 870                 875                 880

Pro Glu Pro Pro Asp Arg Leu Ser Cys Asp Gly Ser Arg Val His Leu
                885                 890                 895

Leu Tyr Lys


<210> SEQ ID NO 72
<211> LENGTH: 2518
<212> TYPE: DNA
<213> ORGANISM: Homo sapiens
<220> FEATURE:
<221> NAME/KEY: CDS
<222> LOCATION: (1)...(291)

<400> SEQUENCE: 72

atg ttg ctg ctg ctg cta ctg gcg cca ctc ttc ctc cgc ccc ccg ggc       48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc       96
Ala Gly Gly Ala Gln Thr Pro Asn Ala Thr Ser Glu Gly Cys Gln Ile
             20                  25                  30

ata cac ccg ccc tgg gaa ggg ggc atc agg tac cgg ggc ctg act cgg      144
Ile His Pro Pro Trp Glu Gly Gly Ile Arg Tyr Arg Gly Leu Thr Arg
         35                  40                  45

gac cag gtg aag gct atc aac ttc ctg cca gtg gac tat gag att gag      192
Asp Gln Val Lys Ala Ile Asn Phe Leu Pro Val Asp Tyr Glu Ile Glu
     50                  55                  60

tat gtg tgc cgg ggg gag cgc gag gtg gtg ggg ccc aag gtc cgc aag      240
Tyr Val Cys Arg Gly Glu Arg Glu Val Val Gly Pro Lys Val Arg Lys
 65                  70                  75                  80

tgc ctg gcc aac ggc tcc tgg aca gat atg gac aca ccc agc cgc tgt      288
Cys Leu Ala Asn Gly Ser Trp Thr Asp Met Asp Thr Pro Ser Arg Cys
                 85                  90                  95

gtg tgatccaggc caagccacca agtacctata tgagctgctc tacaacgacc           341
Val

ctatcaagat catccttatg cctggctgca gctctgtctc cacgctggtg gctgaggctg    401

ctaggatgtg gaacctcatt gtgctttcct atggctccag ctcaccagcc ctgtcaaacc    461

ggcagcgttt ccccactttc ttccgaacgc acccatcagc cacactccac aaccctaccc    521

gcgtgaaact ctttgaaaag tggggctgga agaagattgc taccatccag cagaccactg    581

aggtcttcac ttcgactctg gacgacctgg aggaacgagt gaaggaggct ggaattgaga    641

ttactttccg ccagagtttc ttctcagatc cagctgtgcc cgtcaaaaac ctgaagcgcc    701

aggatgcccg aatcatcgtg ggacttttct atgagactga agcccggaaa gtttttttgtg   761

aggtgtacaa ggagcgtctc tttgggaaga agtacgtctg gttcctcatt gggtggtatg    821

ctgacaattg gttcaagatc tacgaccctt ctatcaactg cacagtggat gagatgactg    881

aggcggtgga gggccacatc acaactgaga ttgtcatgct gaatcctgcc aatacccgca    941

gcatttccaa catgacatcc caggaatttg tggagaaact aaccaagcga ctgaaaagac   1001

accctgagga gacaggaggc ttccaggagg caccgctggc ctatgatgcc atctgggcct   1061

tggcactggc cctgaacaag acatctggag gaggcggccg ttctggtgtg cgcctggagg   1121

acttcaacta caacaaccag accattaccg accaaatcta ccgggcaatg aactcttcgt   1181

cctttgaggg tgtctctggc catgtggtgt ttgatgccag cggctctcgg atggcatgga   1241
```

```
cgcttatcga gcagcttcag ggtggcagct acaagaagat tggctactat gacagcacca   1301

aggatgatct ttcctggtcc aaaacagata aatggattgg agggtccccc ccagctgacc   1361

agaccctggt catcaagaca ttccgcttcc tgtcacagaa actctttatc tccgtctcag   1421

ttctctccag cctgggcatt gtcctagctg ttgtctgtct gtcctttaac atctacaact   1481

cacatgtccg ttatatccag aactcacagc ccaacctgaa caacctgact gctgtgggct   1541

gctcactggc tttagctgct gtcttccccc tggggctcga tggttaccac attgggagga   1601

accagtttcc tttcgtctgc caggcccgcc tctggctcct gggcctgggc tttagtctgg   1661

gctacggttc catgttcacc aagatttggt gggtccacac ggtcttcaca aagaaggaag   1721

aaaagaagga gtggaggaag actctggaac cctggaagct gtatgccaca gtgggcctgc   1781

tggtgggcat ggatgtcctc actctcgcca tctggcagat cgtggaccct ctgcaccgga   1841

ccattgagac atttgccaag gaggaaccta aggaagatat tgacgtctct attctgcccc   1901

agctggagca ttgcagctcc aggaagatga atacatggct tggcattttc tatggttaca   1961

aggggctgct gctgctgctg ggaatcttcc ttgcttatga gaccaagagt gtgtccactg   2021

agaagatcaa tgatcaccgg gctgtgggca tggctatcta caatgtggca gtcctgtgcc   2081

tcatcactgc tcctgtcacc atgattctgt ccagccagca ggatgcagcc tttgcctttg   2141

cctctcttgc catagttttc tcctcctata tcactcttgt tgtgctcttt gtgcccaaga   2201

tgcgcaggct gatcacccga ggggaatggc agtcggaggc gcaggacacc atgaagacag   2261

ggtcatcgac caacaacaac gaggaggaga agtcccggct gttggagaag gagaaccgtg   2321

aactggaaaa gatcattgct gagaaagagg agcgtgtctc tgaactgcgc catcaactcc   2381

agtctcggca gcagctccgc tcccggcgcc acccaccgac acccccagaa ccctctgggg   2441

gcctgcccag gggacccccct gagcccccccg accggcttag ctgtgatggg agtcgagtgc   2501

atttgcttta taagtga                                                   2518
```

<210> SEQ ID NO 73
<211> LENGTH: 97
<212> TYPE: PRT
<213> ORGANISM: Homo sapiens

<400> SEQUENCE: 73

```
Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val
```

<210> SEQ ID NO 74
<211> LENGTH: 2679
<212> TYPE: DNA
<213> ORGANISM: Homo sapiens
<220> FEATURE:

-continued

```
<221> NAME/KEY: CDS
<222> LOCATION: (1)...(2676)

<400> SEQUENCE: 74

atg ttg ctg ctg ctg cta ctg gcg cca ctc ttc ctc cgc ccc ccg ggc      48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc      96
Ala Gly Gly Ala Gln Thr Pro Asn Ala Thr Ser Glu Gly Cys Gln Ile
            20                  25                  30

ata cac ccg ccc tgg gaa ggg ggc atc agg tac cgg ggc ctg act cgg     144
Ile His Pro Pro Trp Glu Gly Gly Ile Arg Tyr Arg Gly Leu Thr Arg
        35                  40                  45

gac cag gtg aag gct atc aac ttc ctg cca gtg gac tat gag att gag     192
Asp Gln Val Lys Ala Ile Asn Phe Leu Pro Val Asp Tyr Glu Ile Glu
    50                  55                  60

tat gtg tgc cgg ggg gag cgc gag gtg gtg ggg ccc aag gtc cgc aag     240
Tyr Val Cys Arg Gly Glu Arg Glu Val Val Gly Pro Lys Val Arg Lys
 65                  70                  75                  80

tgc ctg gcc aac ggc tcc tgg aca gat atg gac aca ccc agc cgc tgt     288
Cys Leu Ala Asn Gly Ser Trp Thr Asp Met Asp Thr Pro Ser Arg Cys
                85                  90                  95

gaa cgg cgc gca gtg tac atc ggg gca ctg ttt ccc atg agc ggg ggc     336
Glu Arg Arg Ala Val Tyr Ile Gly Ala Leu Phe Pro Met Ser Gly Gly
            100                 105                 110

tgg cca ggg ggc cag gcc tgc cag ccc gcg gtg gag atg gcg ctg gag     384
Trp Pro Gly Gly Gln Ala Cys Gln Pro Ala Val Glu Met Ala Leu Glu
        115                 120                 125

gac gtg aat agc cgc agg gac atc ctg ccg gac tat gag ctc aag ctc     432
Asp Val Asn Ser Arg Arg Asp Ile Leu Pro Asp Tyr Glu Leu Lys Leu
    130                 135                 140

atc cac cac gac agc aag tgt gat cca ggc caa gcc acc aag tac cta     480
Ile His His Asp Ser Lys Cys Asp Pro Gly Gln Ala Thr Lys Tyr Leu
145                 150                 155                 160

tat gag ctg ctc tac aac gac cct atc aag atc atc ctt atg cct ggc     528
Tyr Glu Leu Leu Tyr Asn Asp Pro Ile Lys Ile Ile Leu Met Pro Gly
                165                 170                 175

tgc agc tct gtc tcc acg ctg gtg gct gag gct gct agg atg tgg aac     576
Cys Ser Ser Val Ser Thr Leu Val Ala Glu Ala Ala Arg Met Trp Asn
            180                 185                 190

ctc att gtg ctt tcc tat ggc tcc agc tca cca gcc ctg tca aac cgg     624
Leu Ile Val Leu Ser Tyr Gly Ser Ser Ser Pro Ala Leu Ser Asn Arg
        195                 200                 205

cag cgt ttc ccc act ttc ttc cga acg cac cca tca gcc aca ctc cac     672
Gln Arg Phe Pro Thr Phe Phe Arg Thr His Pro Ser Ala Thr Leu His
    210                 215                 220

aac cct acc cgc gtg aaa ctc ttt gaa aag tgg ggc tgg aag aag att     720
Asn Pro Thr Arg Val Lys Leu Phe Glu Lys Trp Gly Trp Lys Lys Ile
225                 230                 235                 240

gct acc atc cag cag acc act gag gtc ttc act tcg act ctg gac gac     768
Ala Thr Ile Gln Gln Thr Thr Glu Val Phe Thr Ser Thr Leu Asp Asp
                245                 250                 255

ctg gag gaa cga gtg aag gag gct gga att gag att act ttc cgc cag     816
Leu Glu Glu Arg Val Lys Glu Ala Gly Ile Glu Ile Thr Phe Arg Gln
            260                 265                 270

agt ttc ttc tca gat cca gct gtg ccc gtc aaa aac ctg aag cgc cag     864
Ser Phe Phe Ser Asp Pro Ala Val Pro Val Lys Asn Leu Lys Arg Gln
        275                 280                 285

gat gcc cga atc atc gtg gga ctt ttc tat gag act gaa gcc cgg aaa     912
Asp Ala Arg Ile Ile Val Gly Leu Phe Tyr Glu Thr Glu Ala Arg Lys
```

-continued

```
    290                 295                 300

gtt ttt tgt gag gtg tac aag gag cgt ctc ttt ggg aag aag tac gtc      960
Val Phe Cys Glu Val Tyr Lys Glu Arg Leu Phe Gly Lys Lys Tyr Val
305                 310                 315                 320

tgg ttc ctc att ggg tgg tat gct gac aat tgg ttc aag atc tac gac     1008
Trp Phe Leu Ile Gly Trp Tyr Ala Asp Asn Trp Phe Lys Ile Tyr Asp
                325                 330                 335

cct tct atc aac tgc aca gtg gat gag atg act gag gcg gtg gag ggc     1056
Pro Ser Ile Asn Cys Thr Val Asp Glu Met Thr Glu Ala Val Glu Gly
            340                 345                 350

cac atc aca act gag att gtc atg ctg aat cct gcc aat acc cgc agc     1104
His Ile Thr Thr Glu Ile Val Met Leu Asn Pro Ala Asn Thr Arg Ser
        355                 360                 365

att tcc aac atg aca tcc cag gaa ttt gtg gag aaa cta acc aag cga     1152
Ile Ser Asn Met Thr Ser Gln Glu Phe Val Glu Lys Leu Thr Lys Arg
    370                 375                 380

ctg aaa aga cac cct gag gag aca gga ggc ttc cag gag gca ccg ctg     1200
Leu Lys Arg His Pro Glu Glu Thr Gly Gly Phe Gln Glu Ala Pro Leu
385                 390                 395                 400

gcc tat gat gcc atc tgg gcc ttg gca ctg gcc ctg aac aag aca tct     1248
Ala Tyr Asp Ala Ile Trp Ala Leu Ala Leu Ala Leu Asn Lys Thr Ser
                405                 410                 415

gga gga ggc ggc cgt tct ggt gtg cgc ctg gag gac ttc aac tac aac     1296
Gly Gly Gly Gly Arg Ser Gly Val Arg Leu Glu Asp Phe Asn Tyr Asn
            420                 425                 430

aac cag acc att acc gac caa atc tac cgg gca atg aac tct tcg tcc     1344
Asn Gln Thr Ile Thr Asp Gln Ile Tyr Arg Ala Met Asn Ser Ser Ser
        435                 440                 445

ttt gag ggt gtc tct ggc cat gtg gtg ttt gat gcc agc ggc tct cgg     1392
Phe Glu Gly Val Ser Gly His Val Val Phe Asp Ala Ser Gly Ser Arg
    450                 455                 460

atg gca tgg acg ctt atc gag cag ctt cag ggt ggc agc tac aag aag     1440
Met Ala Trp Thr Leu Ile Glu Gln Leu Gln Gly Gly Ser Tyr Lys Lys
465                 470                 475                 480

att ggc tac tat gac agc acc aag gat gat ctt tcc tgg tcc aaa aca     1488
Ile Gly Tyr Tyr Asp Ser Thr Lys Asp Asp Leu Ser Trp Ser Lys Thr
                485                 490                 495

gat aaa tgg att gga ggg tcc ccc cca gct gac cag acc ctg gtc atc     1536
Asp Lys Trp Ile Gly Gly Ser Pro Pro Ala Asp Gln Thr Leu Val Ile
            500                 505                 510

aag aca ttc cgc ttc ctg tca cag aaa ctc ttt atc tcc gtc tca gtt     1584
Lys Thr Phe Arg Phe Leu Ser Gln Lys Leu Phe Ile Ser Val Ser Val
        515                 520                 525

ctc tcc agc ctg ggc att gtc cta gct gtt gtc tgt ctg tcc ttt aac     1632
Leu Ser Ser Leu Gly Ile Val Leu Ala Val Val Cys Leu Ser Phe Asn
    530                 535                 540

atc tac aac tca cat gtc cgt tat atc cag aac tca cag ccc aac ctg     1680
Ile Tyr Asn Ser His Val Arg Tyr Ile Gln Asn Ser Gln Pro Asn Leu
545                 550                 555                 560

aac aac ctg act gct gtg ggc tgc tca ctg gct tta gct gct gtc ttc     1728
Asn Asn Leu Thr Ala Val Gly Cys Ser Leu Ala Leu Ala Ala Val Phe
                565                 570                 575

ccc ctg ggg ctc gat ggt tac cac att ggg agg aac cag ttt cct ttc     1776
Pro Leu Gly Leu Asp Gly Tyr His Ile Gly Arg Asn Gln Phe Pro Phe
            580                 585                 590

gtc tgc cag gcc cgc ctc tgg ctc ctg ggc ctg ggc ttt agt ctg ggc     1824
Val Cys Gln Ala Arg Leu Trp Leu Leu Gly Leu Gly Phe Ser Leu Gly
        595                 600                 605

tac ggt tcc atg ttc acc aag att tgg tgg gtc cac acg gtc ttc aca     1872
```

-continued

```
Tyr Gly Ser Met Phe Thr Lys Ile Trp Trp Val His Thr Val Phe Thr
    610                 615                 620

aag aag gaa gaa aag aag gag tgg agg aag act ctg gaa ccc tgg aag     1920
Lys Lys Glu Glu Lys Lys Glu Trp Arg Lys Thr Leu Glu Pro Trp Lys
625                 630                 635                 640

ctg tat gcc aca gtg ggc ctg ctg gtg ggc atg gat gtc ctc act ctc     1968
Leu Tyr Ala Thr Val Gly Leu Leu Val Gly Met Asp Val Leu Thr Leu
                645                 650                 655

gcc atc tgg cag atc gtg gac cct ctg cac cgg acc att gag aca ttt     2016
Ala Ile Trp Gln Ile Val Asp Pro Leu His Arg Thr Ile Glu Thr Phe
            660                 665                 670

gcc aag gag gaa cct aag gaa gat att gac gtc tct att ctg ccc cag     2064
Ala Lys Glu Glu Pro Lys Glu Asp Ile Asp Val Ser Ile Leu Pro Gln
        675                 680                 685

ctg gag cat tgc agc tcc agg aag atg aat aca tgg ctt ggc att ttc     2112
Leu Glu His Cys Ser Ser Arg Lys Met Asn Thr Trp Leu Gly Ile Phe
    690                 695                 700

tat ggt tac aag ggg ctg ctg ctg ctg ctg gga atc ttc ctt gct tat     2160
Tyr Gly Tyr Lys Gly Leu Leu Leu Leu Leu Gly Ile Phe Leu Ala Tyr
705                 710                 715                 720

gag acc aag agt gtg tcc act gag aag atc aat gat cac cgg gct gtg     2208
Glu Thr Lys Ser Val Ser Thr Glu Lys Ile Asn Asp His Arg Ala Val
                725                 730                 735

ggc atg gct atc tac aat gtg gca gtc ctg tgc ctc atc act gct cct     2256
Gly Met Ala Ile Tyr Asn Val Ala Val Leu Cys Leu Ile Thr Ala Pro
            740                 745                 750

gtc acc atg att ctg tcc agc cag cag gat gca gcc ttt gcc ttt gcc     2304
Val Thr Met Ile Leu Ser Ser Gln Gln Asp Ala Ala Phe Ala Phe Ala
        755                 760                 765

tct ctt gcc ata gtt ttc tcc tcc tat atc act ctt gtt gtg ctc ttt     2352
Ser Leu Ala Ile Val Phe Ser Ser Tyr Ile Thr Leu Val Val Leu Phe
    770                 775                 780

gtg ccc aag atg cgc agg ctg atc acc cga ggg gaa tgg cag tcg gag     2400
Val Pro Lys Met Arg Arg Leu Ile Thr Arg Gly Glu Trp Gln Ser Glu
785                 790                 795                 800

gcg cag gac acc atg aag aca ggg tca tcg acc aac aac aac gag gag     2448
Ala Gln Asp Thr Met Lys Thr Gly Ser Ser Thr Asn Asn Asn Glu Glu
                805                 810                 815

gag aag tcc cgg ctg ttg gag aag gag aac cgt gaa ctg gaa aag atc     2496
Glu Lys Ser Arg Leu Leu Glu Lys Glu Asn Arg Glu Leu Glu Lys Ile
            820                 825                 830

att gct gag aaa gag gag cgt gtc tct gaa ctg cgc cat caa ctc cag     2544
Ile Ala Glu Lys Glu Glu Arg Val Ser Glu Leu Arg His Gln Leu Gln
        835                 840                 845

tct cgg cag cag ctc cgc tcc cgg cgc cac cca ccg aca ccc cca gaa     2592
Ser Arg Gln Gln Leu Arg Ser Arg Arg His Pro Pro Thr Pro Pro Glu
    850                 855                 860

ccc tct ggg ggc ctg ccc agg gga ccc cct gag ccc ccc gac cgg ctt     2640
Pro Ser Gly Gly Leu Pro Arg Gly Pro Pro Glu Pro Pro Asp Arg Leu
865                 870                 875                 880

agc tgt gat ggg agt cga gtg cat ttg ctt tat aag tga                 2679
Ser Cys Asp Gly Ser Arg Val His Leu Leu Tyr Lys
                885                 890


<210> SEQ ID NO 75
<211> LENGTH: 892
<212> TYPE: PRT
<213> ORGANISM: Homo sapiens

<400> SEQUENCE: 75
```

-continued

```
Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Glu Arg Arg Ala Val Tyr Ile Gly Ala Leu Phe Pro Met Ser Gly Gly
            100                 105                 110

Trp Pro Gly Gly Gln Ala Cys Gln Pro Ala Val Glu Met Ala Leu Glu
        115                 120                 125

Asp Val Asn Ser Arg Arg Asp Ile Leu Pro Asp Tyr Glu Leu Lys Leu
    130                 135                 140

Ile His His Asp Ser Lys Cys Asp Pro Gly Gln Ala Thr Lys Tyr Leu
145                 150                 155                 160

Tyr Glu Leu Leu Tyr Asn Asp Pro Ile Lys Ile Ile Leu Met Pro Gly
                165                 170                 175

Cys Ser Ser Val Ser Thr Leu Val Ala Glu Ala Ala Arg Met Trp Asn
            180                 185                 190

Leu Ile Val Leu Ser Tyr Gly Ser Ser Ser Pro Ala Leu Ser Asn Arg
        195                 200                 205

Gln Arg Phe Pro Thr Phe Phe Arg Thr His Pro Ser Ala Thr Leu His
    210                 215                 220

Asn Pro Thr Arg Val Lys Leu Phe Glu Lys Trp Gly Trp Lys Lys Ile
225                 230                 235                 240

Ala Thr Ile Gln Gln Thr Thr Glu Val Phe Thr Ser Thr Leu Asp Asp
                245                 250                 255

Leu Glu Glu Arg Val Lys Glu Ala Gly Ile Glu Ile Thr Phe Arg Gln
            260                 265                 270

Ser Phe Phe Ser Asp Pro Ala Val Pro Val Lys Asn Leu Lys Arg Gln
        275                 280                 285

Asp Ala Arg Ile Ile Val Gly Leu Phe Tyr Glu Thr Glu Ala Arg Lys
    290                 295                 300

Val Phe Cys Glu Val Tyr Lys Glu Arg Leu Phe Gly Lys Lys Tyr Val
305                 310                 315                 320

Trp Phe Leu Ile Gly Trp Tyr Ala Asp Asn Trp Phe Lys Ile Tyr Asp
                325                 330                 335

Pro Ser Ile Asn Cys Thr Val Asp Glu Met Thr Glu Ala Val Glu Gly
            340                 345                 350

His Ile Thr Thr Glu Ile Val Met Leu Asn Pro Ala Asn Thr Arg Ser
        355                 360                 365

Ile Ser Asn Met Thr Ser Gln Glu Phe Val Glu Lys Leu Thr Lys Arg
    370                 375                 380

Leu Lys Arg His Pro Glu Glu Thr Gly Gly Phe Gln Glu Ala Pro Leu
385                 390                 395                 400

Ala Tyr Asp Ala Ile Trp Ala Leu Ala Leu Ala Leu Asn Lys Thr Ser
                405                 410                 415

Gly Gly Gly Gly Arg Ser Gly Val Arg Leu Glu Asp Phe Asn Tyr Asn
```

-continued

```
            420                 425                 430

Asn Gln Thr Ile Thr Asp Gln Ile Tyr Arg Ala Met Asn Ser Ser Ser
        435                 440                 445

Phe Glu Gly Val Ser Gly His Val Val Phe Asp Ala Ser Gly Ser Arg
    450                 455                 460

Met Ala Trp Thr Leu Ile Glu Gln Leu Gln Gly Gly Ser Tyr Lys Lys
465                 470                 475                 480

Ile Gly Tyr Tyr Asp Ser Thr Lys Asp Asp Leu Ser Trp Ser Lys Thr
                485                 490                 495

Asp Lys Trp Ile Gly Gly Ser Pro Pro Ala Asp Gln Thr Leu Val Ile
            500                 505                 510

Lys Thr Phe Arg Phe Leu Ser Gln Lys Leu Phe Ile Ser Val Ser Val
        515                 520                 525

Leu Ser Ser Leu Gly Ile Val Leu Ala Val Val Cys Leu Ser Phe Asn
    530                 535                 540

Ile Tyr Asn Ser His Val Arg Tyr Ile Gln Asn Ser Gln Pro Asn Leu
545                 550                 555                 560

Asn Asn Leu Thr Ala Val Gly Cys Ser Leu Ala Leu Ala Ala Val Phe
                565                 570                 575

Pro Leu Gly Leu Asp Gly Tyr His Ile Gly Arg Asn Gln Phe Pro Phe
            580                 585                 590

Val Cys Gln Ala Arg Leu Trp Leu Leu Gly Leu Gly Phe Ser Leu Gly
        595                 600                 605

Tyr Gly Ser Met Phe Thr Lys Ile Trp Trp Val His Thr Val Phe Thr
    610                 615                 620

Lys Lys Glu Glu Lys Lys Glu Trp Arg Lys Thr Leu Glu Pro Trp Lys
625                 630                 635                 640

Leu Tyr Ala Thr Val Gly Leu Leu Val Gly Met Asp Val Leu Thr Leu
                645                 650                 655

Ala Ile Trp Gln Ile Val Asp Pro Leu His Arg Thr Ile Glu Thr Phe
            660                 665                 670

Ala Lys Glu Glu Pro Lys Glu Asp Ile Asp Val Ser Ile Leu Pro Gln
        675                 680                 685

Leu Glu His Cys Ser Ser Arg Lys Met Asn Thr Trp Leu Gly Ile Phe
    690                 695                 700

Tyr Gly Tyr Lys Gly Leu Leu Leu Leu Leu Gly Ile Phe Leu Ala Tyr
705                 710                 715                 720

Glu Thr Lys Ser Val Ser Thr Glu Lys Ile Asn Asp His Arg Ala Val
                725                 730                 735

Gly Met Ala Ile Tyr Asn Val Ala Val Leu Cys Leu Ile Thr Ala Pro
            740                 745                 750

Val Thr Met Ile Leu Ser Ser Gln Gln Asp Ala Ala Phe Ala Phe Ala
        755                 760                 765

Ser Leu Ala Ile Val Phe Ser Ser Tyr Ile Thr Leu Val Val Leu Phe
    770                 775                 780

Val Pro Lys Met Arg Arg Leu Ile Thr Arg Gly Glu Trp Gln Ser Glu
785                 790                 795                 800

Ala Gln Asp Thr Met Lys Thr Gly Ser Ser Thr Asn Asn Asn Glu Glu
                805                 810                 815

Glu Lys Ser Arg Leu Leu Glu Lys Glu Asn Arg Glu Leu Glu Lys Ile
            820                 825                 830

Ile Ala Glu Lys Glu Glu Arg Val Ser Glu Leu Arg His Gln Leu Gln
        835                 840                 845
```

```
Ser Arg Gln Gln Leu Arg Ser Arg Arg His Pro Pro Thr Pro Pro Glu
    850                 855                 860

Pro Ser Gly Gly Leu Pro Arg Gly Pro Pro Glu Pro Pro Asp Arg Leu
865                 870                 875                 880

Ser Cys Asp Gly Ser Arg Val His Leu Leu Tyr Lys
                885                 890


<210> SEQ ID NO 76
<211> LENGTH: 2661
<212> TYPE: DNA
<213> ORGANISM: Homo sapiens
<220> FEATURE:
<221> NAME/KEY: CDS
<222> LOCATION: (1)...(2658)

<400> SEQUENCE: 76

atg ttg ctg ctg ctg cta ctg gcg cca ctc ttc ctc cgc ccc ccg ggc       48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc       96
Ala Gly Gly Ala Gln Thr Pro Asn Ala Thr Ser Glu Gly Cys Gln Ile
            20                  25                  30

ata cac ccg ccc tgg gaa ggg ggc atc agg tac cgg ggc ctg act cgg      144
Ile His Pro Pro Trp Glu Gly Gly Ile Arg Tyr Arg Gly Leu Thr Arg
        35                  40                  45

gac cag gtg aag gct atc aac ttc ctg cca gtg gac tat gag att gag      192
Asp Gln Val Lys Ala Ile Asn Phe Leu Pro Val Asp Tyr Glu Ile Glu
    50                  55                  60

tat gtg tgc cgg ggg gag cgc gag gtg gtg ggg ccc aag gtc cgc aag      240
Tyr Val Cys Arg Gly Glu Arg Glu Val Val Gly Pro Lys Val Arg Lys
 65                  70                  75                  80

tgc ctg gcc aac ggc tcc tgg aca gat atg gac aca ccc agc cgc tgt      288
Cys Leu Ala Asn Gly Ser Trp Thr Asp Met Asp Thr Pro Ser Arg Cys
                85                  90                  95

gtg aat cga acg cca cac tca gaa cgg cgc gca gtg tac atc ggg gca      336
Val Asn Arg Thr Pro His Ser Glu Arg Arg Ala Val Tyr Ile Gly Ala
            100                 105                 110

ctg ttt ccc gcg gtg gag atg gcg ctg gag gac gtg aat agc cgc agg      384
Leu Phe Pro Ala Val Glu Met Ala Leu Glu Asp Val Asn Ser Arg Arg
        115                 120                 125

gac atc ctg ccg gac tat gag ctc aag ctc atc cac cac gac agc aag      432
Asp Ile Leu Pro Asp Tyr Glu Leu Lys Leu Ile His His Asp Ser Lys
    130                 135                 140

tgt gat cca ggc caa gcc acc aag tac cta tat gag ctg ctc tac aac      480
Cys Asp Pro Gly Gln Ala Thr Lys Tyr Leu Tyr Glu Leu Leu Tyr Asn
145                 150                 155                 160

gac cct atc aag atc atc ctt atg cct ggc tgc agc tct gtc tcc acg      528
Asp Pro Ile Lys Ile Ile Leu Met Pro Gly Cys Ser Ser Val Ser Thr
                165                 170                 175

ctg gtg gct gag gct gct agg atg tgg aac ctc att gtg ctt tcc tat      576
Leu Val Ala Glu Ala Ala Arg Met Trp Asn Leu Ile Val Leu Ser Tyr
            180                 185                 190

ggc tcc agc tca cca gcc ctg tca aac cgg cag cgt ttc ccc act ttc      624
Gly Ser Ser Ser Pro Ala Leu Ser Asn Arg Gln Arg Phe Pro Thr Phe
        195                 200                 205

ttc cga acg cac cca tca gcc aca ctc cac aac cct acc cgc gtg aaa      672
Phe Arg Thr His Pro Ser Ala Thr Leu His Asn Pro Thr Arg Val Lys
    210                 215                 220

ctc ttt gaa aag tgg ggc tgg aag aag att gct acc atc cag cag acc      720
Leu Phe Glu Lys Trp Gly Trp Lys Lys Ile Ala Thr Ile Gln Gln Thr
```

-continued

```
225                 230                 235                 240

act gag gtc ttc act tcg act ctg gac gac ctg gag gaa cga gtg aag      768
Thr Glu Val Phe Thr Ser Thr Leu Asp Asp Leu Glu Glu Arg Val Lys
                245                 250                 255

gag gct gga att gag att act ttc cgc cag agt ttc ttc tca gat cca      816
Glu Ala Gly Ile Glu Ile Thr Phe Arg Gln Ser Phe Phe Ser Asp Pro
            260                 265                 270

gct gtg ccc gtc aaa aac ctg aag cgc cag gat gcc cga atc atc gtg      864
Ala Val Pro Val Lys Asn Leu Lys Arg Gln Asp Ala Arg Ile Ile Val
        275                 280                 285

gga ctt ttc tat gag act gaa gcc cgg aaa gtt ttt tgt gag gtg tac      912
Gly Leu Phe Tyr Glu Thr Glu Ala Arg Lys Val Phe Cys Glu Val Tyr
    290                 295                 300

aag gag cgt ctc ttt ggg aag aag tac gtc tgg ttc ctc att ggg tgg      960
Lys Glu Arg Leu Phe Gly Lys Lys Tyr Val Trp Phe Leu Ile Gly Trp
305                 310                 315                 320

tat gct gac aat tgg ttc aag atc tac gac cct tct atc aac tgc aca     1008
Tyr Ala Asp Asn Trp Phe Lys Ile Tyr Asp Pro Ser Ile Asn Cys Thr
                325                 330                 335

gtg gat gag atg act gag gcg gtg gag ggc cac atc aca act gag att     1056
Val Asp Glu Met Thr Glu Ala Val Glu Gly His Ile Thr Thr Glu Ile
            340                 345                 350

gtc atg ctg aat cct gcc aat acc cgc agc att tcc aac atg aca tcc     1104
Val Met Leu Asn Pro Ala Asn Thr Arg Ser Ile Ser Asn Met Thr Ser
        355                 360                 365

cag gaa ttt gtg gag aaa cta acc aag cga ctg aaa aga cac cct gag     1152
Gln Glu Phe Val Glu Lys Leu Thr Lys Arg Leu Lys Arg His Pro Glu
    370                 375                 380

gag aca gga ggc ttc cag gag gca ccg ctg gcc tat gat gcc atc tgg     1200
Glu Thr Gly Gly Phe Gln Glu Ala Pro Leu Ala Tyr Asp Ala Ile Trp
385                 390                 395                 400

gcc ttg gca ctg gcc ctg aac aag aca tct gga gga ggc ggc cgt tct     1248
Ala Leu Ala Leu Ala Leu Asn Lys Thr Ser Gly Gly Gly Gly Arg Ser
                405                 410                 415

ggt gtg cgc ctg gag gac ttc aac tac aac aac cag acc att acc gac     1296
Gly Val Arg Leu Glu Asp Phe Asn Tyr Asn Asn Gln Thr Ile Thr Asp
            420                 425                 430

caa atc tac cgg gca atg aac tct tcg tcc ttt gag ggt gtc tct ggc     1344
Gln Ile Tyr Arg Ala Met Asn Ser Ser Ser Phe Glu Gly Val Ser Gly
        435                 440                 445

cat gtg gtg ttt gat gcc agc ggc tct cgg atg gca tgg acg ctt atc     1392
His Val Val Phe Asp Ala Ser Gly Ser Arg Met Ala Trp Thr Leu Ile
    450                 455                 460

gag cag ctt cag ggt ggc agc tac aag aag att ggc tac tat gac agc     1440
Glu Gln Leu Gln Gly Gly Ser Tyr Lys Lys Ile Gly Tyr Tyr Asp Ser
465                 470                 475                 480

acc aag gat gat ctt tcc tgg tcc aaa aca gat aaa tgg att gga ggg     1488
Thr Lys Asp Asp Leu Ser Trp Ser Lys Thr Asp Lys Trp Ile Gly Gly
                485                 490                 495

tcc ccc cca gct gac cag acc ctg gtc atc aag aca ttc cgc ttc ctg     1536
Ser Pro Pro Ala Asp Gln Thr Leu Val Ile Lys Thr Phe Arg Phe Leu
            500                 505                 510

tca cag aaa ctc ttt atc tcc gtc tca gtt ctc tcc agc ctg ggc att     1584
Ser Gln Lys Leu Phe Ile Ser Val Ser Val Leu Ser Ser Leu Gly Ile
        515                 520                 525

gtc cta gct gtt gtc tgt ctg tcc ttt aac atc tac aac tca cat gtc     1632
Val Leu Ala Val Val Cys Leu Ser Phe Asn Ile Tyr Asn Ser His Val
    530                 535                 540

cgt tat atc cag aac tca cag ccc aac ctg aac aac ctg act gct gtg     1680
```

-continued

```
Arg Tyr Ile Gln Asn Ser Gln Pro Asn Leu Asn Asn Leu Thr Ala Val
545                 550                 555                 560

ggc tgc tca ctg gct tta gct gct gtc ttc ccc ctg ggg ctc gat ggt     1728
Gly Cys Ser Leu Ala Leu Ala Ala Val Phe Pro Leu Gly Leu Asp Gly
                565                 570                 575

tac cac att ggg agg aac cag ttt cct ttc gtc tgc cag gcc cgc ctc     1776
Tyr His Ile Gly Arg Asn Gln Phe Pro Phe Val Cys Gln Ala Arg Leu
            580                 585                 590

tgg ctc ctg ggc ctg ggc ttt agt ctg ggc tac ggt tcc atg ttc acc     1824
Trp Leu Leu Gly Leu Gly Phe Ser Leu Gly Tyr Gly Ser Met Phe Thr
        595                 600                 605

aag att tgg tgg gtc cac acg gtc ttc aca aag aag gaa gaa aag aag     1872
Lys Ile Trp Trp Val His Thr Val Phe Thr Lys Lys Glu Glu Lys Lys
    610                 615                 620

gag tgg agg aag act ctg gaa ccc tgg aag ctg tat gcc aca gtg ggc     1920
Glu Trp Arg Lys Thr Leu Glu Pro Trp Lys Leu Tyr Ala Thr Val Gly
625                 630                 635                 640

ctg ctg gtg ggc atg gat gtc ctc act ctc gcc atc tgg cag atc gtg     1968
Leu Leu Val Gly Met Asp Val Leu Thr Leu Ala Ile Trp Gln Ile Val
                645                 650                 655

gac cct ctg cac cgg acc att gag aca ttt gcc aag gag gaa cct aag     2016
Asp Pro Leu His Arg Thr Ile Glu Thr Phe Ala Lys Glu Glu Pro Lys
            660                 665                 670

gaa gat att gac gtc tct att ctg ccc cag ctg gag cat tgc agc tcc     2064
Glu Asp Ile Asp Val Ser Ile Leu Pro Gln Leu Glu His Cys Ser Ser
        675                 680                 685

agg aag atg aat aca tgg ctt ggc att ttc tat ggt tac aag ggg ctg     2112
Arg Lys Met Asn Thr Trp Leu Gly Ile Phe Tyr Gly Tyr Lys Gly Leu
    690                 695                 700

ctg ctg ctg ctg gga atc ttc ctt gct tat gag acc aag agt gtg tcc     2160
Leu Leu Leu Leu Gly Ile Phe Leu Ala Tyr Glu Thr Lys Ser Val Ser
705                 710                 715                 720

act gag aag atc aat gat cac cgg gct gtg ggc atg gct atc tac aat     2208
Thr Glu Lys Ile Asn Asp His Arg Ala Val Gly Met Ala Ile Tyr Asn
                725                 730                 735

gtg gca gtc ctg tgc ctc atc act gct cct gtc acc atg att ctg tcc     2256
Val Ala Val Leu Cys Leu Ile Thr Ala Pro Val Thr Met Ile Leu Ser
            740                 745                 750

agc cag cag gat gca gcc ttt gcc ttt gcc tct ctt gcc ata gtt ttc     2304
Ser Gln Gln Asp Ala Ala Phe Ala Phe Ala Ser Leu Ala Ile Val Phe
        755                 760                 765

tcc tcc tat atc act ctt gtt gtg ctc ttt gtg ccc aag atg cgc agg     2352
Ser Ser Tyr Ile Thr Leu Val Val Leu Phe Val Pro Lys Met Arg Arg
    770                 775                 780

ctg atc acc cga ggg gaa tgg cag tcg gag gcg cag gac acc atg aag     2400
Leu Ile Thr Arg Gly Glu Trp Gln Ser Glu Ala Gln Asp Thr Met Lys
785                 790                 795                 800

aca ggg tca tcg acc aac aac aac gag gag gag aag tcc cgg ctg ttg     2448
Thr Gly Ser Ser Thr Asn Asn Asn Glu Glu Glu Lys Ser Arg Leu Leu
                805                 810                 815

gag aag gag aac cgt gaa ctg gaa aag atc att gct gag aaa gag gag     2496
Glu Lys Glu Asn Arg Glu Leu Glu Lys Ile Ile Ala Glu Lys Glu Glu
            820                 825                 830

cgt gtc tct gaa ctg cgc cat caa ctc cag tct cgg cag cag ctc cgc     2544
Arg Val Ser Glu Leu Arg His Gln Leu Gln Ser Arg Gln Gln Leu Arg
        835                 840                 845

tcc cgg cgc cac cca ccg aca ccc cca gaa ccc tct ggg ggc ctg ccc     2592
Ser Arg Arg His Pro Pro Thr Pro Pro Glu Pro Ser Gly Gly Leu Pro
    850                 855                 860
```

-continued

```
agg gga ccc cct gag ccc ccc gac cgg ctt agc tgt gat ggg agt cga     2640
Arg Gly Pro Pro Glu Pro Pro Asp Arg Leu Ser Cys Asp Gly Ser Arg
865                 870                 875                 880

gtg cat ttg ctt tat aag tga                                         2661
Val His Leu Leu Tyr Lys
                885


<210> SEQ ID NO 77
<211> LENGTH: 886
<212> TYPE: PRT
<213> ORGANISM: Homo sapiens

<400> SEQUENCE: 77

Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Asn Arg Thr Pro His Ser Glu Arg Arg Ala Val Tyr Ile Gly Ala
            100                 105                 110

Leu Phe Pro Ala Val Glu Met Ala Leu Glu Asp Val Asn Ser Arg Arg
        115                 120                 125

Asp Ile Leu Pro Asp Tyr Glu Leu Lys Leu Ile His His Asp Ser Lys
    130                 135                 140

Cys Asp Pro Gly Gln Ala Thr Lys Tyr Leu Tyr Glu Leu Leu Tyr Asn
145                 150                 155                 160

Asp Pro Ile Lys Ile Ile Leu Met Pro Gly Cys Ser Ser Val Ser Thr
                165                 170                 175

Leu Val Ala Glu Ala Ala Arg Met Trp Asn Leu Ile Val Leu Ser Tyr
            180                 185                 190

Gly Ser Ser Ser Pro Ala Leu Ser Asn Arg Gln Arg Phe Pro Thr Phe
        195                 200                 205

Phe Arg Thr His Pro Ser Ala Thr Leu His Asn Pro Thr Arg Val Lys
    210                 215                 220

Leu Phe Glu Lys Trp Gly Trp Lys Lys Ile Ala Thr Ile Gln Gln Thr
225                 230                 235                 240

Thr Glu Val Phe Thr Ser Thr Leu Asp Asp Leu Glu Glu Arg Val Lys
                245                 250                 255

Glu Ala Gly Ile Glu Ile Thr Phe Arg Gln Ser Phe Phe Ser Asp Pro
            260                 265                 270

Ala Val Pro Val Lys Asn Leu Lys Arg Gln Asp Ala Arg Ile Ile Val
        275                 280                 285

Gly Leu Phe Tyr Glu Thr Glu Ala Arg Lys Val Phe Cys Glu Val Tyr
    290                 295                 300

Lys Glu Arg Leu Phe Gly Lys Lys Tyr Val Trp Phe Leu Ile Gly Trp
305                 310                 315                 320

Tyr Ala Asp Asn Trp Phe Lys Ile Tyr Asp Pro Ser Ile Asn Cys Thr
                325                 330                 335
```

-continued

```
Val Asp Glu Met Thr Glu Ala Val Glu Gly His Ile Thr Thr Glu Ile
            340                 345                 350

Val Met Leu Asn Pro Ala Asn Thr Arg Ser Ile Ser Asn Met Thr Ser
        355                 360                 365

Gln Glu Phe Val Glu Lys Leu Thr Lys Arg Leu Lys Arg His Pro Glu
    370                 375                 380

Glu Thr Gly Gly Phe Gln Glu Ala Pro Leu Ala Tyr Asp Ala Ile Trp
385                 390                 395                 400

Ala Leu Ala Leu Ala Leu Asn Lys Thr Ser Gly Gly Gly Gly Arg Ser
                405                 410                 415

Gly Val Arg Leu Glu Asp Phe Asn Tyr Asn Asn Gln Thr Ile Thr Asp
            420                 425                 430

Gln Ile Tyr Arg Ala Met Asn Ser Ser Ser Phe Glu Gly Val Ser Gly
        435                 440                 445

His Val Val Phe Asp Ala Ser Gly Ser Arg Met Ala Trp Thr Leu Ile
    450                 455                 460

Glu Gln Leu Gln Gly Gly Ser Tyr Lys Lys Ile Gly Tyr Tyr Asp Ser
465                 470                 475                 480

Thr Lys Asp Asp Leu Ser Trp Ser Lys Thr Asp Lys Trp Ile Gly Gly
                485                 490                 495

Ser Pro Pro Ala Asp Gln Thr Leu Val Ile Lys Thr Phe Arg Phe Leu
            500                 505                 510

Ser Gln Lys Leu Phe Ile Ser Val Ser Val Leu Ser Ser Leu Gly Ile
        515                 520                 525

Val Leu Ala Val Val Cys Leu Ser Phe Asn Ile Tyr Asn Ser His Val
    530                 535                 540

Arg Tyr Ile Gln Asn Ser Gln Pro Asn Leu Asn Asn Leu Thr Ala Val
545                 550                 555                 560

Gly Cys Ser Leu Ala Leu Ala Ala Val Phe Pro Leu Gly Leu Asp Gly
                565                 570                 575

Tyr His Ile Gly Arg Asn Gln Phe Pro Phe Val Cys Gln Ala Arg Leu
            580                 585                 590

Trp Leu Leu Gly Leu Gly Phe Ser Leu Gly Tyr Gly Ser Met Phe Thr
        595                 600                 605

Lys Ile Trp Trp Val His Thr Val Phe Thr Lys Lys Glu Glu Lys Lys
    610                 615                 620

Glu Trp Arg Lys Thr Leu Glu Pro Trp Lys Leu Tyr Ala Thr Val Gly
625                 630                 635                 640

Leu Leu Val Gly Met Asp Val Leu Thr Leu Ala Ile Trp Gln Ile Val
                645                 650                 655

Asp Pro Leu His Arg Thr Ile Glu Thr Phe Ala Lys Glu Glu Pro Lys
            660                 665                 670

Glu Asp Ile Asp Val Ser Ile Leu Pro Gln Leu Glu His Cys Ser Ser
        675                 680                 685

Arg Lys Met Asn Thr Trp Leu Gly Ile Phe Tyr Gly Tyr Lys Gly Leu
    690                 695                 700

Leu Leu Leu Leu Gly Ile Phe Leu Ala Tyr Glu Thr Lys Ser Val Ser
705                 710                 715                 720

Thr Glu Lys Ile Asn Asp His Arg Ala Val Gly Met Ala Ile Tyr Asn
                725                 730                 735

Val Ala Val Leu Cys Leu Ile Thr Ala Pro Val Thr Met Ile Leu Ser
            740                 745                 750

Ser Gln Gln Asp Ala Ala Phe Ala Phe Ala Ser Leu Ala Ile Val Phe
```

-continued

```
        755                 760                 765

Ser Ser Tyr Ile Thr Leu Val Val Leu Phe Val Pro Lys Met Arg Arg
    770                 775                 780

Leu Ile Thr Arg Gly Glu Trp Gln Ser Glu Ala Gln Asp Thr Met Lys
785                 790                 795                 800

Thr Gly Ser Ser Thr Asn Asn Asn Glu Glu Glu Lys Ser Arg Leu Leu
                805                 810                 815

Glu Lys Glu Asn Arg Glu Leu Glu Lys Ile Ile Ala Glu Lys Glu Glu
            820                 825                 830

Arg Val Ser Glu Leu Arg His Gln Leu Gln Ser Arg Gln Gln Leu Arg
        835                 840                 845

Ser Arg Arg His Pro Pro Thr Pro Pro Glu Pro Ser Gly Gly Leu Pro
    850                 855                 860

Arg Gly Pro Pro Glu Pro Pro Asp Arg Leu Ser Cys Asp Gly Ser Arg
865                 870                 875                 880

Val His Leu Leu Tyr Lys
                885


<210> SEQ ID NO 78
<211> LENGTH: 1692
<212> TYPE: DNA
<213> ORGANISM: Homo sapiens
<220> FEATURE:
<221> NAME/KEY: CDS
<222> LOCATION: (1)...(1689)

<400> SEQUENCE: 78

atg ttg ctg ctg ctg cta ctg gcg cca ctc ttc ctc cgc ccc ccg ggc       48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc       96
Ala Gly Gly Ala Gln Thr Pro Asn Ala Thr Ser Glu Gly Cys Gln Ile
             20                  25                  30

ata cac ccg ccc tgg gaa ggg ggc atc agg tac cgg ggc ctg act cgg      144
Ile His Pro Pro Trp Glu Gly Gly Ile Arg Tyr Arg Gly Leu Thr Arg
         35                  40                  45

gac cag gtg aag gct atc aac ttc ctg cca gtg gac tat gag att gag      192
Asp Gln Val Lys Ala Ile Asn Phe Leu Pro Val Asp Tyr Glu Ile Glu
     50                  55                  60

tat gtg tgc cgg ggg gag cgc gag gtg gtg ggg ccc aag gtc cgc aag      240
Tyr Val Cys Arg Gly Glu Arg Glu Val Val Gly Pro Lys Val Arg Lys
 65                  70                  75                  80

tgc ctg gcc aac ggc tcc tgg aca gat atg gac aca ccc agc cgc tgt      288
Cys Leu Ala Asn Gly Ser Trp Thr Asp Met Asp Thr Pro Ser Arg Cys
                 85                  90                  95

gtc cga atc tgc tcc aag tct tat ttg acc att acc gac caa atc tac      336
Val Arg Ile Cys Ser Lys Ser Tyr Leu Thr Ile Thr Asp Gln Ile Tyr
            100                 105                 110

cgg gca atg aac tct tcg tcc ttt gag ggt gtc tct ggc cat gtg gtg      384
Arg Ala Met Asn Ser Ser Ser Phe Glu Gly Val Ser Gly His Val Val
        115                 120                 125

ttt gat gcc agc ggc tct cgg atg gca tgg acg ctt atc gag cag ctt      432
Phe Asp Ala Ser Gly Ser Arg Met Ala Trp Thr Leu Ile Glu Gln Leu
    130                 135                 140

cag ggt ggc agc tac aag aag att ggc tac tat gac agc acc aag gat      480
Gln Gly Gly Ser Tyr Lys Lys Ile Gly Tyr Tyr Asp Ser Thr Lys Asp
145                 150                 155                 160

gat ctt tcc tgg tcc aaa aca gat aaa tgg att gga ggg tcc ccc cca      528
Asp Leu Ser Trp Ser Lys Thr Asp Lys Trp Ile Gly Gly Ser Pro Pro
```

-continued

```
            165                 170                 175

gct gac cag acc ctg gtc atc aag aca ttc cgc ttc ctg tca cag aaa      576
Ala Asp Gln Thr Leu Val Ile Lys Thr Phe Arg Phe Leu Ser Gln Lys
        180                 185                 190

ctc ttt atc tcc gtc tca gtt ctc tcc agc ctg ggc att gtc cta gct      624
Leu Phe Ile Ser Val Ser Val Leu Ser Ser Leu Gly Ile Val Leu Ala
    195                 200                 205

gtt gtc tgt ctg tcc ttt aac atc tac aac tca cat gtc cgt tat atc      672
Val Val Cys Leu Ser Phe Asn Ile Tyr Asn Ser His Val Arg Tyr Ile
    210                 215                 220

cag aac tca cag ccc aac ctg aac aac ctg act gct gtg ggc tgc tca      720
Gln Asn Ser Gln Pro Asn Leu Asn Asn Leu Thr Ala Val Gly Cys Ser
225                 230                 235                 240

ctg gct tta gct gct gtc ttc ccc ctg ggg ctc gat ggt tac cac att      768
Leu Ala Leu Ala Ala Val Phe Pro Leu Gly Leu Asp Gly Tyr His Ile
            245                 250                 255

ggg agg aac cag ttt cct ttc gtc tgc cag gcc cgc ctc tgg ctc ctg      816
Gly Arg Asn Gln Phe Pro Phe Val Cys Gln Ala Arg Leu Trp Leu Leu
        260                 265                 270

ggc ctg ggc ttt agt ctg ggc tac ggt tcc atg ttc acc aag att tgg      864
Gly Leu Gly Phe Ser Leu Gly Tyr Gly Ser Met Phe Thr Lys Ile Trp
    275                 280                 285

tgg gtc cac acg gtc ttc aca aag aag gaa gaa aag aag gag tgg agg      912
Trp Val His Thr Val Phe Thr Lys Lys Glu Glu Lys Lys Glu Trp Arg
    290                 295                 300

aag act ctg gaa ccc tgg aag ctg tat gcc aca gtg ggc ctg ctg gtg      960
Lys Thr Leu Glu Pro Trp Lys Leu Tyr Ala Thr Val Gly Leu Leu Val
305                 310                 315                 320

ggc atg gat gtc ctc act ctc gcc atc tgg cag atc gtg gac cct ctg     1008
Gly Met Asp Val Leu Thr Leu Ala Ile Trp Gln Ile Val Asp Pro Leu
            325                 330                 335

cac cgg acc att gag aca ttt gcc aag gag gaa cct aag gaa gat att     1056
His Arg Thr Ile Glu Thr Phe Ala Lys Glu Glu Pro Lys Glu Asp Ile
        340                 345                 350

gac gtc tct att ctg ccc cag ctg gag cat tgc agc tcc agg aag atg     1104
Asp Val Ser Ile Leu Pro Gln Leu Glu His Cys Ser Ser Arg Lys Met
    355                 360                 365

aat aca tgg ctt ggc att ttc tat ggt tac aag ggg ctg ctg ctg ctg     1152
Asn Thr Trp Leu Gly Ile Phe Tyr Gly Tyr Lys Gly Leu Leu Leu Leu
    370                 375                 380

ctg gga atc ttc ctt gct tat gag acc aag agt gtg tcc act gag aag     1200
Leu Gly Ile Phe Leu Ala Tyr Glu Thr Lys Ser Val Ser Thr Glu Lys
385                 390                 395                 400

atc aat gat cac cgg gct gtg ggc atg gct atc tac aat gtg gca gtc     1248
Ile Asn Asp His Arg Ala Val Gly Met Ala Ile Tyr Asn Val Ala Val
            405                 410                 415

ctg tgc ctc atc act gct cct gtc acc atg att ctg tcc agc cag cag     1296
Leu Cys Leu Ile Thr Ala Pro Val Thr Met Ile Leu Ser Ser Gln Gln
        420                 425                 430

gat gca gcc ttt gcc ttt gcc tct ctt gcc ata gtt ttc tcc tcc tat     1344
Asp Ala Ala Phe Ala Phe Ala Ser Leu Ala Ile Val Phe Ser Ser Tyr
    435                 440                 445

atc act ctt gtt gtg ctc ttt gtg ccc aag atg cgc agg ctg atc acc     1392
Ile Thr Leu Val Val Leu Phe Val Pro Lys Met Arg Arg Leu Ile Thr
    450                 455                 460

cga ggg gaa tgg cag tcg gag gcg cag gac acc atg aag aca ggg tca     1440
Arg Gly Glu Trp Gln Ser Glu Ala Gln Asp Thr Met Lys Thr Gly Ser
465                 470                 475                 480

tcg acc aac aac aac gag gag gag aag tcc cgg ctg ttg gag aag gag     1488
```

-continued

```
Ser Thr Asn Asn Asn Glu Glu Glu Lys Ser Arg Leu Leu Glu Lys Glu
                485                 490                 495

aac cgt gaa ctg gaa aag atc att gct gag aaa gag gag cgt gtc tct     1536
Asn Arg Glu Leu Glu Lys Ile Ile Ala Glu Lys Glu Glu Arg Val Ser
            500                 505                 510

gaa ctg cgc cat caa ctc cag tct cgg cag cag ctc cgc tcc cgg cgc     1584
Glu Leu Arg His Gln Leu Gln Ser Arg Gln Gln Leu Arg Ser Arg Arg
        515                 520                 525

cac cca ccg aca ccc cca gaa ccc tct ggg ggc ctg ccc agg gga ccc     1632
His Pro Pro Thr Pro Pro Glu Pro Ser Gly Gly Leu Pro Arg Gly Pro
    530                 535                 540

cct gag ccc ccc gac cgg ctt agc tgt gat ggg agt cga gtg cat ttg     1680
Pro Glu Pro Pro Asp Arg Leu Ser Cys Asp Gly Ser Arg Val His Leu
545                 550                 555                 560

ctt tat aag tga                                                     1692
Leu Tyr Lys


<210> SEQ ID NO 79
<211> LENGTH: 563
<212> TYPE: PRT
<213> ORGANISM: Homo sapiens

<400> SEQUENCE: 79

Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Ile Thr Asp Gln Ile Tyr
            100                 105                 110

Arg Ala Met Asn Ser Ser Ser Phe Glu Gly Val Ser Gly His Val Val
        115                 120                 125

Phe Asp Ala Ser Gly Ser Arg Met Ala Trp Thr Leu Ile Glu Gln Leu
    130                 135                 140

Gln Gly Gly Ser Tyr Lys Lys Ile Gly Tyr Tyr Asp Ser Thr Lys Asp
145                 150                 155                 160

Asp Leu Ser Trp Ser Lys Thr Asp Lys Trp Ile Gly Gly Ser Pro Pro
                165                 170                 175

Ala Asp Gln Thr Leu Val Ile Lys Thr Phe Arg Phe Leu Ser Gln Lys
            180                 185                 190

Leu Phe Ile Ser Val Ser Val Leu Ser Ser Leu Gly Ile Val Leu Ala
        195                 200                 205

Val Val Cys Leu Ser Phe Asn Ile Tyr Asn Ser His Val Arg Tyr Ile
    210                 215                 220

Gln Asn Ser Gln Pro Asn Leu Asn Asn Leu Thr Ala Val Gly Cys Ser
225                 230                 235                 240

Leu Ala Leu Ala Ala Val Phe Pro Leu Gly Leu Asp Gly Tyr His Ile
                245                 250                 255

Gly Arg Asn Gln Phe Pro Phe Val Cys Gln Ala Arg Leu Trp Leu Leu
```

-continued

```
            260                 265                 270

Gly Leu Gly Phe Ser Leu Gly Tyr Gly Ser Met Phe Thr Lys Ile Trp
        275                 280                 285

Trp Val His Thr Val Phe Thr Lys Lys Glu Glu Lys Lys Glu Trp Arg
    290                 295                 300

Lys Thr Leu Glu Pro Trp Lys Leu Tyr Ala Thr Val Gly Leu Leu Val
305                 310                 315                 320

Gly Met Asp Val Leu Thr Leu Ala Ile Trp Gln Ile Val Asp Pro Leu
                325                 330                 335

His Arg Thr Ile Glu Thr Phe Ala Lys Glu Glu Pro Lys Glu Asp Ile
            340                 345                 350

Asp Val Ser Ile Leu Pro Gln Leu Glu His Cys Ser Ser Arg Lys Met
        355                 360                 365

Asn Thr Trp Leu Gly Ile Phe Tyr Gly Tyr Lys Gly Leu Leu Leu Leu
    370                 375                 380

Leu Gly Ile Phe Leu Ala Tyr Glu Thr Lys Ser Val Ser Thr Glu Lys
385                 390                 395                 400

Ile Asn Asp His Arg Ala Val Gly Met Ala Ile Tyr Asn Val Ala Val
                405                 410                 415

Leu Cys Leu Ile Thr Ala Pro Val Thr Met Ile Leu Ser Ser Gln Gln
            420                 425                 430

Asp Ala Ala Phe Ala Phe Ala Ser Leu Ala Ile Val Phe Ser Ser Tyr
        435                 440                 445

Ile Thr Leu Val Val Leu Phe Val Pro Lys Met Arg Arg Leu Ile Thr
    450                 455                 460

Arg Gly Glu Trp Gln Ser Glu Ala Gln Asp Thr Met Lys Thr Gly Ser
465                 470                 475                 480

Ser Thr Asn Asn Asn Glu Glu Glu Lys Ser Arg Leu Leu Glu Lys Glu
                485                 490                 495

Asn Arg Glu Leu Glu Lys Ile Ile Ala Glu Lys Glu Glu Arg Val Ser
            500                 505                 510

Glu Leu Arg His Gln Leu Gln Ser Arg Gln Gln Leu Arg Ser Arg Arg
        515                 520                 525

His Pro Pro Thr Pro Pro Glu Pro Ser Gly Gly Leu Pro Arg Gly Pro
    530                 535                 540

Pro Glu Pro Pro Asp Arg Leu Ser Cys Asp Gly Ser Arg Val His Leu
545                 550                 555                 560

Leu Tyr Lys


<210> SEQ ID NO 80
<211> LENGTH: 2602
<212> TYPE: DNA
<213> ORGANISM: Homo sapiens
<220> FEATURE:
<221> NAME/KEY: CDS
<222> LOCATION: (1)...(315)

<400> SEQUENCE: 80

atg ttg ctg ctg ctg cta ctg gcg cca ctc ttc ctc cgc ccc ccg ggc       48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc       96
Ala Gly Gly Ala Gln Thr Pro Asn Ala Thr Ser Glu Gly Cys Gln Ile
            20                  25                  30

ata cac ccg ccc tgg gaa ggg ggc atc agg tac cgg ggc ctg act cgg      144
Ile His Pro Pro Trp Glu Gly Gly Ile Arg Tyr Arg Gly Leu Thr Arg
```

-continued

```
         35                  40                  45

gac cag gtg aag gct atc aac ttc ctg cca gtg gac tat gag att gat      192
Asp Gln Val Lys Ala Ile Asn Phe Leu Pro Val Asp Tyr Glu Ile Asp
     50                  55                  60

gaa tcg aac gcc aca ctc aga acg gcg cgc agt gta cat cgg ggc act      240
Glu Ser Asn Ala Thr Leu Arg Thr Ala Arg Ser Val His Arg Gly Thr
 65                  70                  75                  80

gtt tcc cat gag cgg ggg ctg gcc agg ggg cca ggc ctg cca gcc cgc      288
Val Ser His Glu Arg Gly Leu Ala Arg Gly Pro Gly Leu Pro Ala Arg
                 85                  90                  95

ggt gga gat ggc gct gga gga cgt gaa tagccgcagg gacatcctgc            335
Gly Gly Asp Gly Ala Gly Gly Arg Glu
            100                 105

cggactatga gctcaagctc atccaccacg acagcaagtg tgatccaggc caagccacca    395

agtacctata tgagctgctc tacaacgacc ctatcaagat catccttatg cctggctgca    455

gctctgtctc cacgctggtg gctgaggctg ctaggatgtg gaacctcatt gtgctttcct    515

atggctccag ctcaccagcc ctgtcaaacc ggcagcgttt ccccactttc ttccgaacgc    575

acccatcagc cacactccac aaccctaccc gcgtgaaact ctttgaaaag tggggctgga    635

agaagattgc taccatccag cagaccactg aggtcttcac ttcgactctg gacgacctgg    695

aggaacgagt gaaggaggct ggaattgaga ttactttccg ccagagtttc ttctcagatc    755

cagctgtgcc cgtcaaaaac ctgaagcgcc aggatgcccg aatcatcgtg ggacttttct    815

atgagactga agcccggaaa gtttttttgtg aggtgtacaa ggagcgtctc tttgggaaga   875

agtacgtctg gttcctcatt gggtggtatg ctgacaattg gttcaagatc tacgaccctt    935

ctatcaactg cacagtggat gagatgactg aggcggtgga gggccacatc acaactgaga    995

ttgtcatgct gaatcctgcc aatacccgca gcatttccaa catgacatcc caggaatttg   1055

tggagaaact aaccaagcga ctgaaaagac accctgagga gacaggaggc ttccaggagg   1115

caccgctggc ctatgatgcc atctgggcct tggcactggc cctgaacaag acatctggag   1175

gaggcggccg ttctggtgtg cgcctggagg acttcaacta caacaaccag accattaccg   1235

accaaatcta ccgggcaatg aactcttcgt cctttgaggg tgtctctggc catgtggtgt   1295

ttgatgccag cggctctcgg atggcatgga cgcttatcga gcagcttcag ggtggcagct   1355

acaagaagat tggctactat gacagcacca aggatgatct ttcctggtcc aaaacagata   1415

aatggattgg agggtccccc ccagctgacc agaccctggt catcaagaca ttccgcttcc   1475

tgtcacagaa actctttatc tccgtctcag ttctctccag cctgggcatt gtcctagctg   1535

ttgtctgtct gtcctttaac atctacaact cacatgtccg ttatatccag aactcacagc   1595

ccaacctgaa caacctgact gctgtgggct gctcactggc tttagctgct gtcttccccc   1655

tggggctcga tggttaccac attgggagga accagtttcc tttcgtctgc caggcccgcc   1715

tctggctcct gggcctgggc tttagtctgg gctacggttc catgttcacc aagatttggt   1775

gggtccacac ggtcttcaca aagaaggaag aaaagaagga gtggaggaag actctggaac   1835

cctggaagct gtatgccaca gtgggcctgc tggtgggcat ggatgtcctc actctcgcca   1895

tctggcagat cgtggaccct ctgcaccgga ccattgagac atttgccaag gaggaaccta   1955

aggaagatat tgacgtctct attctgcccc agctggagca ttgcagctcc aggaagatga   2015

atacatggct tggcattttc tatggttaca aggggctgct gctgctgctg ggaatcttcc   2075

ttgcttatga gaccaagagt gtgtccactg agaagatcaa tgatcaccgg gctgtgggca   2135

tggctatcta caatgtggca gtcctgtgcc tcatcactgc tcctgtcacc atgattctgt   2195
```

```
ccagccagca ggatgcagcc tttgcctttg cctctcttgc catagttttc tcctcctata   2255

tcactcttgt tgtgctcttt gtgcccaaga tgcgcaggct gatcacccga ggggaatggc   2315

agtcggaggc gcaggacacc atgaagacag ggtcatcgac caacaacaac gaggaggaga   2375

agtcccggct gttggagaag gagaaccgtg aactggaaaa gatcattgct gagaaagagg   2435

agcgtgtctc tgaactgcgc catcaactcc agtctcggca gcagctccgc tcccggcgcc   2495

acccaccgac acccccagaa ccctctgggg gcctgcccag ggaccccct gagcccccg    2555

accggcttag ctgtgatggg agtcgagtgc atttgcttta taagtga                2602
```

```
<210> SEQ ID NO 81
<211> LENGTH: 105
<212> TYPE: PRT
<213> ORGANISM: Homo sapiens

<400> SEQUENCE: 81

Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Asp
    50                  55                  60

Glu Ser Asn Ala Thr Leu Arg Thr Ala Arg Ser Val His Arg Gly Thr
65                  70                  75                  80

Val Ser His Glu Arg Gly Leu Ala Arg Gly Pro Gly Leu Pro Ala Arg
                85                  90                  95

Gly Gly Asp Gly Ala Gly Gly Arg Glu
            100                 105
```

```
<210> SEQ ID NO 82
<211> LENGTH: 2367
<212> TYPE: DNA
<213> ORGANISM: Homo sapiens
<220> FEATURE:
<221> NAME/KEY: CDS
<222> LOCATION: (1)...(291)

<400> SEQUENCE: 82

atg ttg ctg ctg ctg cta ctg gcg cca ctc ttc ctc cgc ccc ccg ggc      48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc      96
Ala Gly Gly Ala Gln Thr Pro Asn Ala Thr Ser Glu Gly Cys Gln Ile
            20                  25                  30

ata cac ccg ccc tgg gaa ggg ggc atc agg tac cgg ggc ctg act cgg     144
Ile His Pro Pro Trp Glu Gly Gly Ile Arg Tyr Arg Gly Leu Thr Arg
        35                  40                  45

gac cag gtg aag gct atc aac ttc ctg cca gtg gac tat gag att gag     192
Asp Gln Val Lys Ala Ile Asn Phe Leu Pro Val Asp Tyr Glu Ile Glu
    50                  55                  60

tat gtg tgc cgg ggg gag cgc gag gtg gtg ggg ccc aag gtc cgc aag     240
Tyr Val Cys Arg Gly Glu Arg Glu Val Val Gly Pro Lys Val Arg Lys
65                  70                  75                  80

tgc ctg gcc aac ggc tcc tgg aca gat atg gac aca ccc agc cgc tgt     288
Cys Leu Ala Asn Gly Ser Trp Thr Asp Met Asp Thr Pro Ser Arg Cys
                85                  90                  95
```

-continued

```
gtg tgatccaggc caagccacca agtacctata tgagctgctc tacaacgacc          341
Val

ctatcaagat catccttatg cctggctgca gctctgtctc cacgctggtg gctgaggctg    401

ctaggatgtg gaacctcatt gtgctttcct atggctccag ctcaccagcc ctgtcaaacc    461

ggcagcgttt ccccactttc ttccgaacgc acccatcagc cacactccac aaccctaccc    521

gcgtgaaact ctttgaaaag tggggctgga agaagattgc taccatccag cagaccactg    581

aggtcttcac ttcgactctg gacgacctgg aggaacgagt gaaggaggct ggaattgaga    641

ttactttccg ccagagtttc ttctcagatc cagctgtgcc cgtcaaaaac ctgaagcgcc    701

aggatgcccg aatcatcgtg ggacttttct atgagactga agcccggaaa gtttttttgtg    761

aggtgtacaa ggagcgtctc tttgggaaga agtacgtctg gttcctcatt gggtggtatg    821

ctgacaattg gttcaagatc tacgaccctt ctatcaactg cacagtggat gagatgactg    881

aggcggtgga gggccacatc acaactgaga ttgtcatgct gaatcctgcc aatacccgca    941

gcatttccaa catgacatcc caggaatttg tggagaaact aaccaagcga ctgaaaagac   1001

accctgagga gacaggaggc ttccaggagg caccgctggc ctatgatgcc atctgggcct   1061

tggcactggc cctgaacaag acatctggag gaggcggccg ttctggtgtg cgcctggagg   1121

acttcaacta caacaaccag accattaccg accaaatcta ccgggcaatg aactcttcgt   1181

cctttgaggg tgtctctggc catgtggtgt ttgatgccag cggctctcgg atggcatgga   1241

cgcttatcga gcagcttcag ggtggcagct acaagaagat tggctactat gacagcacca   1301

aggatgatct ttcctggtcc aaaacagata aatggattgt tatatccaga actcacagcc   1361

caacctgaac aacctgactg ctgtgggctg ctcactggct ttagctgctg tcttccccct   1421

ggggctcgat ggttaccaca ttgggaggaa ccagtttcct ttcgtctgcc aggcccgcct   1481

ctggctcctg ggcctgggct ttagtctggg ctacggttcc atgttcacca agatttggtg   1541

ggtccacacg gtcttcacaa agaaggaaga aaagaaggag tggaggaaga ctctggaacc   1601

ctggaagctg tatgccacag tgggcctgct ggtgggcatg gatgtcctca ctctcgccat   1661

ctggcagatc gtggaccctc tgcaccggac cattgagaca tttgccaagg aggaacctaa   1721

ggaagatatt gacgtctcta ttctgcccca gctggagcat tgcagctcca ggaagatgaa   1781

tacatggctt ggcattttct atggttacaa ggggctgctg ctgctgctgg gaatcttcct   1841

tgcttatgag accaagagtg tgtccactga gaagatcaat gatcaccggg ctgtgggcat   1901

ggctatctac aatgtggcag tcctgtgcct catcactgct cctgtcacca tgattctgtc   1961

cagccagcag gatgcagcct ttgcctttgc ctctcttgcc atagttttct cctcctatat   2021

cactcttgtt gtgctctttg tgcccaagat gcgcaggctg atcacccgag ggaatggca    2081

gtcggaggcg caggacacca tgaagacagg gtcatcgacc aacaacaacg aggaggagaa   2141

gtcccggctg ttggagaagg agaaccgtga actggaaaag atcattgctg agaaagagga   2201

gcgtgtctct gaactgcgcc atcaactcca gtctcggcag cagctccgct cccggcgcca   2261

cccaccgaca cccccagaac cctctggggg cctgcccagg ggacccccctg agccccccga  2321

ccggcttagc tgtgatggga gtcgagtgca tttgctttat aagtga                  2367
```

<210> SEQ ID NO 83
<211> LENGTH: 97
<212> TYPE: PRT
<213> ORGANISM: Homo sapiens

<400> SEQUENCE: 83

-continued

```
Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val


<210> SEQ ID NO 84
<211> LENGTH: 2489
<212> TYPE: DNA
<213> ORGANISM: Homo sapiens
<220> FEATURE:
<221> NAME/KEY: CDS
<222> LOCATION: (1)...(1488)

<400> SEQUENCE: 84

atg ttg ctg ctg ctg cta ctg gcg cca ctc ttc ctc cgc ccc ccg ggc       48
Met Leu Leu Leu Leu Leu Leu Ala Pro Leu Phe Leu Arg Pro Pro Gly
 1               5                  10                  15

gcg ggc ggg gcg cag acc ccc aac gcc acc tca gaa ggt tgc cag atc       96
Ala Gly Gly Ala Gln Thr Pro Asn Ala Thr Ser Glu Gly Cys Gln Ile
            20                  25                  30

ata cac ccg ccc tgg gaa ggg ggc atc agg tac cgg ggc ctg act cgg      144
Ile His Pro Pro Trp Glu Gly Gly Ile Arg Tyr Arg Gly Leu Thr Arg
        35                  40                  45

gac cag gtg aag gct atc aac ttc ctg cca gtg gac tat gag att gag      192
Asp Gln Val Lys Ala Ile Asn Phe Leu Pro Val Asp Tyr Glu Ile Glu
    50                  55                  60

tat gtg tgc cgg ggg gag cgc gag gtg gtg ggg ccc aag gtc cgc aag      240
Tyr Val Cys Arg Gly Glu Arg Glu Val Val Gly Pro Lys Val Arg Lys
65                  70                  75                  80

tgc ctg gcc aac ggc tcc tgg aca gat atg gac aca ccc agc cgc tgt      288
Cys Leu Ala Asn Gly Ser Trp Thr Asp Met Asp Thr Pro Ser Arg Cys
                85                  90                  95

gtc cga atc tgc tcc aag tct tat ttg acc ctg gaa aat ggg aag gtt      336
Val Arg Ile Cys Ser Lys Ser Tyr Leu Thr Leu Glu Asn Gly Lys Val
            100                 105                 110

ttc ctg acg ggt ggg gac ctc cca gct ctg gac gga gcc cgg gtg gat      384
Phe Leu Thr Gly Gly Asp Leu Pro Ala Leu Asp Gly Ala Arg Val Asp
        115                 120                 125

ttc cgg tgt gac ccc gac ttc cat ctg tgt gat cca ggc caa gcc acc      432
Phe Arg Cys Asp Pro Asp Phe His Leu Cys Asp Pro Gly Gln Ala Thr
    130                 135                 140

aag tac cta tat gag ctg ctc tac aac gac cct atc aag atc atc ctt      480
Lys Tyr Leu Tyr Glu Leu Leu Tyr Asn Asp Pro Ile Lys Ile Ile Leu
145                 150                 155                 160

atg cct ggc tgc agc tct gtc tcc acg ctg gtg gct gag gct gct agg      528
Met Pro Gly Cys Ser Ser Val Ser Thr Leu Val Ala Glu Ala Ala Arg
                165                 170                 175

atg tgg aac ctc att gtg ctt tcc tat ggc tcc agc tca cca gcc ctg      576
Met Trp Asn Leu Ile Val Leu Ser Tyr Gly Ser Ser Ser Pro Ala Leu
            180                 185                 190
```

-continued

```
tca aac cgg cag cgt ttc ccc act ttc ttc cga acg cac cca tca gcc      624
Ser Asn Arg Gln Arg Phe Pro Thr Phe Phe Arg Thr His Pro Ser Ala
        195                 200                 205

aca ctc cac aac cct acc cgc gtg aaa ctc ttt gaa aag tgg ggc tgg      672
Thr Leu His Asn Pro Thr Arg Val Lys Leu Phe Glu Lys Trp Gly Trp
    210                 215                 220

aag aag att gct acc atc cag cag acc act gag gtc ttc act tcg act      720
Lys Lys Ile Ala Thr Ile Gln Gln Thr Thr Glu Val Phe Thr Ser Thr
225                 230                 235                 240

ctg gac gac ctg gag gaa cga gtg aag gag gct gga att gag att act      768
Leu Asp Asp Leu Glu Glu Arg Val Lys Glu Ala Gly Ile Glu Ile Thr
                245                 250                 255

ttc cgc cag agt ttc ttc tca gat cca gct gtg ccc gtc aaa aac ctg      816
Phe Arg Gln Ser Phe Phe Ser Asp Pro Ala Val Pro Val Lys Asn Leu
            260                 265                 270

aag cgc cag gat gcc cga atc atc gtg gga ctt ttc tat gag act gaa      864
Lys Arg Gln Asp Ala Arg Ile Ile Val Gly Leu Phe Tyr Glu Thr Glu
        275                 280                 285

gcc cgg aaa gtt ttt tgt gag gtg tac aag gag cgt ctc ttt ggg aag      912
Ala Arg Lys Val Phe Cys Glu Val Tyr Lys Glu Arg Leu Phe Gly Lys
    290                 295                 300

aag tac gtc tgg ttc ctc att ggg tgg tat gct gac aat tgg ttc aag      960
Lys Tyr Val Trp Phe Leu Ile Gly Trp Tyr Ala Asp Asn Trp Phe Lys
305                 310                 315                 320

atc tac gac cct tct atc aac tgc aca gtg gat gag atg act gag gcg     1008
Ile Tyr Asp Pro Ser Ile Asn Cys Thr Val Asp Glu Met Thr Glu Ala
                325                 330                 335

gtg gag ggc cac atc aca act gag att gtc atg ctg aat cct gcc aat     1056
Val Glu Gly His Ile Thr Thr Glu Ile Val Met Leu Asn Pro Ala Asn
            340                 345                 350

acc cgc agc att tcc aac atg aca tcc cag gaa ttt gtg gag aaa cta     1104
Thr Arg Ser Ile Ser Asn Met Thr Ser Gln Glu Phe Val Glu Lys Leu
        355                 360                 365

acc aag cga ctg aaa aga cac cct gag gag aca gga ggc ttc cag gag     1152
Thr Lys Arg Leu Lys Arg His Pro Glu Glu Thr Gly Gly Phe Gln Glu
    370                 375                 380

gca ccg ctg gcc tat gat gcc atc tgg gcc ttg gca ctg gcc ctg aac     1200
Ala Pro Leu Ala Tyr Asp Ala Ile Trp Ala Leu Ala Leu Ala Leu Asn
385                 390                 395                 400

aag aca tct gga gga ggc ggc cgt tct ggt gtg cgc ctg gag gac ttc     1248
Lys Thr Ser Gly Gly Gly Gly Arg Ser Gly Val Arg Leu Glu Asp Phe
                405                 410                 415

aac tac aac aac cag acc att acc gac caa atc tac cgg gca atg aac     1296
Asn Tyr Asn Asn Gln Thr Ile Thr Asp Gln Ile Tyr Arg Ala Met Asn
            420                 425                 430

tct tcg tcc ttt gag ggt gtc tct ggc cat gtg gtg ttt gat gcc agc     1344
Ser Ser Ser Phe Glu Gly Val Ser Gly His Val Val Phe Asp Ala Ser
        435                 440                 445

ggc tct cgg atg gca tgg acg ctt atc gag cag ctt cag ggt ggc agc     1392
Gly Ser Arg Met Ala Trp Thr Leu Ile Glu Gln Leu Gln Gly Gly Ser
    450                 455                 460

tac aag aag att ggc tac tat gac agc acc aag gat gat ctt tcc tgg     1440
Tyr Lys Lys Ile Gly Tyr Tyr Asp Ser Thr Lys Asp Asp Leu Ser Trp
465                 470                 475                 480

tcc aaa aca gat aaa tgg att gtt ata tcc aga act cac agc cca acc     1488
Ser Lys Thr Asp Lys Trp Ile Val Ile Ser Arg Thr His Ser Pro Thr
                485                 490                 495

tgaacaacct gactgctgtg ggctgctcac tggctttagc tgctgtcttc cccctggggc   1548

tcgatggtta ccacattggg aggaaccagt ttcctttcgt ctgccaggcc cgcctctggc   1608
```

-continued

```
tcctgggcct gggctttagt ctgggctacg gttccatgtt caccaagatt tggtgggtcc   1668

acacggtctt cacaaagaag gaagaaaaga aggagtggag gaagactctg gaaccctgga   1728

agctgtatgc cacagtgggc ctgctggtgg gcatggatgt cctcactctc gccatctggc   1788

agatcgtgga ccctctgcac cggaccattg agacatttgc caaggaggaa cctaaggaag   1848

atattgacgt ctctattctg ccccagctgg agcattgcag ctccaggaag atgaatacat   1908

ggcttggcat tttctatggt tacaaggggc tgctgctgct gctgggaatc ttccttgctt   1968

atgagaccaa gagtgtgtcc actgagaaga tcaatgatca ccgggctgtg ggcatggcta   2028

tctacaatgt ggcagtcctg tgcctcatca ctgctcctgt caccatgatt ctgtccagcc   2088

agcaggatgc agcctttgcc tttgcctctc ttgccatagt tttctcctcc tatatcactc   2148

ttgttgtgct ctttgtgccc aagatgcgca ggctgatcac ccgaggggaa tggcagtcgg   2208

aggcgcagga caccatgaag acagggtcat cgaccaacaa caacgaggag gagaagtccc   2268

ggctgttgga gaaggagaac cgtgaactgg aaaagatcat tgctgagaaa gaggagcgtg   2328

tctctgaact gcgccatcaa ctccagtctc ggcagcagct ccgctcccgg cgccacccac   2388

cgacaccccc agaaccctct gggggcctgc ccaggggacc ccctgagccc cccgaccggc   2448

ttagctgtga tgggagtcga gtgcatttgc tttataagtg a                       2489
```

<210> SEQ ID NO 85
<211> LENGTH: 496
<212> TYPE: PRT
<213> ORGANISM: Homo sapiens

<400> SEQUENCE: 85

```
Met Leu Leu Leu Leu Leu Leu Ala Pro Leu Phe Leu Arg Pro Pro Gly
 1               5                  10                  15

Ala Gly Gly Ala Gln Thr Pro Asn Ala Thr Ser Glu Gly Cys Gln Ile
            20                  25                  30

Ile His Pro Pro Trp Glu Gly Gly Ile Arg Tyr Arg Gly Leu Thr Arg
        35                  40                  45

Asp Gln Val Lys Ala Ile Asn Phe Leu Pro Val Asp Tyr Glu Ile Glu
    50                  55                  60

Tyr Val Cys Arg Gly Glu Arg Glu Val Val Gly Pro Lys Val Arg Lys
65                  70                  75                  80

Cys Leu Ala Asn Gly Ser Trp Thr Asp Met Asp Thr Pro Ser Arg Cys
                85                  90                  95

Val Arg Ile Cys Ser Lys Ser Tyr Leu Thr Leu Glu Asn Gly Lys Val
            100                 105                 110

Phe Leu Thr Gly Gly Asp Leu Pro Ala Leu Asp Gly Ala Arg Val Asp
        115                 120                 125

Phe Arg Cys Asp Pro Asp Phe His Leu Cys Asp Pro Gly Gln Ala Thr
    130                 135                 140

Lys Tyr Leu Tyr Glu Leu Leu Tyr Asn Asp Pro Ile Lys Ile Ile Leu
145                 150                 155                 160

Met Pro Gly Cys Ser Ser Val Ser Thr Leu Val Ala Glu Ala Ala Arg
                165                 170                 175

Met Trp Asn Leu Ile Val Leu Ser Tyr Gly Ser Ser Ser Pro Ala Leu
            180                 185                 190

Ser Asn Arg Gln Arg Phe Pro Thr Phe Phe Arg Thr His Pro Ser Ala
        195                 200                 205

Thr Leu His Asn Pro Thr Arg Val Lys Leu Phe Glu Lys Trp Gly Trp
```

-continued

```
    210                 215                 220

Lys Lys Ile Ala Thr Ile Gln Gln Thr Thr Glu Val Phe Thr Ser Thr
225                 230                 235                 240

Leu Asp Asp Leu Glu Glu Arg Val Lys Glu Ala Gly Ile Glu Ile Thr
                245                 250                 255

Phe Arg Gln Ser Phe Phe Ser Asp Pro Ala Val Pro Val Lys Asn Leu
            260                 265                 270

Lys Arg Gln Asp Ala Arg Ile Ile Val Gly Leu Phe Tyr Glu Thr Glu
        275                 280                 285

Ala Arg Lys Val Phe Cys Glu Val Tyr Lys Glu Arg Leu Phe Gly Lys
    290                 295                 300

Lys Tyr Val Trp Phe Leu Ile Gly Trp Tyr Ala Asp Asn Trp Phe Lys
305                 310                 315                 320

Ile Tyr Asp Pro Ser Ile Asn Cys Thr Val Asp Glu Met Thr Glu Ala
                325                 330                 335

Val Glu Gly His Ile Thr Thr Glu Ile Val Met Leu Asn Pro Ala Asn
            340                 345                 350

Thr Arg Ser Ile Ser Asn Met Thr Ser Gln Glu Phe Val Glu Lys Leu
        355                 360                 365

Thr Lys Arg Leu Lys Arg His Pro Glu Glu Thr Gly Gly Phe Gln Glu
    370                 375                 380

Ala Pro Leu Ala Tyr Asp Ala Ile Trp Ala Leu Ala Leu Ala Leu Asn
385                 390                 395                 400

Lys Thr Ser Gly Gly Gly Gly Arg Ser Gly Val Arg Leu Glu Asp Phe
                405                 410                 415

Asn Tyr Asn Asn Gln Thr Ile Thr Asp Gln Ile Tyr Arg Ala Met Asn
            420                 425                 430

Ser Ser Ser Phe Glu Gly Val Ser Gly His Val Val Phe Asp Ala Ser
        435                 440                 445

Gly Ser Arg Met Ala Trp Thr Leu Ile Glu Gln Leu Gln Gly Gly Ser
    450                 455                 460

Tyr Lys Lys Ile Gly Tyr Tyr Asp Ser Thr Lys Asp Asp Leu Ser Trp
465                 470                 475                 480

Ser Lys Thr Asp Lys Trp Ile Val Ile Ser Arg Thr His Ser Pro Thr
                485                 490                 495
```

NUCLEOTIDE SEQUENCES

CROSS REFERENCE TO RELATED APPLICATION

This application is a continuation-in-part of U.S. Ser. No. 09/242,608, filed Feb. 19, 1999, now abandoned which claims priority to PCT/SE98/01947 filed Oct. 27, 1998, and Swedish application Nos. 9703914-2, filed Oct. 27, 1997; 9800864-2, filed Mar. 16, 1998; and 9802575-2, filed Jul. 17, 1998.

FIELD OF THE INVENTION

The invention relates to nucleic acid molecules encoding $GABA_B$ receptors, and to methods for screening for compounds that are inhibitors of transient lower esophageal sphincter relaxations (TLESR).

BACKGROUND OF THE INVENTION $GABA_B$ Receptors

GABA (4-aminobutanoic acid) is an endogenous neurotransmitter in the central and peripheral nervous systems. Receptors for GABA have traditionally been divided into $GABA_A$ and $GABA_B$ receptor subtypes. $GABA_B$ receptors (for a review see Kerr, D. I. B. and Ong, J. (1995) Pharmac. Ther. vol. 67, pp.187–246) belong to the superfamily of G-protein coupled receptors. $GABA_B$ receptor agonists are useful in the treatment of central nervous system (CNS) disorders, such as for inducing muscle relaxation in spinal spasticity, cardiovascular disorders, asthma, and gut motility disorders such as irritable bowel syndrome; and as prokinetic and anti-tussive agents. $GABA_B$ receptor agonists have also been disclosed as useful in the treatment of emesis (WO 96/11680).

The cloning of the rat $GABA_B$ receptors $GABA_BR1a$ (SEQ ID NOs: 44 and 45) and $GABA_BR1b$ (SEQ ID NOs: 46 and 47) was disclosed by Kaupmann et al. ((1997) Nature, vol. 386, 239–246). The mature rat $GABA_BR1b$ differs from $GABA_BR1a$ in that the N-terminal 147 residues are replaced by 18 different residues. It is thought that the rat $GABA_BR1a$ and $GABA_BR1b$ receptor variants are derived from the same gene by alternative splicing. Cloning of the human $GABA_BR1b$ receptor was disclosed in WO97/46675.

Reflux

In some humans, the lower esophageal sphincter (LES) is prone to relaxing more frequently than in other humans. As a consequence, fluid from the stomach can pass into the esophagus because the mechanical barrier is temporarily lost at such times, an event hereinafter referred to as "reflux."

Gastro-esophageal reflux disease (GERD) is the most prevalent upper gastrointestinal tract disease. Conventional therapies have sought to reduce gastric acid secretion, or reduce esophageal acid exposure by enhancing esophageal clearance, lower esophageal sphincter tone, and gastric emptying. The major mechanism behind reflux has been considered to depend on a hypotonic lower esophageal sphincter. However, recent research (e.g., Holloway & Dent (1990) Gastroenterol. Clin. N. Amer. 19, 517–535) has shown that most reflux episodes occur during transient lower esophageal sphincter relaxations (TLESR), i.e., relaxations not triggered by swallowing. It has also been shown that gastric acid secretion usually is normal in patients with GERD.

SUMMARY OF THE INVENTION

The present invention provides nucleic acid molecules encoding human and canine $GABA_B$ receptors. These nucleic acid molecules make it possible to screen for compounds that are agonists or antagonists of $GABA_B$ receptors, e.g., to identify compounds which are inhibitors of TLESR.

Consequently, the invention provides an isolated nucleic acid molecule encoding a human or canine $GABA_B$ receptor, or a conservative variant thereof. An "isolated nucleic acid" is a nucleic acid the structure of which is not identical to that of any naturally occurring nucleic acid or to that of any fragment of a naturally occurring genomic nucleic acid spanning more than three separate genes. The term therefor covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones: e.g., as these occur in a DNA library such as a cDNA or genomic DNA library.

In various embodiments, the nucleic acid molecule encodes a human $GABA_B$ receptor 1a (SEQ ID NOs: 48 and 49), 1b (SEQ ID NOs: 50 and 51), 1c (SEQ ID NOs: 54 and 55) or 1d (SEQ ID NOs: 56 and 57); or a canine $GABA_B$ receptor 1a (SEQ ID NOs: 52 and 53) or 1c (SEQ ID NOs: 58 and 59). Accordingly, the invention includes the following nucleic acid molecules:

(1) a nucleic acid molecule that includes a nucleotide sequence set forth as SEQ ID NO: 48, 50, 52, 54, 56, or 58, or a degenerate variant thereof;

(2) an RNA molecule that includes a nucleotide sequence set forth as SEQ ID NO: 48, 50, 52, 54, 56, or 58, or a degenerate variant thereof, wherein T is replaced by U;

(3) a nucleic acid molecule that includes a nucleotide sequence that is capable of hybridizing under stringent conditions (e.g., is complementary) to a nucleotide sequence of (1) or (2), or to the complement of (1) or (2); and (4) nucleic acid fragments that are at least 15 base pairs in length and which hybridize under stringent conditions to genomic DNA encoding the human or canine $GABA_B$ polypeptides described herein, or to the complement of such genomic DNA.

The invention also includes isolated nucleic acid molecules corresponding to genomic sequences encoding human $GABA_B$ receptors (SEQ ID NOs: 60 and 61), as well as nucleic acid molecules (set forth as SEQ ID NO: 70, 72, 74, 76, 78, 80, 82, and 84) encoding additional isoforms of the human $GABA_B$ receptor, which isoforms are generated by alternative splicing.

The nucleic acid molecules of the invention are not limited strictly to molecules including the sequences set forth as SEQ ID NOs: 48, 50, 52, 54, 56 or 58. Rather, the invention encompasses nucleic acid molecules carrying modifications such as substitutions, small deletions, insertions, or inversions, which nevertheless encode proteins having substantially the biochemical activity of the $GABA_B$ receptors according to the invention, and/or which can serve as hybridization probes for identifying a nucleic acid with one of the disclosed sequences. Included in the invention are nucleic acid molecules, the nucleotide sequence of which is at least 95% identical (e.g., at least 96%, 97%, 98%, or 99% identical) to the nucleotide sequence shown as SEQ ID NO: 48, 50, 52, 54, 56, or 58 in the Sequence Listing.

The determination of percent identity or homology between two sequences is accomplished using the algorithm of Karlin and Altschul (1990) *Proc. Nat'l Acad. Sci. USA* 87: 2264–2268, modified as in Karlin and Altschul (1993) *Proc. Nat'l Acad. Sci. USA* 90:5873–5877. Such an algorithm is incorporated into the NBLAST and XBLAST programs of Altschul et al. (1990) *J. Mol. Biol.* 215:403–410. BLAST nucleotide searches are performed with the NBLAST program, score=100, wordlength=12 to obtain nucleotide sequences homologous to the nucleic acid molecules of the invention. BLAST protein searches are performed with the XBLAST program, score=50, wordlength=3 to obtain amino acid sequences homologous to the protein molecules of the invention. To obtain gapped alignments for comparison purposes, Gapped BLAST is utilized as described in Altschul et al. (1997) *Nucleic Acids Res.* 25: 3389–3402. When utilizing BLAST and Gapped BLAST programs, the default parameters of the respective programs (e.g., XBLAST and NBLAST) are used. See http://www.ncbi.nlm.nih.gov.

The term "stringent hybridization conditions" is known in the art from standard protocols (e.g., Current Protocols in Molecular Biology, editors F. Ausubel et al., John Wiley and Sons, Inc. 1994) and is to be understood as conditions as stringent as those defined by the following: hybridization to filter-bound DNA in 0.5 M $NaHPO_4$ (pH 7.2), 7% sodium dodecyl sulfate (SDS), 1 mM EDTA at +65° C., and washing in 0.1×SSC/0.1% SDS at +68° C.

Also included in the invention is a nucleic acid molecule that has a nucleotide sequence which is a degenerate variant of a nucleic acid disclosed herein, e.g., SEQ ID NOs: 48, 50, 52, 54, 56, and 58. A sequential grouping of three nucleotides, a "codon," encodes one amino acid. Since there are 64 possible codons, but only 20 natural amino acids, most amino acids are encoded by more than one codon. This natural "degeneracy" or "redundancy" of the genetic code is well known in the art. It will thus be appreciated that the nucleic acid sequences shown in the Sequence Listing provide only an example within a large but definite group of nucleic acid sequences that will encode the polypeptides as described above.

The invention also includes an isolated polypeptide encoded by a nucleic acid of the invention. An "isolated" polypeptide is a polypeptide that is substantially free from the proteins and other naturally occurring organic molecules with which it is naturally associated. Purity can be measured by any art-known method, e.g., column chromatography, polyacrylamide gel electrophoresis, or HPLC.

An isolated polypeptide may be obtained, for example, by extraction from a natural source (e.g., a human cell); by expression of a recombinant nucleic acid encoding the polypeptide; or by chemical synthesis of the polypeptide. In the context of a polypeptide obtained by extraction from a natural source, "substantially free" means that the polypeptide constitutes at least 60% (e.g., at least 75%, 90%, or 99%) of the dry weight of the preparation. A protein that is chemically synthesized, or produced from a source different from the source from which the protein naturally originates, is by definition substantially free from its naturally associated components. Thus, an isolated polypeptide includes recombinant polypeptides synthesized, for example, in vivo, e.g., in the milk of transgenic animals, or in vitro, e.g., in a mammalian cell line, in *E. coli* or another single-celled microorganism, or in insect cells.

In various embodiments, the polypeptide of the invention has an amino acid sequence as set forth in SEQ ID NO: 49, 51, 53 55, 57, 59, 71, 73, 75, 77, 79, 81, 83, and 85. However, polypeptides of the present invention are not to limited to those having an amino acid sequence identical to one of SEQ ID NOs: 49, 51, 53, 55, 59, 71, 73, 75, 77, 79, 81, 83, or 85 in the Sequence Listing. Rather, the invention also encompasses conservative variants of the disclosed sequences. "Conservative variants" include substitutions within the following groups: glycine and alanine; valine, alanine, isoleucine, and leucine; aspartic acid and glutamic acid; asparagine, glutamine, serine, and threonine; lysine, arginine, and histidine; and phenylalanine and tyrosine.

Also included in the invention are polypeptides carrying modifications such as substitutions, small deletions, insertions, or inversions, which polypeptides nevertheless have substantially the biological activities of the $GABA_B$ receptor. Consequently, included in the invention is a polypeptide, the amino acid sequence of which is at least 95% identical (e.g., at least 96%, 97%, 98%, or 99% identical) to an amino acid sequence set forth as SEQ ID NO: 49, 51, 53, 55, 57 59, 71, 73, 75, 77, 79, 81, 83, or 85 in the Sequence Listing. "Percent identity" is defined in accordance with the algorithm described above.

Also included in the invention are polypeptides of the invention that have been post-translationally modified, e.g., by cleavage of an N-terminal signal sequence, which can be, e.g., 1 to 25 amino acids long.

The invention also includes a vector that contains a nucleic acid molecule of the present invention. The vector can, e.g., be a replicable expression vector that is capable of mediating the expression of a nucleic acid molecule of the invention. A "replicable" vector is able to replicate in a given type of host cell into which it has been introduced. Examples of suitable vectors include virus-based vectors (e.g., bacteriophages, retroviruses, adenoviruses, herpes viruses, polio viruses, and vaccinia viruses), cosmids, plasmids, and other recombination vectors. Nucleic acid molecules can be inserted into vectors by methods well known in the art.

Also included in the invention is a host cell harboring a nucleic acid (e.g., on a vector) of the invention. Without limitation, such a host cell can be a prokaryotic cell, a unicellular eukaryotic cell, or a cell derived from a multicellular organism. For example, the host cell can be a bacterial cell, such as an *E. coli* cell; a yeast cell, such as *Saccharomyces cerevisiae* or *Pichia pastoris*; an insect cell, an amphibian cell (e.g., a frog oocyte), or a mammalian cell. It is preferably not a neuron, e.g., a human, dog, rat or other mammalian neuron. Conventional methods can be employed to introduce the vector into the host cell.

Host cells containing nucleic acids of the invention can be used to produce a $GABA_B$ receptor polypeptide of the invention or a conservative variant thereof. Generally, the process includes culturing a host cell as defined above under conditions such that the polypeptide is produced, and recovering the polypeptide.

A further aspect of the invention is a method for determining whether a test compound is an inhibitor of TLESR. The method entails (a) expressing in a cell (preferably a cell that does not naturally express the $GABA_B$ receptor, such as a fibroblast or other non-neural cell) a nucleic acid molecule that includes a nucleotide sequence of the invention, thereby producing a cell having on its surface a $GABA_B$ receptor or a conservative variant thereof; (b) contacting the $GABA_B$ receptor or conservative variant with a test compound; and (c) detecting binding of the test compound to the $GABA_B$ receptor or conservative variant, wherein binding of the test compound to the $GABA_B$ receptor or conservative variant indicates that the test compound is an inhibitor of TLESR. This activity can be further validated by other in vitro or in vivo tests: e.g., by administration of the test compound to an animal model for this condition. It should be understood that this aspect of the invention is not limited to use of human and canine $GABA_B$ receptors, but rather encompasses the use of any $GABA_B$ receptor for screening for compounds which are inhibitors of TLESRs.

Nucleic acid molecules encoding human or canine $GABA_B$ receptors also can be used in a related method for screening for compounds that are agonists or antagonists. Generally, in this method, binding is detected by detecting activation, or inhibition of activation, of the $GABA_B$ receptor or a conservative variant thereof, wherein activation indicates that the test compound is an agonist of the $GABA_B$ receptor, and inhibition of activation indicates that the test compound is an antagonist of the $GABA_B$ receptor.

The screening methods according to the invention can e.g., comprise the steps (a) transforming a cultured cell with a nucleic acid molecule encoding a $GABA_B$ receptor, so that a $GABA_B$ receptor is expressed on the surface of the cell; (b) contacting a test compound with the cell; and (c) determining whether the test compound binds to, and/or activates, the $GABA_B$ receptor.

$GABA_B$ receptor-expressing cells, transgenic animals, or cells and tissues derived therefrom can be used to screen substance libraries (i.e., libraries of test compounds) for antagonist or agonist activity. For this purpose, $GABA_B$ receptor expression may be directed to cells and tissues containing, either naturally or artificially, the necessary components allowing correct receptor transport and processing as well as coupling to second messenger pathways. Screening may be performed as ligand binding assays or functional assays. For screening, cells and tissues can be prepared in various ways, each uniquely suited to its purpose. Ligand binding assays can be performed in vivo or in vitro using, e.g., radiolabelled GABA. Functional assays (e.g., $Ca^{++}$-responses, cAMP-responses, and effects on $K^+$ channels) can be performed in living cells, broken cells, isolated cell membranes, tissues, or living animals. To facilitate measurement of physiological $GABA_B$ receptor mediated responses, $GABA_B$ receptors may be co-expressed with promiscuous G-proteins, e.g., $G\alpha 16$ or Gqi5, increasing G-protein coupling. Another way to increase G-protein coupling is to fuse the $GABA_B$ receptor to appropriate G-proteins using standard molecular techniques. To further improve readouts in $Ca^{++}$-response assays, $GABA_B$ receptors can be co-expresses with aequorin, a photoprotein cloned from the luminescent jellyfish *Aequorea victoria.*

The invention also provides a pharmaceutical composition that includes a $GABA_B$ receptor (e.g., a soluble receptor), or a conservative variant thereof, and at least one of (a) a pharmaceutically acceptable carrier and (b) a pharmaceutically acceptable diluent.

The pharmaceutical composition can be used in methods of treating conditions involving GABA-dysfunction, e.g., epilepsy, psychiatric disorders such as depression and anxiety, cognitive dysfunction, gastroesophageal reflux disease, emesis, irritable bowel syndrome, dyspepsia, spasticity, arthritis, allergies, autoimmune diseases, neoplastic diseases, pain, and infectious diseases. Typically, the $GABA_B$ receptor is a soluble form of the $GABA_B$ receptor, such as the human $GABA_B$ receptor 1c or 1d or a conservative variant thereof.

A soluble form of the receptor can be a form that lacks some or all of the membrane-spanning domains of the wild-type receptor protein, but retains the ligand-binding portion or portions of the receptor. The membrane-spanning domains are readily identified by their predominance of non-polar amino acid residues, and/or by comparison with related receptors (e.g., other G-protein receptors).

Soluble forms of the $GABA_B$ receptor can be produced by culturing a host cell containing a vector that includes a nucleic acid encoding the soluble $GABA_B$ receptor under conditions such that the $GABA_B$ receptor polypeptide is produced. The polypeptide then is recovered, and a pharmaceutical composition containing the polypeptide is administered to a mammal (e.g., a human or dog) in need thereof.

In a related aspect, the invention provides a method for diagnosing a mammal as having a condition involving altered levels of $GABA_B$ receptors in body fluid (e.g., serum or cerebrospinal fluid). Such conditions include epilepsy, psychiatric disorders, cognitive dysfunction, gastroesophageal reflux disease, emesis, irritable bowel syndrome, dyspepsia, spasticity, arthritis, allergies, auto immune diseases, neoplastic diseases, pain, and infectious diseases. Diagnosis involves measuring the level of $GABA_B$ receptor in a body fluid of a mammal (e.g., a human), wherein an increase or decrease in the level of $GABA_B$ receptor, relative to the level found in a normal mammal, indicates that the mammal has a condition involving altered levels of $GABA_B$ receptors in body fluid.

Throughout this description, the terms "standard protocols" and "standard procedures," when used in the context of molecular cloning techniques, are to be understood as protocols and procedures found in an ordinary laboratory manual such as *Current Protocols in Molecular Biology*, editors F. Ausubel et al., John Wiley and Sons, Inc. 1994, or Sambrook, J., Fritsch, E. F. and Maniatis, T., Molecular Cloning: A laboratory manual, 2nd Ed., Cold Spring Harbor Laboratory Press, Cold Spring Harbor, N.Y. 1989.

Figure 1:
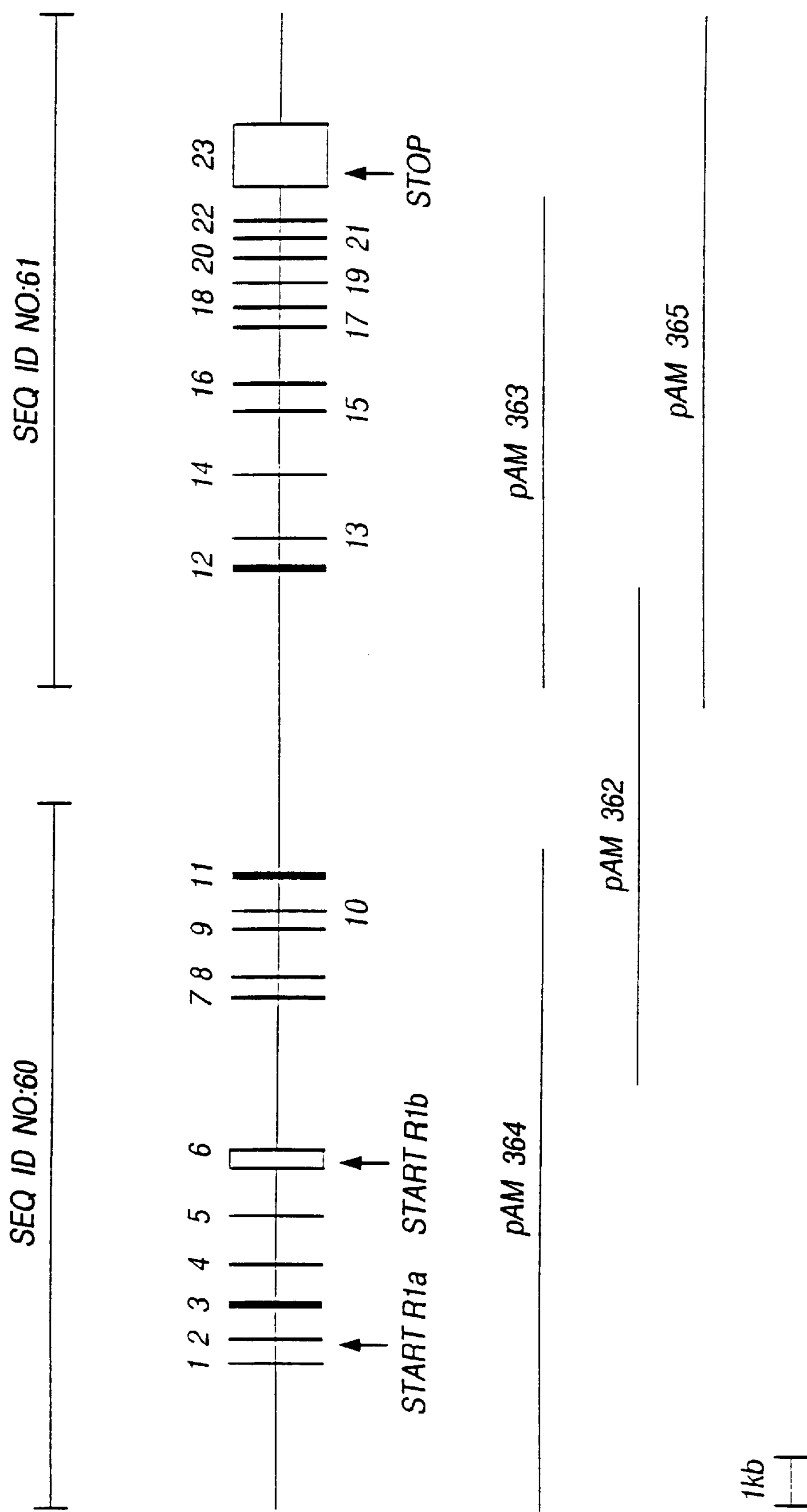
FIG. 1 is a map of the human $GABA_B$ receptor gene. The exon/intron organization is shown. Exons are indicated as solid boxes numbered 1–23. The part of intron 5 that is retained together with exon 6 giving rise to $GABA_B$ receptor 1b is indicated as an open box.

Lane 3: Lysate from an IPTG-induced *E. coli* culture transformed with an expression construct encoding an unrelated protein. Lane 4: An aliquot of the BSA-conjugated peptide used for immunization was loaded on the gel as a positive antibody control.

DETAILED DESCRIPTION

EXAMPLE 1A

Cloning and Sequencing of cDNA Encoding Human $GABA_B$ Receptor 1a and 1b

Messenger RNA from human hippocampus was obtained from Clontech (Palo Alto, Calif., USA) (catalog #6578-1). First-strand cDNA synthesis reactions were performed using the First-strand™ cDNA Synthesis kit from Amersham Pharmacia Biotech (Uppsala, Sweden). The $pd(N)_6$ primer was used to prime the first-strand synthesis. The generated cDNA molecules were used as templates in the PCR reactions described below.

Specific PCR primers were designed (as shown in Table 1) based on the sequences of the rat $GABA_B$ receptor 1a and 1b cDNA (Kaupmann et al., 1997, EMBL accession numbers Y10369 (SEQ ID NO: 44) and Y10370 (SEQ ID NO: 46)). Various cDNA fragments encoding parts of the human $GABA_B$ receptors were amplified directly by PCR using the designed primers with the generated cDNA molecules as templates. All PCR experiments were carried out using Perkin Elmer Taq DNA polymerase with Gene Amp™ (Roche Molecular Systems Inc., NJ, USA) with the following PCR program: +95° C. for 1 minute, +50° C. for 30 seconds, +72° C. for 3 minutes, repeated 44 times, and then +72° C. for 7 minutes. The following combinations of primers gave PCR products with the expected sizes: primers 838 and 842, 838 and 795, 797 and 865, 864 and 865, and 864 and 863, which correspond to the 5'-end of the $GABA_B$ receptor 1a cDNA. The combinations of 932 and 831, 932 and 796, and 794 and 831 produced PCR products that correspond to the 3-ends of both $GABA_B$ receptor 1a and 1b cDNA. The primer combination 839 and 918 produced a PCR product corresponding to the 5'-end of the $GABA_B$ receptor 1b cDNA.

The PCR products were subcloned into the pGEM-T vector from Promega (Madison, USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T, or primers complementary to the cDNA encoding the $GABA_B$ receptor, were used as primers for the sequencing reactions.

Additional PCR primers were designed based on the obtained sequences encoding fragments of the human $GABA_B$ receptor, additional DNA fragments encoding parts of the human $GABA_B$ receptors were amplified by PCR, and the PCR products were subcloned and sequenced as described above.

EXAMPLE 1B

Cloning and Sequencing of the 3'-ends of the cDNA Encoding Human $GABA_B$ Receptors 1a and 1b Messenger RNA from human hippocampus was obtained from Clontech (Palo Alto, Calif., USA) (catalogue #6578-1). First strand cDNA synthesis reactions were performed using the First-strand™ cDNA Synthesis kit from Amersham Pharmacia Biotech (Uppsala, Sweden). The Not I-$d(T)_{18}$ primer was used to prime the first-strand synthesis. The generated cDNA molecules were used as templates in the PCR reactions described below.

Specific PCR primers were designed (as shown in Table 2) based on the sequences of the human $GABA_B$ receptor 1a and 1b cDNA obtained in Example 1A and the EST sequence set forth in EMBL accession number Y11044.

By homology searches in the EMBL database using the $GABA_B$ receptor cDNA sequences obtained in Example 1A as the query sequences, the EST sequence set forth in EMBL accession number Y11044 has been found to be homologous to the 3'-end of the $GABA_B$ receptor cDNA.

TABLE 1

Primers used for RT-PCR on mRNA trom human hippocampus

| Nr. | Species | Sequence 5'–3' | SEQ ID NO |
|---|---|---|---|
| 794 | Rat | GTTTCTTCTCGGATCCAGCTGTGCCTG | 1 |
| 795 | Rat | CAGGCACAGCTGGATCCGAGAAGAAACT | 2 |
| 796 | Rat | CGGTCGACTCACTTGTAAAGCAAATGTACTCGACTCCC | 3 |
| 797 | Rat | ATGCGCGCCGGCAGCCAACATGCTGCTGCTGCTGGTGC | 4 |
| 831 | Rat | CGGTCGACTCACTTGTAAAGCAAATGTACTCGACTCCCATCACAGC | 5 |
| 838 | Rat | ATGCGCGCCGGCAGCCAACATGCTGCTGCTGCTGGTGCCTCTCTTCC | 6 |
| 842 | Rat | CAGGCACAGCTGGATCCGAGAAGAAACTCTGTCGGAAAGT | 7 |
| 863 | Rat | GGTCATCCAGCGTTGAGGTGAAGAC | 8 |
| 864 | Rat | GAAGGTTGCCAGATTATACATCCGC | 9 |
| 865 | Rat | CCACGATGATTCGAGCATCTTGACG | 10 |
| 866 | Rat | GCCTCTCACTCCCCTCATCTCC | 11 |
| 932 | Human | GAGTGAAGGAGGCTGGAATTG | 12 |

TABLE 2

Primers used in PCR to amplify 3'ends of human $GABA_B$ receptor cDNA

| Nr. | Species Species | Sequence 5'–3' | SEQ ID NO |
|---|---|---|---|
| 938 | Human | GACGCTTATCGAGCAGCTTC | 13 |
| 972 | Human | AGCCCAGAACTCACAGGGGGACAT | 14 |
| 973 | Human | GCTTCAAGCCAGGTACGAACTAA | 15 |

Various cDNA fragments encoding parts of the human $GABA_B$ receptors were amplified directly by PCR using the designed primers with the generated cDNA molecules as templates. All PCR experiments were carried out using Perkin Elmer Taq DNA polymerase with Gene Amp™ (Roche Molecular Systems Inc., NJ, USA) with the following PCR program: +95° C. for 1 minute, +50° C. for 30 seconds, +72° C. for 3 minutes, repeated 44 times, and then +72° C. for 7 minutes. The following combinations of primers gave PCR products with the expected sizes: 938 and 972, and 938 and 973, corresponding to the 3'-end of both $GABA_B$ receptor 1a and 1b cDNA.

The PCR products were subcloned into the pGEM-T™ vector from Piomega (Madison, USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™, or primers complementary to the cDNA encoding the $GABA_B$ receptor, were used as primers for the sequencing reactions.

EXAMPLE 1C

Cloning and Sequencing of the 5'-end of the cDNA Encoding Human $GABA_B$ Receptor 1b Messenger RNA from human hippocampus was obtained from Clontech (Palo Alto, Calif., USA) (catalogue #6578-1). A Marathon™ cDNA amplification kit (Clontech) was used for performing 5'/3'-RACE (Rapid Amplification of cDNA Ends). Adaptor-ligated double stranded cDNA molecules were amplified according to standard methods, as described by the manufacturer. A $pd(N)_6$ primer from the First-strand™ cDNA Synthesis kit from Amersham Pharmacia Biotech (Uppsala, Sweden) was used to produce the adaptor-ligated cDNA.

A specific PCR primer was designed (Table 3) based on the sequences of the human $GABA_B$ receptor 1b cDNA obtained in Example 1A.

TABLE 3

Primers used in PCR to amplify the 5'-ends of human $GABA_B$ receptor CDNA

| Nr. | Source | Sequence 5'–3' | SEQ ID NO |
|---|---|---|---|
| 958 | Human | TGGCCCTCCACCGCCTCAGTCATCTCA | 16 |
| AP1 | Marathon kit | CCATCCTAATACGACTCACTATAGGGC | 17 |

cDNA fragments encoding part of the human $GABA_B$ receptors were amplified directly by PCR using the designed primers with the generated adaptor-ligated cDNA molecules as templates. PCR was carried out using the Expand Long Template™ PCR System (Boehringer Mannheim GmbH, Germany) with the following PCR program: +94° C. for 1 minute, +94° C. for 30 seconds, +60° C. for 30 seconds, and +68° C. for 4 minutes, repeated 24 times. The primer combination AP1 and 958 produced a PCR product that corresponded to the 5'-end of the $GABA_B$ receptor 1b cDNA, including 190 base pairs upstream of the initiation codon.

The PCR products were subcloned into the pGEM-T™ vector from Promega (Madison, USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™, or primers complementary to the cDNA encoding the $GABA_B$ receptor, were used as primers for the sequencing reactions.

EXAMPLE 1D

Cloning and Sequencing of the 5'-end of the cDNA Encoding Human $GABA_B$ Receptor 1a Messenger RNA from human hippocampus was obtained from Clontech (Palo Alto, USA) (catalogue #6578-1). A Marathon™ cDNA amplification Kit (Clontech) was used to obtain adaptor-ligated double stranded cDNA molecules according to conventional methods as described by the manufacturer. The $pd(N)_6$ primer from the First-strand™ cDNA Synthesis kit from Amersham Pharmacia Biotech (Uppsala, Sweden) was used to obtain the adaptor-ligated cDNA.

Specific PCR primers were designed (as shown in Table 4) based on the sequences of the human $GABA_B$ receptor 1a cDNA obtained in Example 1 and the rat $GABA_B$ receptor 1a cDNA disclosed in WO 97/46675.

TABLE 4

Primers used to amplify the 5'-ends of the human $GABA_B$ receptor 1a cDNA

| Nr. | Species | Sequence 5'–3' | SEQ ID NO |
|---|---|---|---|
| 1033 | Human | CTCAATCTCATAGTCCACTGG | 18 |
| 1087 | Rat | CCTTGAGGCCCGGGGAGAG | 19 |

A cDNA fragment encoding part of the human $GABA_B$ 1a receptor was amplified directly by PCR using the designed primers with the generated adaptor-ligated cDNA molecules as templates. PCR was performed using Perkin Elmer Taq DNA polymerase with Gene AmP™ (Roche Molecular Systems Inc., NJ, USA) with the following PCR program: +94° C. for 1 minute, +50° C. for 30 seconds, +72° C. for 3 minutes, +94° C. for 1 minute, +60° C. for 30 seconds, and +72° C. for 4 minutes, repeated 34 times, and then +72° C. for 7 minutes.

The primer combination 1087 and 1033 produced a PCR product corresponding to the 5'-end of the $GABA_B$ receptor 1a cDNA, including 26 base pairs upstream of the initiation codon.

The PCR products were subcloned into the pGEM-T™ vector from Promega (Madison, USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™ were used as primers for the sequencing reactions.

Complete cDNA sequences encoding the human $GABA_B$ receptor 1a (SEQ ID NO: 48) and the human $GABA_B$ receptor 1b (SEQ ID NO: 50) were obtained by aligning the sequences of the different fragments cloned and sequenced in Examples 1A, 1B, 1C, and 1D.

EXAMPLE 2A

Cloning and Sequencing of cDNA Encoding Canine $GABA_B$ Receptor 1a

A QuickPrep Micro mRNA Purification™ kit (Amersham Pharmacia Biotech, Uppsala, Sweden) was used to isolate mRNA from canine neural tissue according to conventional methods, as described by the manufacturer. First-strand cDNA synthesis reactions were performed using the First-strand™ cDNA Synthesis kit from Amersham Pharmacia Biotech (Uppsala, Sweden). The Not-I-d$(T)_{18}$ bifunctional or pd$(N)_6$ primer was used to prime the first-strand synthesis. The generated cDNA molecules were used as templates in the PCR reactions described below.

Specific PCR primers (as shown in Table 5) were designed based on the sequences of the rat $GABA_B$ receptor 1a and 1b cDNA (Kaupmann et al., 1997, EMBL accession numbers Y10369 (SEQ ID NO: 44) and Y10370 (SEQ ID NO: 46)). Various cDNA fragments encoding parts of the canine $GABA_B$ receptor were amplified directly by PCR using the designed primers with the generated cDNA molecules as templates. All PCR experiments were carried out using the Perkin Elmer Taq DNA polymerase with Gene AmP™ (Roche Molecular Systems Inc., NJ, USA) with the following PCR program: +95° C. for 1 minute, +50° C. for 30 seconds, and +72° C. for 3 minutes, repeated 44 times, and then +72° C. for 7 minutes. The following primer combinations produced PCR products with the expected sizes: 842 and 838, 838 and 795, and 838 and 865, correspond to the 5'-part of the canine $GABA_B$ receptor Primer pairs 848 and 844, 848 and 831, 848 and 841, 840 and 841 produced PCR products which correspond to 3'-part of the canine $GABA_B$ receptor cDNA.

TABLE 5

Primers used for RT-PCR on mRNA from canine cortex

| Nr. | Species | Sequence 5'—3' | SEQ ID NO |
|---|---|---|---|
| 795 | Rat | CAGGCACAGCTGGATCCGAGAAGAAACT | 20 |
| 831 | Rat | CGGTCGACTCACTTGTAAAGCAAATGTACTCGACTCCCATCACAGC | 21 |
| 838 | Rat | ATGCGCGCCGGCAGCCAACATGCTGCTGCTGCTGCTGGTGCCTCTCTTCC | 22 |
| 840 | Rat | CGTCAAGATGCTCGAATCATCG | 23 |
| 841 | Rat | CAGGGGGCTCAGAGGGTCCC | 24 |
| 842 | Rat | CAGGCACAGCTGGATCCGAGAAGAAACTCTGTCGGAAAGT | 25 |
| 844 | Rat | CGGTCGACTCACTTGTAAAGCAAATGTACTCGACTCCCATCACAGCTAAG | 26 |
| 848 | Rat | ACTTTCCGACAGAGTTTCTTCTCGGATCCAGCTGTGCCTG | 27 |
| 865 | Rat | CCACGATGATTCGAGCATCTTGACG | 28 |

The PCR products were subcloned into the pGEM-T™ vector from Promega (Madison, USA). The inserts were sudjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™, or primers complementary to the cDNA encoding the $GABA_B$ receptor, were used as primers for the sequencing reactions.

EXAMPLE 2B

Cloning and Sequencing of the 3'- and 5'-ends of the cDNA Encoding Canine $GABA_B$ Receptor 1a A QuickPrep™ Micro mRNA Purification kit (Amersham Pharmacia Biotech, Uppsala, Sweden) was used to isolate mRNA from canine nerve tissue according to conventional methods, as described by the manufacturer. A Marathon™ cDNA amplification Kit (Clontech, Palo Alto, Calif., USA) was used for performing both 5'- and 3'-RACE. Two adaptor-ligated double stranded cDNA libraries were amplified according to conventional methods, as described by the manufacturer. A random primer (pd$(N)_6$) was used when amplifying the adaptor-ligated cDNA for the 5'-RACE, and the Marathon™ cDNA Synthesis primer (52-mer) was used when amplifying the adaptor ligated cDNA for the 3'-RACE.

Specific PCR primers were designed (as shown in Table 6) based on the sequence of canine $GABA_B$ receptor 1a cDNA obtained in Example 2A.

TABLE 6

Primers used in PCR to amplify the 5'- and 3'-ends of canine $GABA_B$ receptor 1a cDNA

| Nr. | Species | Sequence 5'—3' | SEQ ID NO |
|---|---|---|---|
| 936 | canine | CTACCGCGCAATGAACTCCTCGTC | 29 |
| 1076 | canine | CGAGGTGGCGTTGGGGGTCTGTGC | 30 |
| AP1 | Marathon kit | CCATCCTAATACGACTCACTATAGGGC | 31 |
| AP2 | Marathon kit | ACTCACTATAGGGCTCGAGCGGC | 32 |

Various cDNA fragments encoding parts of the canine $GABA_B$ receptor were amplified by PCR from the adaptor-ligated cDNA using the designed primers. A number of different PCR programs were tested to find conditions under which PCR products corresponding to $GABA_B$ receptor DNA were obtained.

The 5'-PCR experiments were carried out using the Expand Long Template™ PCR System (Boehringer Mannheim GmbH, Germany) with the following PCR program: +94° C. for 30 seconds, +72° C. for 3 minutes, repeated 4 times; +94° C. for 30 seconds, +70° C. for 3 minutes, repeated 4 times; and +94° C. for 30 seconds, +68° C. for 3 minutes, repeated 24 times. The primer combination AP2 and 1076 produced a PCR product that corresponded to the 5'-end of the $GABA_B$ receptor cDNA, including 114 base pairs upstream the initiation codon.

The 3'-PCR experiments were carried out using the Expand Long Template™ PCR System (Boehringer Mannheim GmbH, Germany) with the following PCR program:

+94° C. for 1 minute; +94° C. for 30 seconds, +60° C. for 30 seconds, and +68° C. for 4 minutes, repeated 29 times. The primer combination AP1 and 936 produced a PCR fragment that corresponded to the 3'-end of the $GABA_B$ receptor cDNA, including the poly(A) tail.

The PCR products were subcloned into the pGEM-T vector from Promega (Madison, USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T or primers complementary to $GABA_B$ receptor DNA were used as primers for sequencing reactions.

A complete cDNA sequence encoding the canine $GABA_B$ receptor 1a (SEQ ID NO: 52) was obtained by aligning the sequences of the various fragments obtained in Example 2A and Example 2B.

EXAMPLE 3A

Cloning of cDNA Encoding Human $GABA_B$ Receptor 1c and 1d from Jurkat Cells A guanidine isothiocyanate/CsCl purification method was used to isolate total RNA from Jurkat cells. The first-strand cDNA synthesis was performed using a First-strand™ cDNA Synthesis kit from Amersham Pharmacia Biotech (Uppsala, Sweden). The $pd(N)_6$ primer was used to prime the first strand synthesis. The generated cDNA molecules were used as templates in the PCR reaction described below.

Specific PCR primers (as shown in Table 7) were designed based on the sequences of human $GABA_B$ receptor 1a and 1b cDNAs (Example 1), rat $GABA_B$ receptor (Kaupmann et al. 1997) and the EST sequence set forth in EMBL accession number Y11044.

TABLE 7

Primers used in RT-PCR on mRNA from Jurkat cells

| Nr | Species | Sequence 5'-3' | SEQ ID NO |
|---|---|---|---|
| 938 | human | GACGCTTATCGAGCAGCTTC | 33 |
| 972 | human | AGCCCAGAACTCACAGGGGGACAT | 34 |
| 973 | human | GCTTCAAGCCAGGTACGAACTAA | 35 |
| 893 | rat | GGAGCACCCCCAAGCCCCACTG | 36 |
| 937 | human | CTGGTTCCTCCCAATGTG | 37 |
| 1005 | rat | CCTCTCACTCCCCTCATCTC | 38 |
| 1030 | human | AAGCCAACCTTCCCTGCTTCTC | 39 |

Various cDNA fragments encoding parts of the $GABA_B$ receptor were amplified directly by PCR using human- and rat-specific primers. All PCR experiments were carried out using Perkin Elmer Taq DNA polymerase with Gene Amp™ (Roche Molecular Systems Inc., NJ, USA) with the following PCR program: +95° C. for 1 minute; +54° C. for 1 minute, and +72° C. for 3 minutes, repeated 44 times; and then +72° C. for 7 minutes.

The PCR products were subcloned into the pGEM-T™ vector from Promega (Madison, USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™ or primers complementary to $GABA_B$ receptor DNA were used as primers for the sequencing reactions.

The following primer combination produced PCR products corresponding to the 3'-end of the $GABA_B$ receptor cDNA: primer pairs 938 and 972; and 938 and 973. Unexpectedly, both of these fragments lacked 149 base pairs, resulting in a frame shift and the insertion of a new termination codon. The following primer combination produced a PCR product corresponding to the 5'-part of the $GABA_B$ receptor 1a cDNA: 893 and 937. The primer pairs 1005 and 937, and 1030 and 937 produced PCR products corresponding to the 5'-part of the $GABA_B$ receptor 1b cDNA. These PCR fragments lacked the same 149 base pairs that resulted in a frame shift and the insertion of a new termination codon.

These results show that Jurkat cells contain mRNA encoding two new forms of the human $GABA_B$ receptor. These new forms are designated $GABA_B$ receptor 1c (SEQ ID NO: 54 and 55) (with the mRNA including the same 5'-part as the $GABA_B$ receptor 1a) and $GABA_B$ receptor 1d (SEQ ID NO: 56 and 57) (with the mRNA including the same 5'-part as the $GABA_B$ receptor 1b). These two forms of the $GABA_B$ receptor do not contain any of the transmembrane region of the receptor and are therefore expected to be soluble forms of the receptor.

EXAMPLE 3B

Analysis of cDNA Encoding Human $GABA_B$ Receptors from Hippocampus

Messenger RNA from human hippocampus was obtained from Clontech (Palo Alto, USA) (catalogue #6578-1). First strand cDNA synthesis reactions were performed using the First-strand™ cDNA Synthesis kit from Amersham Pharmacia Biotech (Uppsala, Sweden). The $pd(N)_6$ primer was used to prime the first-strand synthesis. The generated cDNA molecules were used as templates in the PCR reactions described below.

Specific PCR primers were designed (as shown in Table 8) based on the sequences of the cDNAs encoding human $GABA_B$ receptors 1a and 1b.

TABLE 8

Primers used for RT-PCR on mRNA from human hippocampus

| Nr. | Species | Sequence 5'-3' | SEQ ID NO |
|---|---|---|---|
| 937 | Human | CTGGTTCCTCCCAATGTG | 40 |
| 938 | Human | GACGCTTATCGAGCAGCTTC | 41 |

cDNA fragments encoding parts of the human $GABA_B$ receptors were amplified directly by PCR using the designed primers with the generated cDNA molecules as templates. All PCR experiments were carried out using Perkin Elmer Taq DNA polymerase with Gene Amp™ (Roche Molecular Systems Inc., NJ, USA) with the following PCR program: +94° C. for 1 minute, +50° C. for 30 seconds, +72° C. for 3 minutes; +94° C. for 1 minute, +54° C. for 30 seconds, and +72° C. for 3 minutes, repeated 44 times; and then +72° C. for 7 minutes. The primer combination of 938 and 937 produced PCR products that corresponded to the expected size of the $GABA_B$ receptor 1a and 1b cDNAs, and to a fragment of a smaller size.

The PCR products were subcloned into the pGEM-T vector from Promega (Madison, USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™ or primers complementary to the cDNA encoding the $GABA_B$ receptor were used as primers for the sequencing reactions.

The larger PCR fragment was found to correspond to the 3'-part of the $GABA_B$ receptor 1a and 1b cDNA, and the smaller fragment which lacked 149 base pairs was found to correspond to the 3'-part of the $GABA_B$ receptors 1c and 1d cDNA identified in Example 3A.

EXAMPLE 4

Cloning and Sequencing of cDNA Encoding Canine $GABA_B$ Receptor 1b

A cDNA encoding the canine $GABA_B$ receptor 1b can be isolated in a manner similar to that described in Example 2 for receptor 1a. PCR primers specifically designed to be complementary to the 5'-end of the cDNA encoding the rat and human $GABA_B$ receptor 1b, together with PCR primers complementary to the 3'-end of the cDNA encoding the canine $GABA_B$ receptor 1a, and mRNA prepared from a suitable canine tissue, can be used.

EXAMPLE 5

Cloning of cDNA Encoding Canine $GABA_B$ Receptor 1c

Total RNA from canine liver was prepared using RNeasy™ Total RNA Purification Protocols (Qiagen GmbH, Germany). The first-strand cDNA synthesis was performed using a First-strand™ cDNA Synthesis kit from (Amersham Pharmacia Biotech, Uppsala, Sweden). The $pd(N)_6$ primer was used to prime the first-strand synthesis. The generated cDNA molecules were used as templates in the PCR reaction described below.

Specific PCR primers (as shown in Table 9) were designed based on the sequence of canine $GABA_B$ receptor 1a cDNA.

TABLE 9

Primers used in RT-PCR

| Nr. | Species | Sequence 5'–3' | SEQ ID NO |
|---|---|---|---|
| 936 | canine | CTACCGCGCAATGAACTCCTCGTC | 42 |
| 954 | canine | CCTTCTTCTCCTCCTTCTTAGTGA | 43 |

cDNA fragments encoding part of the canine $GABA_B$ receptor were amplified directly by PCR using canine specific primers. All PCR reactions were carried out using Perkin Elmer Taq DNA polymerase with Gene AmP™ (Roche Molecular Systems Inc., NJ, USA) with the following PCR program: +95° C. for 1 minute, +54° C. for 30 seconds, and +72° C. for 3 minutes, repeated 44 times, and then +72° C. for 7 minutes. The primer combination produced PCR products having a size corresponding to the $GABA_B$ receptor 1a cDNA and a fragment of a smaller size, indicating the presence of $GABA_B$ receptor 1c cDNA.

The PCR products were subcloned into the pGEM-T™ vector from Promega (Madison, Wis.; USA). The inserts were subjected to nucleotide sequence analysis, and the complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™ were used as primers for the sequencing reactions.

The smaller fragment was shown to have a deletion of 149 base pairs. This deletion caused a frame shift and insertion of a new termination codon, verifying the existence of a canine $GABA_B$ receptor 1c.

A complete cDNA sequence encoding the canine $GABA_B$ receptor 1c (SEQ ID NO: 58) was obtained by aligning the sequences of the fragments obtained in Example 2A, Example 2B and Example 5.

EXAMPLE 6

Cloning, Sequencing, and Organization of Human $GABA_B$ Receptor Genomic Fragments To determine the structural organization and sequence of the human $GABA_B$ receptor gene, human genomic DNA libraries and human genomic DNA were screened and analyzed. Human genomic libraries were obtained from Clontech (Palo Alto, Calif., USA). The libraries were constructed from female leukocyte DNA (catalog # HL1111J) cloned into a λEMBL-3 vector. The average size of the inserts was 16 kb, and the number of independent clones was $1.7\times10^6$ Human genomic DNA was obtained from Clontech (catalog #6550-1). In order to isolate recombinant phage containing exon and intron sequences of the human $GABA_B$ receptor gene, 48 individual bacterial plates, each having a diameter of 150 mm and approximately $4\times10^4$ individual plaques, were screened. Conventional methods and solutions were used, as described in The *Library Protocol Handbook: General Procedures for the Hybridization of Lambda Phage Libraries w/DNA Probes* (Clontech) with modifications as described below.

The experiment was carried out essentially as follows, and the following numbers are given on a per plate basis. A sample of the phage library, diluted in 0.1 ml sterile lambda diluent, was prepared to obtain an estimated titer of 40,000 pfu (plaque forming units). A 0.6 ml culture of the *E. coli* host strain K802 (obtained from Clontech) in LB-medium was infected with 40,000 pfu recombinant phage for 15 minutes at +37° C. The culture then was mixed with 7 ml top agarose (6.5 g of agarose added per liter of LB) and poured onto LB plates. The plates were incubated at +37° C. for approximately 7 hours. The plates were then chilled at +4° C.

Plaque hybridization experiments were carried out as follows. Membrane filters (Colony/Plaque Screen (DuPont, Wilmington, Del., USA)) were placed on top of the plates for 3 minutes. For denaturation of DNA, the filters were removed and floated in 0.5 M NaOH on plastic wrap for 2 minutes, with the plaque side up. This step was repeated to ensure efficient denaturation. Following neutralization, the membrane filters were placed in 1M Tris-HCl, pH 7.5, twice for 2 minutes, and allowed to dry.

Probes for screening of the membrane filters by DNA hybridization were obtained as follows. A $GABA_B$ receptor cDNA clone was digested with SacII to release a 479 bp fragment (base pairs 573–1051 of the cDNA encoding human $GABA_B$ receptor 1a, SEQ ID NO: 48). This 479 bp fragment was separated from the remaining $GABA_B$ receptor cDNA by electrophoresis on an agarose gel. A segment of the gel containing the 479 bp fragment was excised and transferred to a polypropylene microcentrifuge tube. Water was then added to the microcentrifuge tube at a ratio of 3 ml per gram of gel. The microcentrifuge tube then was placed in a boiling water bath for 7 minutes to melt the agarose gel and denature the DNA.

DNA (25 ng) contained within the melted agarose was labeled with 32p using a Megaprime™ DNA labeling system (Amersham Pharmacia Biotech, Uppsala, Sweden) according to the supplier's instructions. Unincorporated $^{32}$P-labeled nucleotides were removed from the DNA sample with a MicroSpin™ G-50 Column (Amersham Pharmacia Biotech, Uppsala, Sweden). Additional probes were prepared by PCR amplification of various regions of the GABA$_B$ receptor cDNA (base pairs 68–486 and 2368–2863 of the cDNA encoding human GABA$_B$ receptor 1a, SEQ ID NO: 48). These probes also were labeled with $^{32}$P and purified as described above.

The DNA hybridization reaction was performed under stringent conditions according to the method described below. The filter membranes were prehybridized at +65° C. for at least 1 hour in a solution of 1% SDS, 1M NaCl, and 10% dextran sulfate using a hybridization oven (Hybaid Ltd, Ashford, UK). Following prehybridization, a solution containing denatured herring sperm DNA at a final concentration of 100 μg/ml and the $^{32}$P-labeled DNA probe at a concentration <10 ng/ml (for optimal signal to background ratio) was added to the prehybridization solution, and the membrane filters were incubated at +65° C. for 10–20 hours. Following the removal of the hybridization solution, the membrane filters were washed in a solution of 2×SSC (0.3 M NaCl, 0.03 M Na-citrate), 1% SDS twice for 5 minutes at room temperature. The membrane filters then were washed twice more in the same solution, incubating at +60° C. for 30 minutes each wash. The filters then were washed twice at room temperature in 0.1×SSC. Finally, the membrane filters were placed on a sheet of filter paper with the DNA face up, and allowed to dry. The dried membrane filters were then exposed to X-ray films and autoradiographed.

Of the approximately $2\times10^6$ individual plaques analyzed, four hybridizing plaques were detected and isolated. These four isolates were designated #GR1, #GR12, #GR13 and #GR41, respectively. After several rescreening experiments, the recombinant phage DNA was purified using a Qiagen Lambda Midi™ Kit (Qiagen GmbH, Germany). The purified DNA was digested with SalI, and the fragments representing the inserts were isolated by agarose electrophoresis.

The approximate sizes of the inserts were: for isolate #GR1, 12 kb; for isolate #GR12, 12 kb; for isolate #GR13, 16 kb; and for isolate #GR41, 19 kb. These fragments were cloned into SalI digested linearized pUC19, resulting in the plasmids pAM362 (isolate #GR1), pAM363 (isolate #GR12), pAM364 (isolate #GR13), and pAM365 (isolate #GR41). The inserts from the four plaques that hybridized to GABA$_B$ receptor cDNA probes were analyzed by PCR, restriction mapping, and hybridization to $^{32}$P-labeled DNA fragments representing various regions of the GABA$_B$ receptor gene.

The cloned fragments in the plasmids pAM362, pAM363, pAM364, and pAM365 were characterized by restriction enzyme mapping, using EcoRI, HindIII, PstI, and BamHI. The approximate positions of the exons, and the approximate sizes of the introns, were analyzed and determined by PCR-based exon-exon linking and agarose gel electrophoresis.

To facilitate nucleotide sequence analysis, seven restriction sub-fragments derived from pAM364, two restriction fragments derived from pAM362, and one restriction sub-fragment derived from pAM365 were isolated and cloned into pUC19, resulting in the plasmids pAM366–pAM375. To this end, PCR primers located within the pUC19 sequence either upstream or downstream of the cloning site were combined with a PCR primer having a defined orientation and specific for the GABA$_B$ receptors derived subcloned fragment.

The inserts in the 10 plasmids pAM366–pAM375 were subjected to nucleotide sequence analysis. The nucleotide sequences for all subclones were determined using a Thermo Sequenase™ dye terminator cycle sequencing pre-mix kit (Amersham Pharmacia Biotech, Uppsala, Sweden). Specific oligonucleotides complementary to pUC19 or primers complementary to the GABA$_B$ receptor cDNA were used as primers for the sequencing reactions.

The genomic fragments cloned in the plasmids pAM362–pAM365 contain the complete transcribed part of the human GABA$_B$ receptor gene and extend more than 3 kb upstream of the first exon and more than 2 kb downstream of the last exon. The fragment cloned in the plasmid pAM362 contains exons 7–11; pAM363 contains exons 12–22; pAM364 contains exons 1–11; and pAM365 contains exons 12–23 of the GABA$_B$ receptor gene (FIG. 1). The sequences of exons 1–11 and introns 1–10 are set forth in SEQ ID NO: 60, and the sequences of exons 12–23 and introns 12–22 are set forth in SEQ ID NO: 61.

The human GABA$_B$ receptor gene consists of 23 exons and 22 introns (FIG. 1). The exons range in size from 21 bp to 1486 bp. As indicated in Table 10, the exon/intron boundaries are in accordance with the AG/GT rule and conform well to the consensus sequence suggested by Mount et al. 1982.

TABLE 10

Exon-Intron boundaries of the GABA$_B$ receptor gene, sequences at exon-intron junctions.

| | 5' splice donor....................3' splice acceptor |
|---|---|
| Exon 1-Exon 2 | **CGAG** GTAAGAG.............CCGCCTCTCACTTA **ATGT**<br>G |
| Exon 2-Exon 3 | **GAAG** GTGCATC.............CGACTCACCCCTTA **GTTG**<br>G |
| Exon 3-Exon 4 | **TGTG** GTGAGTA............ CCWATCTCTCCACA **TCCG**<br>G |
| Exon 4-Exon 5 | **CAGG** GTGAGGG.............CTTTCCTGCTGCCA **TGAA**<br>G |
| Exon 5-Exon 6 | **TCAG** GTGAGAT.............CGCACCCCTCCTCA **AACG**<br>G |
| Exon 6-Exon 7 | **CAAG** GTAGCCC.............CCTCTTGTCTTTCA **TGTG**<br>G |

TABLE 10-continued

Exon-Intron boundaries of the $GABA_B$ receptor gene, sequences at exon-intron junctions.

| | 5' splice donor...................3' splice acceptor |
|---|---|
| Exon 7-Exon 8 | **TGTG** GTAAGCA.............CTCCCTGCCCCACA **CTTT** G |
| Exon 8-Exon 9 | **TTCG** GTGAGGA.............TTATTCCCACCCAA **ACTC** G |
| Exon 9-Exon 10 | **GAAG** GTCAGAT.............CTTTCTCTGTKGTA **CGCC** G |
| Exon10-Exon 11 | **TGAG** GTGGART.............CTCCTCTGTATTCA **GTGT** G |
| Exon11-Exon 12 | **CATG** GTGAGAG.............TTTTTTCCTCCCAA **ACAT** G |
| Exon12-Exon 13 | **CTCT** GTGAGTT.............TGTTCCTTCCCTCA **GGCC** G |
| Exon13-Exon 14 | **CAGG** GTTAGTA.............TTGTCGTCTGCCCA **GTGG** G |
| Exon14-Exon 15 | **ATTG** GTGAGTG.............CCCTGTGCCATGCA **GAGG** G |
| Exon15-Exon 16 | **TCCG** GTXAGTT.............CCACCTCTGCCCTA **TTAT** G |
| Exon16-Exon 17 | **CCAG** GTGAGGA.............TCTCTTCCTTTCTA **GCCC** G |
| Exon17-Exon 18 | **GAAG** GTGAGCT.............CACATATTTATCCA **ACTC** G |
| Exon18-Exon 19 | **TGAG** GTACCAC.............TYGTTTCTGCCCTA **ACAT** G |
| Exon19-Exon 20 | **CTTG** GTGTGTC.............CTCCTGCCATCCTA **GCAT** G |
| Exon20-Exon 21 | **GGCA** GTGAGCA.............TGTCTTTCCCTCTA **GTCC** G |
| Exon21-Exon 22 | **CAAG** GTAAGGA.............AACATTTGCCCCCA **ATGC** G |
| Exon22-Exon 23 | **TGAG** GTGCGGG.............TGCTTCTTCCTCCA **AAAG** G |

A comparison of the sequences of the different forms of the human $GABA_B$ receptor cDNA (SEQ ID NOS: 48, 50, 54, and 56) with the sequence of the human $GABA_B$ gene (SEQ ID NOS: 60 and 61) reveals that various mRNAs encoding human $GABA_B$ receptors are formed by alternative splicing. The translational start site of the $GABA_B$ receptor 1a is in exon 2 and the translational stop signal is in exon 23. The mRNA encoding $GABA_B$ receptor 1b is formed by alternative splicing such that part of intron 5 is retained together with exon 6, and the translational start of the $GABA_B$ receptor 1b is derived from the intron sequence. The mRNA encoding $GABA_B$ receptor 1c is formed by alternative splicing such that exon 15 is removed along with introns 14 and 15, and a frame shift and a translational stop signal are generated in the sequence corresponding to exon 16. The mRNA encoding $GABA_B$ receptor 1d is formed when the translational start of the $GABA_B$ receptor 1b is generated together with the translational stop of the $GABA_B$ receptor 1c.

The $GABA_B$ receptor 1a isoform is formed by splicing exon 5 to a cryptic splice site in the middle of exon 6. Transcription of the $GABA_B$ receptor 1b isoform mRNA is most likely initiated from regulatory elements in intron 5. The ATG that initiates translation of $GABA_B$ receptor 1b mRNA is located in the 5'-end of exon 6.

Additional mRNA variants encoding variants of the human $GABA_B$ receptor can be derived by alternative splicing such that one or more of the exons, or parts of exons, are excised in the processing of the pre-mRNA. Subsequent translation of these mRNAs gives rise to variants of the human $GABA_B$ receptor having potentially different biological and/or pharmacological activities.

EXAMPLE 7

Analysis of cDNA Encoding Human $GABA_B$ Receptors from Human Brain

Messenger RNA from human fetal brain (catalog #6525-1) and adult human brain (catalog #6516-1) were obtained from Clontech (Palo Alto, Calif., USA). First strand cDNA synthesis reactions were performed using a First Strand™ cDNA Synthesis kit from Amersham Pharmacia Biotech (Uppsala, Sweden). The $pd(N)_6$ primer was used to prime the first-strand synthesis. The generated cDNA molecules were used as templates in the PCR reactions described below.

Specific PCR primers were designed (as shown in Table 11) based on the sequences of the rat $GABA_B$ receptor 1a and 1b cDNA and human $GABA_B$ receptor 1a and 1b cDNA. Various cDNA fragments encoding parts of the human $GABA_B$ receptors were amplified directly by PCR using the designed primers with the generated cDNA molecules as templates. PCR experiments with primers 838, 863, 864, and 865 were carried out using Perkin Elmer Taq DNA polymerase with Gene AmP™ (Roche Molecular System Inc., NJ, USA) with the following PCR program: +95° C. for 1 minute, +50° C. for 30 seconds, and +72° C. for 3 minutes, repeated 44 times, and then +72° C. for 7 minutes. PCR experiments with primers 937 and 1015 were carried out using the Expand Long Template™ PCR System (Boehringer Mannheim GmbH, Germany) with the following PCR program: +94° C. for 2 minutes, +94° C. for 10 seconds, +55° C. for 30 seconds, and +68° C. for 3 minutes, repeated 35 times, and then +68° C. for 7 minutes. The primer combinations 838 and 863, 864 and 863, 864 and 865, and 937 and 1015 produced the expected PCR products.

TABLE 11

Primers used for RT-PCR on mRNA from human fetal brain

| Nr. | Species | Sequence 5'—3' | SEQ ID NO |
|---|---|---|---|
| 838 | Rat | ATGCGCGCCGGCAGCCAACATGCTGCTGCTGCTGCTGGTGCCTCTCTTCC | 62 |
| 863 | Rat | GGTCATCCAGCGTTGAGGTGAAGAC | 63 |
| 864 | Rat | GAAGGTTGCCAGATTATACATCCGC | 64 |
| 865 | Rat | CCACGATGATTCGAGCATCTTGACG | 65 |
| 937 | Human | CTGGTTCCTCCCAATGTG | 66 |
| 1015 | Human | CCAGTGGACTATGAGATTGAG | 67 |

The PCR products were subcloned into the pGEM-T™ vector from Promega (Madison, Wis., USA), and the inserts were subjected to nucleotide sequence analysis. The complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T™ or primers complementary to the cDNA encoding the $GABA_B$ receptor were used as primers for the sequencing reactions.

A number of analyzed clones isolated from fetal brain lacked 186 base pairs corresponding to exon 4. Such alternative splicing resulted in a cDNA (SEQ ID NO: 70) encoding a protein (SEQ ID NO: 71) containing 899 amino acids, and designated $GABA_B$ receptor 1e.

Other clones from fetal brain lacked 368 base pairs, corresponding to exons 4, 5, and 6, and resulting in a cDNA (SEQ ID NO: 72) having a frame shift and a translational stop codon generated in the sequence corresponding to exon 7. This cDNA encoded a protein (SEQ ID NO: 73) that included only 97 amino acids, which was designated $GABA_B$ receptor 1f.

One clone lacked 207 base pairs, corresponding to exons 4 and 5, and resulting in a cDNA (SEQ ID NO: 74) encoding a protein (SEQ ID NO: 75) containing 892 amino acids and designated $GABA_B$ receptor 1g.

Another clone had two deletions: the first deleted 186 base pairs corresponding to exon 4, and the second deleted 39 base pairs corresponding to part of exon 6. The resulting cDNA (SEQ ID NO: 76) encoded a protein (SEQ ID NO: 77) containing 886 amino acids, designated $GABA_B$ receptor 1h.

Another clone from adult human brain had a deletion of 1194 base pairs corresponding to base pairs 319–1512 of the cDNA encoding human $GABA_B$ receptor 1a. This deletion corresponds to part of exon 4, exons 5–11, and part of exon 12. This cDNA (SEQ ID NO: 78) encodes a protein (SEQ ID NO: 79) containing 563 amino acids, designated $GABA_B$ receptor 1i.

One clone isolated from fetal brain lacked 284 base pairs corresponding to part of exon 3 and all of exon 4, generating a frame shift and a translational stop codon in the sequence corresponding to exon 5. This cDNA (SEQ ID NO: 80) encodes a protein (SEQ ID NO: 81) containing only 105 amino acids, designated $GABA_B$ receptor 1j.

EXAMPLE 8

Analysis of cDNA Encoding Human $GABA_B$ Receptors from Jurkat Cells

A guanidine isothiocyanate/CsCl method was used to isolate total RNA from Jurkat cells. First strand cDNA synthesis reactions were performed using the First Strand™ cDNA Synthesis kit from Amersham Pharmacia Biotech (Uppsala, Sweden). The $pd(N)_6$ primer was used to prime the first-strand synthesis. The generated cDNA molecules were used as templates in the PCR reactions described below.

Specific PCR primers were designed (as shown in Table 12) based on the sequences of the human $GABA_B$ receptor 1a and 1b cDNA.

TABLE 12

Primers used for RT-PCR on mRNA from Jurkat cells

| Nr. | | Sequence 5'—3' | SEQ ID NO |
|---|---|---|---|
| 937 | Human | CTGGTTCCTCCCAATGTG | 68 |
| 1015 | Human | CCAGTGGACTATGAGATTGAG | 69 |

cDNA fragments encoding parts of the human $GABA_B$ receptors were amplified directly by PCR using the designed primers with the generated cDNA molecules as templates. PCR was carried out using the Expand Long Template™ PCR System (Boehringer Mannheim GmbH, Germany) with the following PCR program: +94° C. for 2 minutes; +94° C. for 10 seconds, +55° C. for 30 seconds, and +68° C. for 3 minutes, repeated 35 times; and then +68° C. for 7 minutes. The primer combination 937 and 1015 produced a PCR product.

The PCR products were subcloned into the PGEM-T vector from Promega (Madison, Wis., USA), and the inserts were subjected to nucleotide sequence analysis. The complete nucleotide sequences for all subclones were determined using a Thermo Sequenase™ dye terminator cycle sequencing pre-mix kit (Amersham Pharmacia Biotech, Uppsala, Sweden). Specific oligonucleotides complementary to the vector pGEM-T or primers complementary to the cDNA encoding the $GABA_B$ receptor were used as primers for the sequencing reactions.

Two clones had two deletions: the first deleted 368 base pairs corresponding to exons 4, 5, and 6; the second deleted 151 base pairs corresponding to exon 15, with a frame shift and a translational stop codon generated in the sequence corresponding to exon 7. This cDNA (SEQ ID NO: 82) encodes a protein (SEQ ID NO: 83) containing only 98 amino acids, which is designated $GABA_B$ receptor 1k, and which is identical to the $GABA_B$ receptor 1f described above.

Two other clones also had two deletions: the first a deletion of 246 base pairs corresponding to part of exon 4, exon 5, and exon 6; the second deletion lacked 149 base pairs corresponding to exon 15, generating a frame shift and a translational stop codon in the sequence corresponding to exon 16. This cDNA (SEQ ID NO: 84) encodes a protein (SEQ ID NO: 5) containing 496 amino acids, which is designated $GABA_B$ receptor 11.

Additional variants of cDNAs encoding the human $GABA_B$ receptors can be identified in a similar manner using PCR primers based on the sequences of the cDNAs and genomic fragments encoding the human $GABA_B$ receptors disclosed herein.

The biological activity of these variants of the human $GABA_B$ receptor can be evaluated by transfection of suitable host cells with expression vectors containing the corresponding cDNA sequences, and measuring binding of labeled ligands activation of the receptor, or modulation of receptor function.

EXAMPLE 9

Generation of Antibodies

Antibodies were raised in rabbits against four different BSA-conjugated 20 amino acid-long synthetic peptides corresponding to selected regions of the human and canine $GABA_B$ receptor extracellular domains. Two polyclonal antibodies were directed against a sequence common to $GABA_B$ receptors 1a and b (ab1 and ab2), one against a $GABA_B$ receptor 1a-specific region (a1), and one against a $GABA_B$ receptor 1b-specific sequence (b1). To allow BSA-conjugation, a cysteine residue was added to the amino terminus in all peptides except a1, which contains an endogenous cysteine. The peptide sequences are as follows:

Peptide a1: (amino acids 18–37 of SEQ ID NO: 49) $NH_2$-Gly Gly Ala Gln Thr Pro Asn Ala Thr Ser Glu Gly Cys Gln Ile Ile His Pro Pro Trp-COOH Peptide ab1: (amino acids 197–216 of SEQ ID NO: 49, with N-terminally added Cys) $NH_2$-Cys Glu Asp Val Asn Ser Arg Arg Asp Ile Leu Pro Asp Tyr Glu Leu Lys Leu Ile His His-COOH Peptide ab2: (amino acids 271–290 of SEQ ID NO: 49, with N-terminally added Cys) $NH_2$-Cys Ser Pro Ala Leu Ser Asn Arg Gln Arg Phe Pro Thr Phe Phe Arg Thr His Pro Ser Ala-COOH Peptide b1: (amino acids 30–47 of SEQ ID NO: 57, with N-terminally added Cys) $NH_2$-Cys Ser His Ser Pro His Leu Pro Arg Pro His Ser Arg Val Pro Pro His Pro Ser-COOH The antibodies were purified from rabbit serum by affinity chromatography using the corresponding immobilized peptide. The antibodies subsequently were used to detect expression of recombinant $GABA_B$ receptor isoforms on Western blots.

EXAMPLE 10

Heterologous Expression of $GABA_B$ Receptor Isoforms in Mammalian Cells

Figure 2:
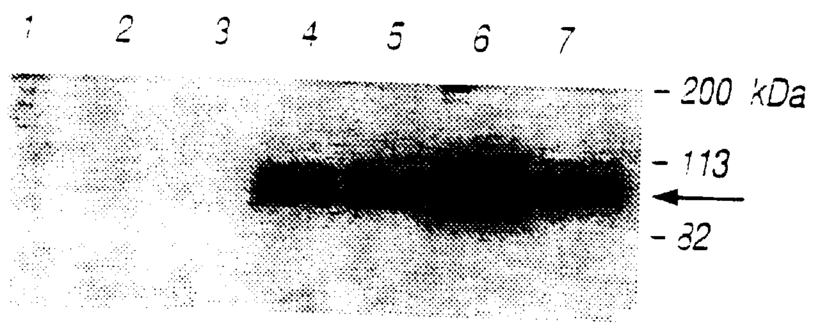
FIG. 2 is a Western blot illustrating expression of the human $GABA_B$ receptor 1b isoform in transfected C127 cells. A polyclonal anti-human $GABA_B$ receptor antibody was used. Lane 1: Untransfected C127 whole cell lysate. Lanes 2–7: Whole cell lysates of six independent clones transfected with cDNA encoding the human $GABA_B$ receptor 1b isoform. The clones analyzed in lanes 4 to 7 express a $GABA_B$ receptor of the expected molecular weight (arrow)

A HindIII/SalI cDNA fragment encoding the human $GABA_B$ receptor 1b isoform was cloned into a BPV (bovine papilloma virus)-based expression vector containing the mMT-1 (murine metallothionein) promoter. Using a calcium phosphate transfection method, murine C127 cells were co-transfected with the $GABA_B$ receptor expression construct and an expression plasmid containing a G418 resistance marker gene. G418 resistant clones were evaluated by Western blot analysis for expression of the approximately 100 kDa $GABA_B$ receptor 1b isoform (FIG. 2). The human $GABA_B$ receptor 1b isoform also was expressed in human HEK-293 cells using a pCI-neo expression vector and Lipofectamine™ (Life Technologies, Inc., Rockville, Md., USA) for transfection. The identity of the heterologously expressed receptor was verified in HEK-293 cells by Western blot analysis and radioligand binding experiments.

Figure 3:
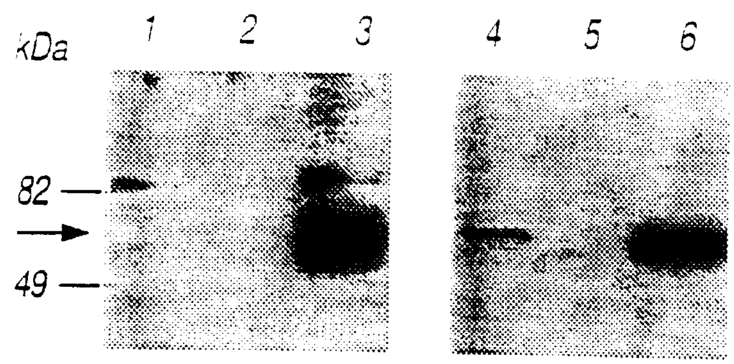
FIG. 3 is a Western blot illustrating expression of the human $GABA_B$ receptor 1d isoform in transfected C127 cells. A polyclonal anti-human $GABA_B$ receptor antibody was used. Lanes 1–3: Concentrated culture media from three independent C127 clones transfected with a cDNA expression construct encoding the human $GABA_B$ receptor 1d isoform. Lanes 4–6: Whole cell lysates corresponding to the clones analyzed in lanes 1–3. The figure shows that the human $GABA_B$ receptor 1d cDNA encodes a secreted isoform. The arrow indicates the bands corresponding to the 1d isoform.

A cDNA fragment encoding the human $GABA_B$ receptor 1d isoform was cloned into a BPV-based expression vector containing the mMT-1 promoter. Using a calcium phosphate transfection method, murine C127 cells were co-transfected with the $GABA_B$ receptor expression construct and an expression plasmid containing a G418 resistance marker gene. G418 resistant clones, and concentrated medium from such clones, were evaluated for $GABA_B$ receptor 1d isoform expression by Western blot analysis (FIG. 3). This experiment revealed that the human $GABA_B$ receptor 1d is a secreted isoform.

EXAMPLE 11

Heterologous Expression of $GABA_B$ Receptor Isoforms in *E. coli*

Figure 4:
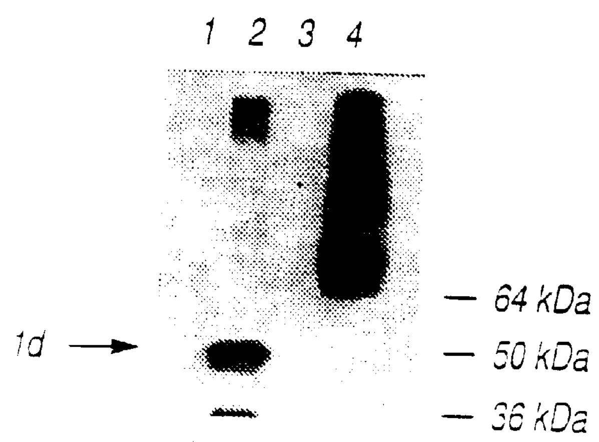
FIG. 4 is a Western blot illustrating expression of the human $GABA_B$ receptor 1d isoform in *E. coli*. A polyclonal anti-human $GABA_B$ receptor antibody was used. Lane 1: Lysate from an uninduced *E. coli* culture transformed with an pET-based expression construct encoding the human $GABA_B$ receptor 1d cDNA. Lane 2: Lysate from an IPTG-induced *E. coli* culture transformed with an expression construct encoding the human $GABA_B$ receptor 1d cDNA.

A cDNA fragment encoding the human $GABA_B$ receptor 1d isoform was cloned into a modified pET (Pharmacia Amersham, Uppsala, Sweden) vector downstream of a STII (heat stable enterotoxin II of *E. coli*) signal peptide. The cDNA insert was followed by a thrombin cleavage site and a hexahistidine tag. The expression construct was subsequently used to transform the BL21 (DE3) *E. coli* strain BL21 (DE3). Western blot analysis of IPTG-induced bacteria revealed expression of a human $GABA_B$ receptor 1d isoform of the expected size (FIG. 4).

In addition, the human $GABA_B$ receptor 1d isoform was successfully expressed in *E. coli* strain AD494 (DE3) without fusion to a bacterial signal peptide.

EXAMPLE 12

Method for the Screening of Substances which are $GABA_B$ Receptor Antagonists or Agonists $GABA_B$ receptor expressing cells, and transgenic animals or cells and tissues derived therefrom, are used to screen substance libraries for antagonist or agonist activities. Screening can be performed as ligand binding assays or functional assays. For screening, cells and tissues are prepared in various ways, each uniquely suited to its purpose. Ligand binding assays are performed in vivo or in vitro. Functional assays exemplified by, but not limited to, $Ca^{++}$-responses, cAMP-responses and effects on $Cl^-$ and $K^+$ channels, are performed in living cells, broken cells, or isolated cell membranes, as well as in tissues and in living animals.

What is claimed is:

1. An isolated nucleic acid molecule encoding a GABA receptor, said nucleic acid molecule comprising a nucleotide sequence set forth as SEQ ID NO:48.

2. The nucleic acid molecule of claim 1, wherein said nucleic acid molecule is DNA.

3. The nucleic acid molecule of claim 1, said nucleic acid molecule consisting of a nucleotide sequence set forth as SEQ ID NO:48.

4. A vector comprising the nucleic acid molecule of claim 1.

5. A cultured host cell harboring a vector according to claim 4.

6. The cell of claim 5, wherein the cell expresses the nucleic acid molecule.

7. A process for the production of a GABA receptor polypeptide, said process comprising culturing a host cell according to claim 5 under conditions whereby said polypeptide is produced, and recovering said polypeptide.

8. An isolated nucleic acid molecule comprising a nucleotide sequence that encodes a polypeptide comprising the amino acid sequence of SEQ ID NO:49.

9. The nucleic acid molecule of claim 8, wherein said nucleic acid molecule is DNA.

10. The nucleic acid molecule of claim 8, wherein the polypeptide consists of the amino acid sequence of SEQ ID NO:49.

11. A vector comprising the nucleic acid molecule of claim 8.

12. A cultured host cell harboring a vector according to claim 11.

13. The cell of claim 12, wherein the cell expresses the nucleic acid molecule.

14. A process for the production of a GABA receptor polypeptide, said process comprising culturing a host cell according to claim 12 under conditions whereby said polypeptide is produced, and recovering said polyp eptide.

15. An isolated nucleic acid molecule encoding a GABA receptor, said nucleic acid molecule comprising a nucleotide sequence having at least 95% identity to the nucleotide sequence set forth as SEQ ID NO:48.

16. The nucleic acid molecule of claim 15, wherein said nucleic acid molecule is DNA.

17. The nucleic acid molecule of claim 15, said nucleic acid molecule consisting of a nucleotide sequence having at least 95% identity to the nucleotide sequence set forth as SEQ ID NO:48.

18. A vector comprising the nucleic acid molecule of claim 15.

19. A cultured host cell harboring a vector according to claim 18.

20. The cell of claim 19, wherein the cell expresses the nucleic acid molecule.

21. A process for the production of a GABA receptor polypeptide, said process comprising culturing a host cell according to claim 19 under conditions whereby said polypeptide is produced, and recovering said polypeptide.

22. An isolated nucleic acid molecule encoding a GABA receptor, said nucleic acid molecule comprising a nucleotide sequence having at least 95% identity to a degenerate variant of SEQ ID NO:48.

23. The nucleic acid molecule of claim 22, wherein said nucleic acid molecule is DNA.

24. The nucleic acid molecule of claim 22, said nucleic acid molecule consisting of a nucleotide sequence having at least 95% identity to a degenerate variant of SEQ ID NO:48.

25. A vector comprising the nucleic acid molecule of claim 22.

26. A cultured host cell harboring a vector according to claim 25.

27. The cell of claim 26, wherein the cell expresses the nucleic acid molecule.

28. A process for the production of a GABA receptor polypeptide, said process comprising culturing a host cell according to claim 26 under conditions whereby said polypeptide is produced, and recovering said polypeptide.

29. An isolated nucleic acid molecule that encodes a GABA receptor polypeptide comprising an amino acid sequence having at least 99% identity to the amino acid sequence of SEQ ID NO:49.

30. The nucleic acid molecule of claim 29, wherein said nucleic acid molecule is DNA.

31. A vector comprising the nucleic acid molecule of claim 29.

32. A cultured host cell harboring a vector according to claim 31.

33. The cell of claim 32, wherein the cell expresses the nucleic acid molecule.

34. A process for the production of a GABA receptor polypeptide, said process comprising culturing a host cell according to claim 32 under conditions whereby said polypeptide is produced, and recovering said polypeptide.

35. An isolated nucleic acid molecule that encodes a GABA receptor polypeptide consisting of an amino acid sequence having at least 99% identity to the amino acid sequence of SEQ ID NO:49.

* * * * *